(12) United States Patent
Fischer et al.

(10) Patent No.: US 11,877,743 B2
(45) Date of Patent: Jan. 23, 2024

(54) SYSTEMS AND METHODS FOR MESH DELIVERY AND PREVENTION OF PORT-SITE HERNIA

(71) Applicant: THE TRUSTEES OF THE UNIVERSITY OF PENNSYLVANIA, Philadelphia, PA (US)

(72) Inventors: John Fischer, Philadelphia, PA (US); Rex Peters, Redmond, WA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 437 days.

(21) Appl. No.: 16/340,409

(22) PCT Filed: Oct. 10, 2017

(86) PCT No.: PCT/US2017/055920
§ 371 (c)(1),
(2) Date: Apr. 9, 2019

(87) PCT Pub. No.: WO2018/071409
PCT Pub. Date: Apr. 19, 2018

(65) Prior Publication Data
US 2019/0290262 A1    Sep. 26, 2019

Related U.S. Application Data

(60) Provisional application No. 62/406,709, filed on Oct. 11, 2016.

(51) Int. Cl.
*A61B 17/068* (2006.01)
*A61B 17/00* (2006.01)
(Continued)

(52) U.S. Cl.
CPC ........ *A61B 17/068* (2013.01); *A61B 17/0057* (2013.01); *A61B 17/00234* (2013.01);
(Continued)

(58) Field of Classification Search
CPC . A61B 17/068; A61B 17/0643; A61B 17/064; A61B 17/0057; A61B 17/00234;
(Continued)

(56) References Cited

U.S. PATENT DOCUMENTS 5,263,969 A    11/1993    Phillips
5,830,221 A    11/1998    Stein et al.
(Continued)

FOREIGN PATENT DOCUMENTS

EP    1 595 504 A1    11/2005
WO    WO 1995/030374 A1    11/1995
(Continued)

OTHER PUBLICATIONS

International Search Report dated Dec. 20, 2017 in International Application No. PCT/US2017/055920.
(Continued)

*Primary Examiner* — Brooke Labranche
(74) *Attorney, Agent, or Firm* — Baker Botts L.L.P.

(57) ABSTRACT

The presently disclosed subject matter provides systems and methods for performing minimally invasive surgery. A laparoscopic device for performing minimally invasive surgery can include a mesh configured to be affixed to a fascial tissue to reinforce the fascial tissue. The mesh can be attached to the laparoscopic device before the mesh reaches the fascial tissue. The laparoscopic device can also include a telescoping arm configured to deliver the mesh to the fascial tissue. The telescoping arm can be further configured to position the mesh at the fascial tissue by releasing the mesh from the laparoscopic device.

17 Claims, 58 Drawing Sheets

(51) Int. Cl.
*A61B 17/064* (2006.01)
*A61F 2/02* (2006.01)
*A61B 90/00* (2016.01)
*A61F 2/00* (2006.01)

(52) U.S. Cl.
CPC ........ *A61B 17/064* (2013.01); *A61B 17/0643* (2013.01); *A61F 2/02* (2013.01); *A61B 2017/00004* (2013.01); *A61B 2017/00336* (2013.01); *A61B 2017/00592* (2013.01); *A61B 2017/00597* (2013.01); *A61B 2017/00606* (2013.01); *A61B 2017/00623* (2013.01); *A61B 2017/00637* (2013.01); *A61B 2017/00659* (2013.01); *A61B 2017/00867* (2013.01); *A61B 2017/00991* (2013.01); *A61B 2017/0641* (2013.01); *A61B 2017/0647* (2013.01); *A61B 2090/037* (2016.02); *A61F 2002/0072* (2013.01)

(58) Field of Classification Search
CPC .... A61B 2090/037; A61B 2017/00336; A61B 2017/0647; A61B 2017/00592; A61B 2017/00004; A61B 2017/00597; A61B 2017/00606; A61B 2017/00623; A61B 2017/00637; A61B 2017/00659; A61B 2017/00867; A61B 2017/00991; A61B 2017/0641; A61F 2/02; A61F 2002/0072
See application file for complete search history.

(56) References Cited

U.S. PATENT DOCUMENTS

| | | |
|---|---|---|
| 6,334,446 B1 | 1/2002 | Beyar |
| 6,387,041 B1 | 5/2002 | Harari et al. |
| 2004/0176785 A1 | 9/2004 | Hermann et al. |
| 2005/0049638 A1 | 3/2005 | Mandelbaum |
| 2005/0267529 A1 | 12/2005 | Crockett et al. |
| 2007/0038220 A1 | 2/2007 | Shipp |
| 2007/0185506 A1 | 8/2007 | Jackson |
| 2008/0167520 A1 | 7/2008 | Benderev |
| 2008/0188874 A1 | 8/2008 | Henderson |
| 2009/0204130 A1 | 8/2009 | Kantsevoy et al. |
| 2010/0069930 A1 | 3/2010 | Roslin et al. |
| 2010/0312357 A1 | 12/2010 | Levin et al. |
| 2011/0040311 A1 | 2/2011 | Levin et al. |
| 2011/0054500 A1 | 3/2011 | Ofek et al. |
| 2012/0184805 A1 | 7/2012 | Pulliam et al. |
| 2012/0209401 A1 | 8/2012 | Euteneuer et al. |
| 2013/0018395 A1 | 1/2013 | Friedlander et al. |
| 2016/0120631 A1 | 5/2016 | Murphy |
| 2017/0172551 A1 | 6/2017 | Rao |
| 2017/0319319 A1* | 11/2017 | Fischer ................ A61B 17/064 |

FOREIGN PATENT DOCUMENTS

| | | |
|---|---|---|
| WO | WO 2007/059199 A2 | 5/2007 |
| WO | WO 2010/099327 A1 | 9/2010 |
| WO | WO 2016/141183 A1 | 9/2016 |

OTHER PUBLICATIONS

International Search Report and Written Opinion dated Jul. 26, 2016 in International Application No. PCT/US2016/020685.
Supplementary Partial European Search Report dated Oct. 18, 2018 in EP Application No. 16759493.

* cited by examiner

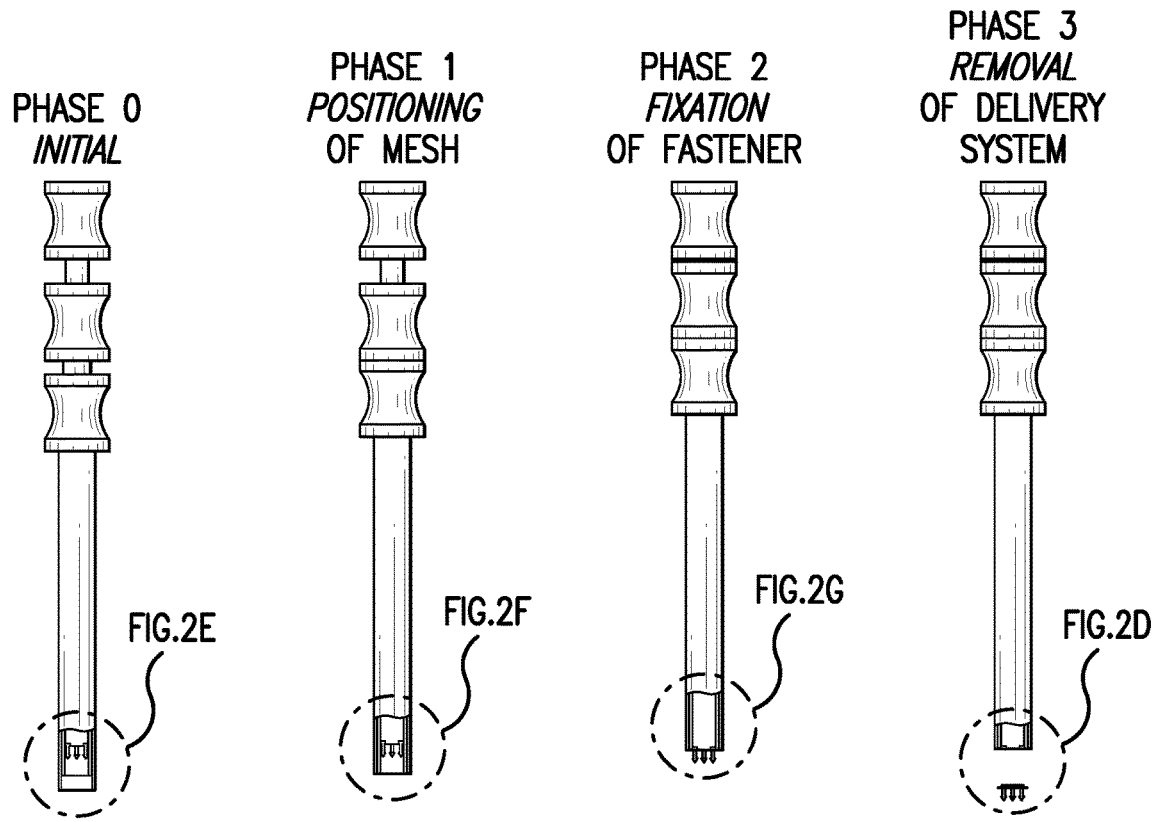
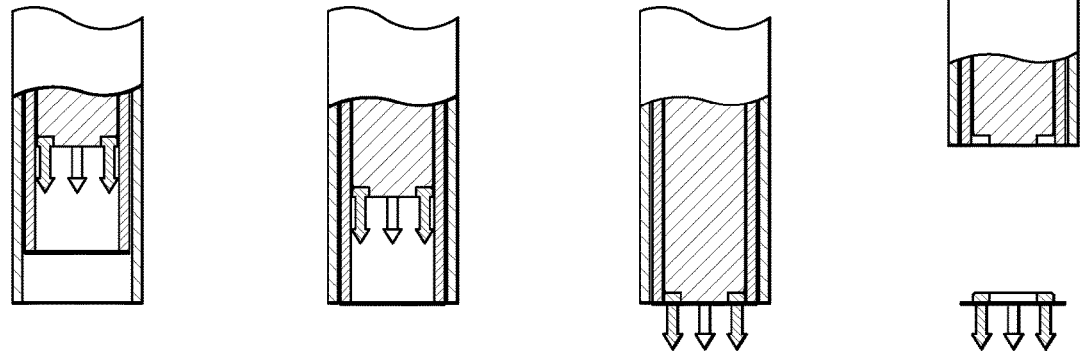
FIG. 2A  FIG. 2B  FIG. 2C  FIG. 2D
FIG. 2E  FIG. 2F  FIG. 2G  FIG. 2H

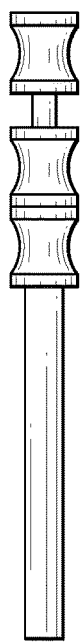 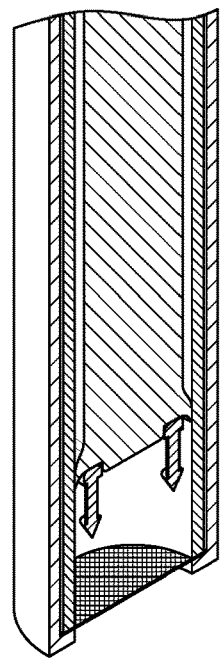
FIG. 4A  FIG. 4B
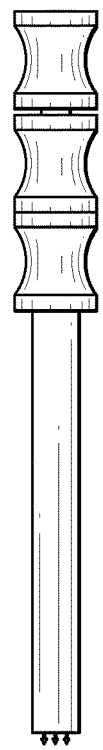 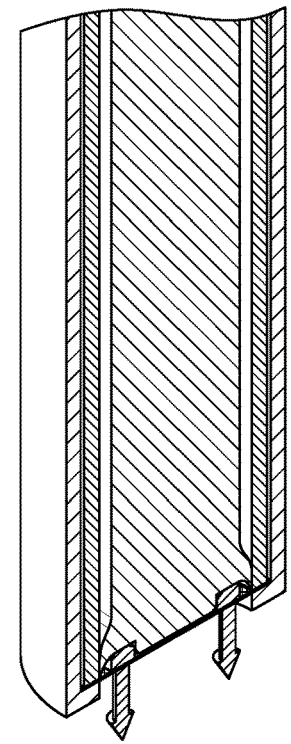
FIG. 5A  FIG. 5B

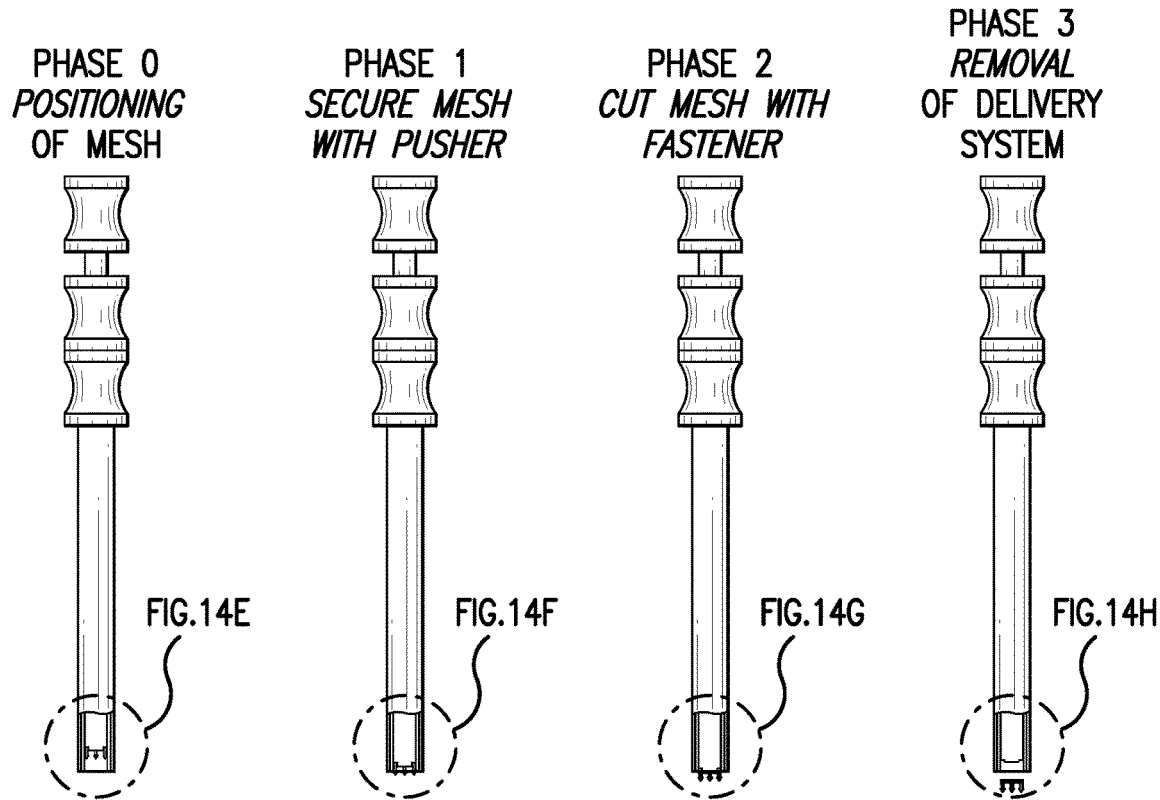
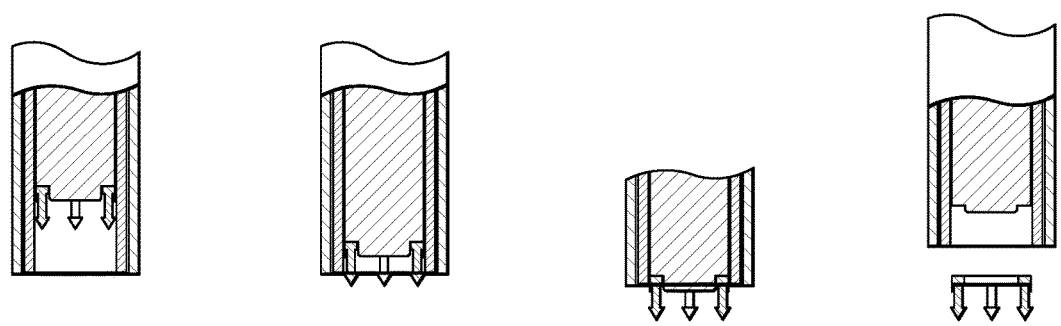
FIG. 14A  FIG. 14B  FIG. 14C  FIG. 14D
FIG. 14E  FIG. 14F  FIG. 14G  FIG. 14H

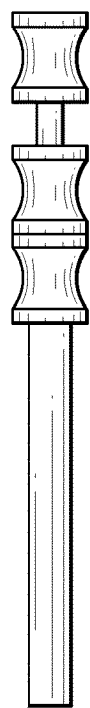 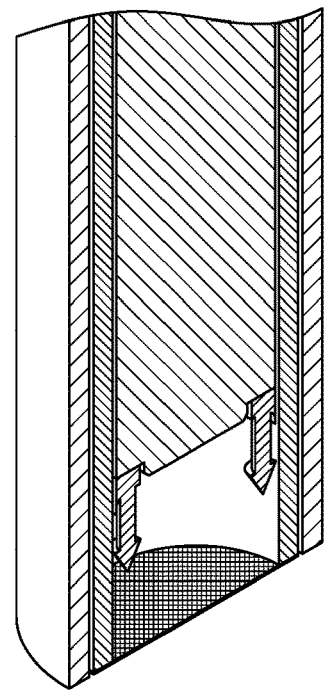
FIG. 15A  FIG. 15B
 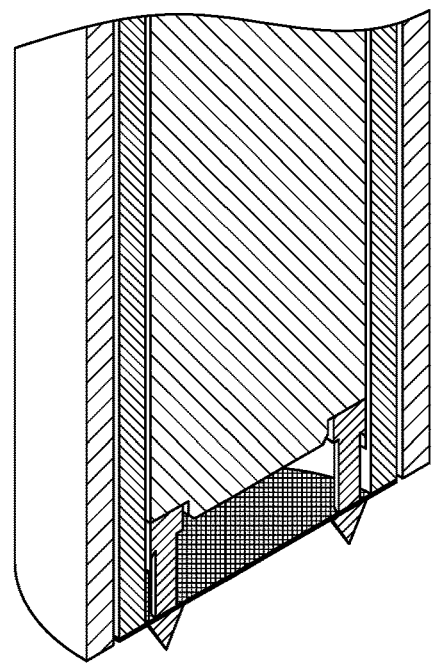
FIG. 16A  FIG. 16B

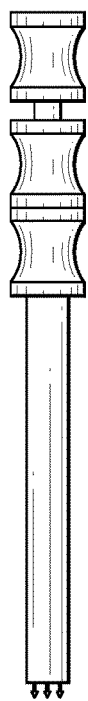 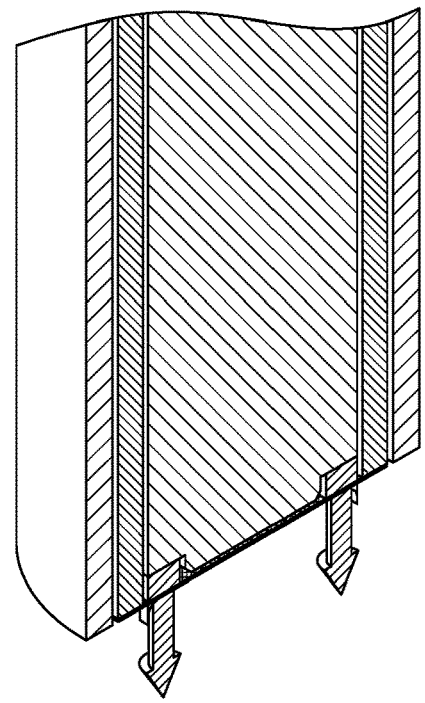
FIG. 17A  FIG. 17B
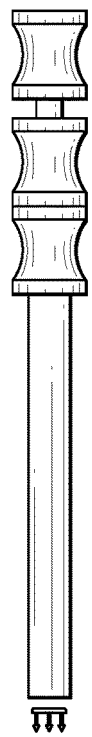 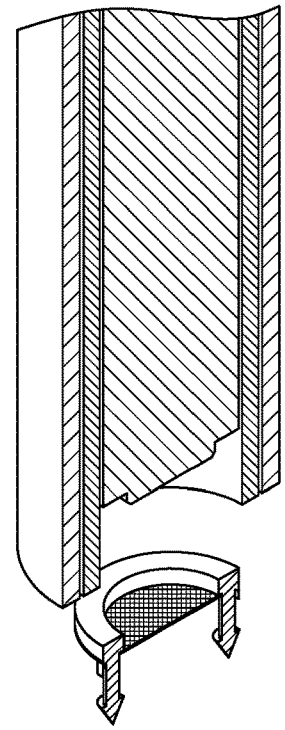
FIG. 18A  FIG. 18B PHASE 0
*INITIAL/ POSITIONING OF MESH*
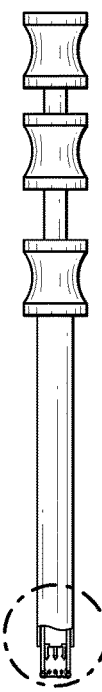
FIG. 19E
FIG. 19A
PHASE 1
*FIXATION OF FASTENER*
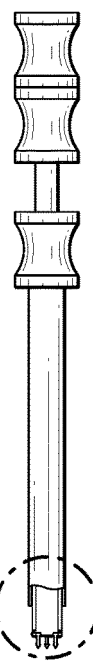
FIG. 19F
FIG. 19B
PHASE 2
*UNGRIP MESH*
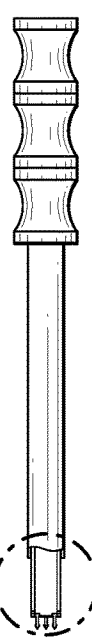
FIG. 19G
FIG. 19C
PHASE 3
*REMOVAL OF DELIVERY SYSTEM*
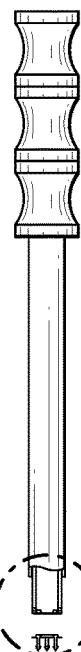
FIG. 19H
FIG. 19D
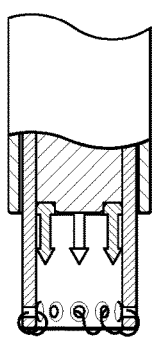
FIG. 19E
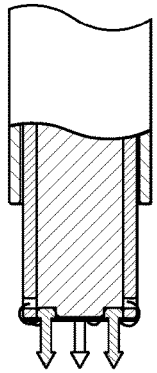
FIG. 19F
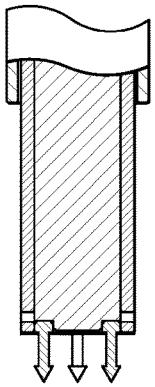
FIG. 19G
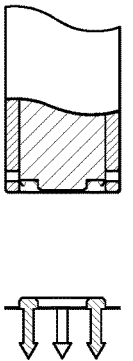
FIG. 19H

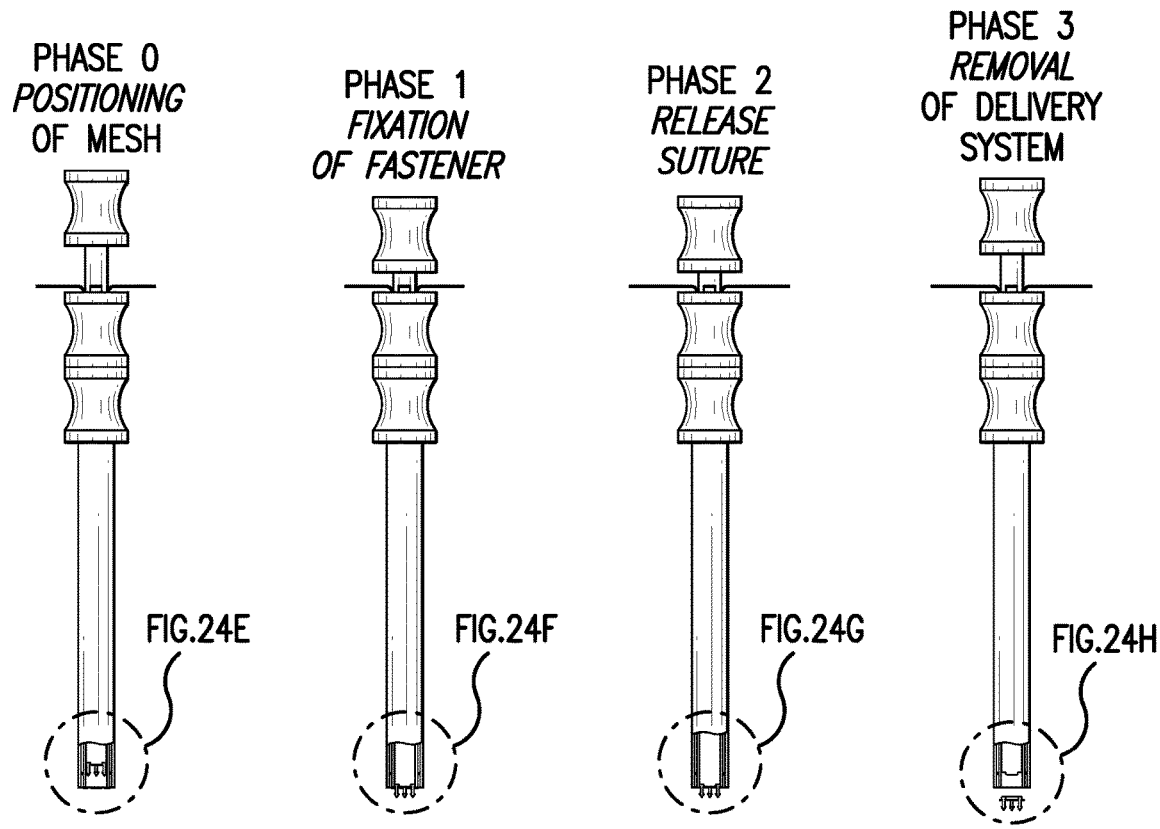
FIG. 24A  FIG. 24B  FIG. 24C  FIG. 24D
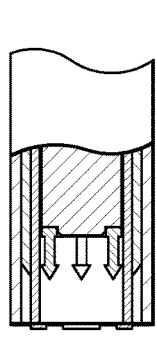 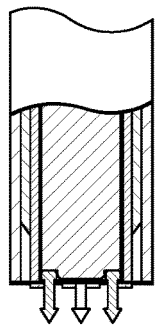 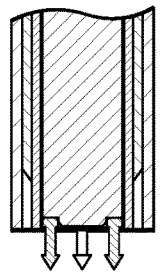 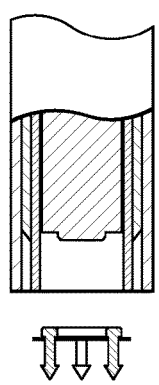
FIG. 24E  FIG. 24F  FIG. 24G  FIG. 24H

PHASE 0
POSITIONING
OF MESH

PHASE 1
SECURE MESH
WITH PUSHER

PHASE 2
CUT MESH WITH
ROTATING INNER
TUBE

PHASE 3
REMOVAL
OF DELIVERY
SYSTEM

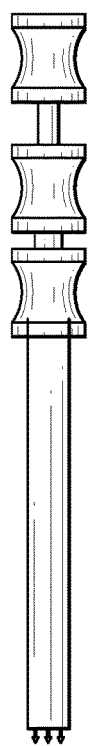 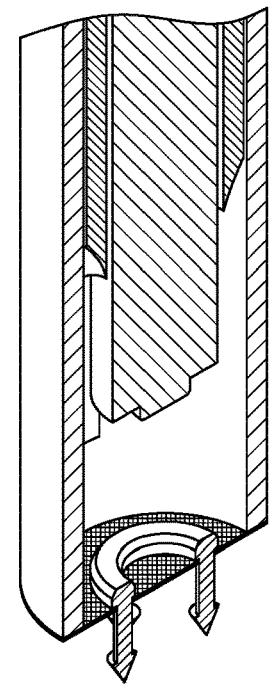
FIG. 30A  FIG. 30B
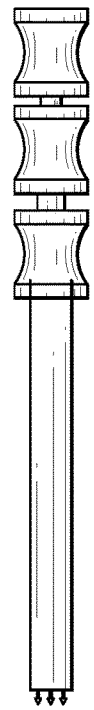 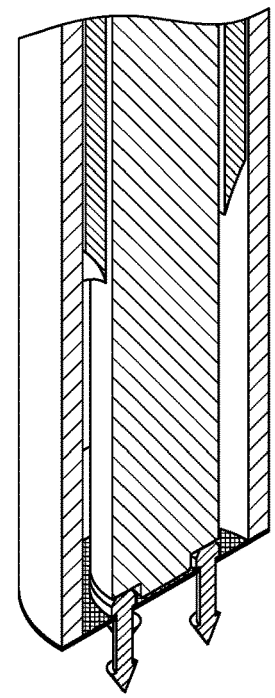
FIG. 31A  FIG. 31B

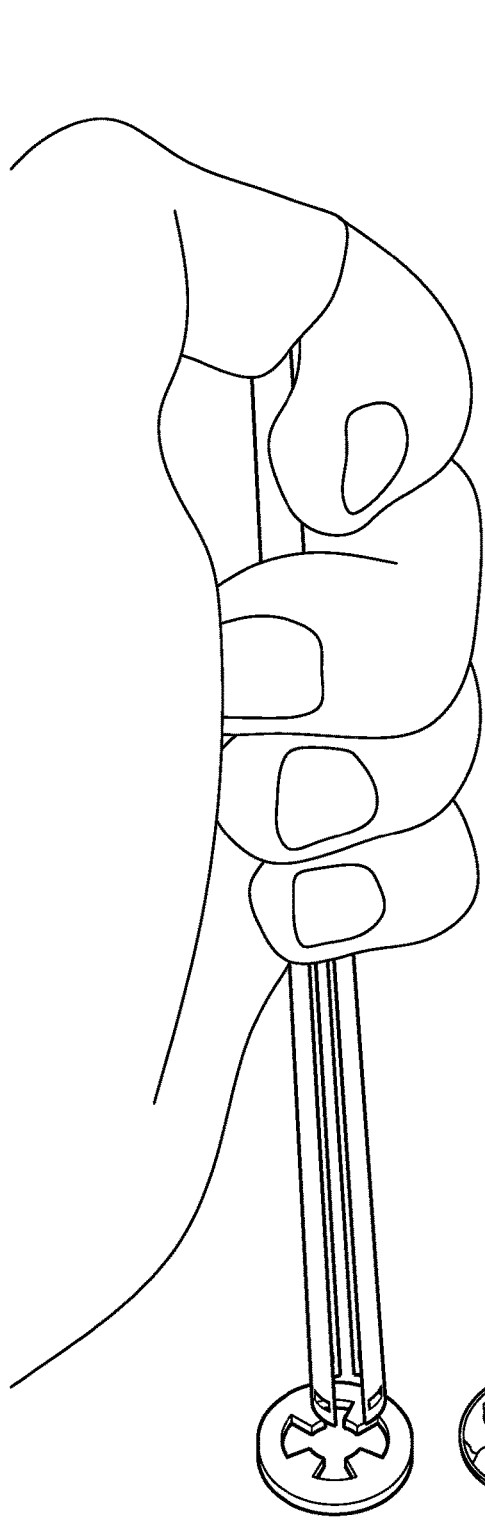 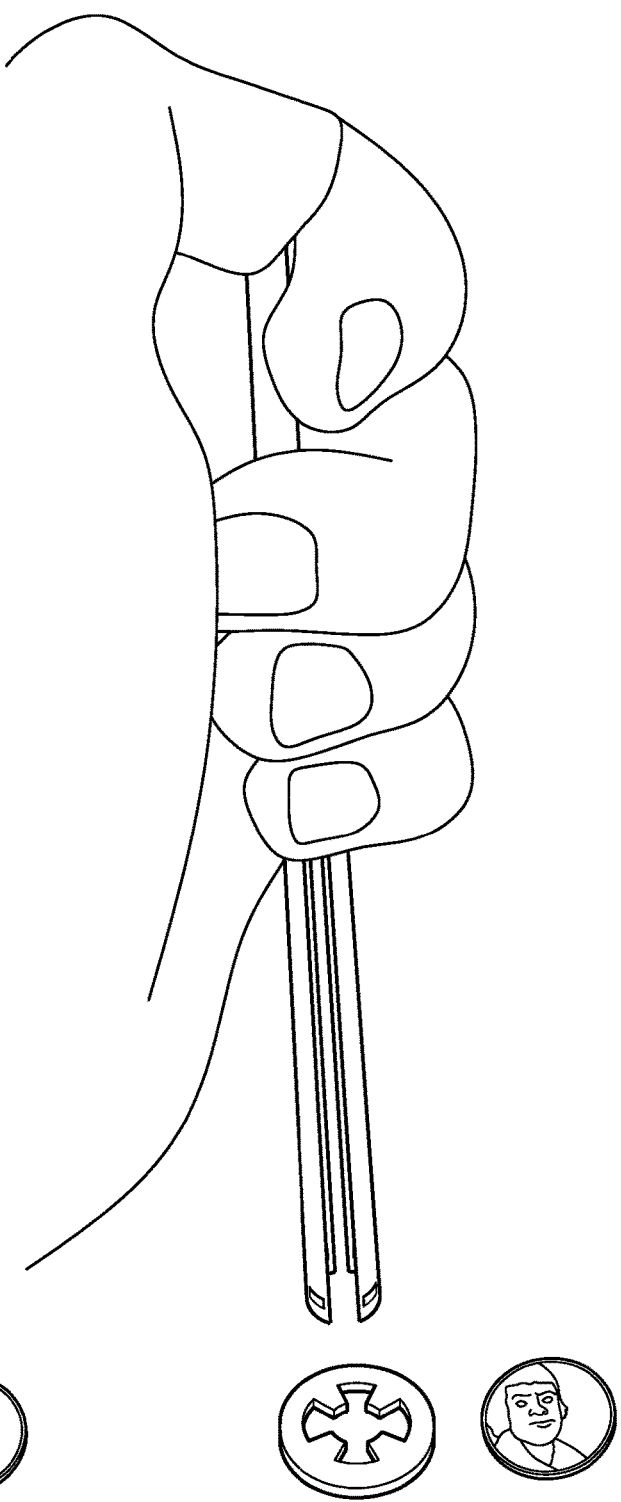
FIG. 43C                              FIG. 43D

SYSTEMS AND METHODS FOR MESH DELIVERY AND PREVENTION OF PORT-SITE HERNIA

CROSS REFERENCE TO RELATED APPLICATION

This application is related to, and claims priority from, Provisional Patent Application No. 62/406,709, entitled "Systems And Methods For Mesh Delivery and Prevention of Port-Site Hernia," which was filed on Oct. 11, 2016, the entire contents of which is incorporated by reference herein.

BACKGROUND

Incisional hernia (IH) is a protrusion of intra-abdominal contents, often intestines, through the abdominal wall, which can be the result of a failed or disrupted fascial closure after surgical incision through the abdominal fascia. The incidence of hernia can be approximately 13% and can be as high as 70% following incisions to the abdominal wall in certain high risk patient populations, with a resulting cost burden. Millions of patients undergo such surgery each year. Further, hernias can be debilitating for patients and associated with a decrease in quality of life.

IH is treated after it occurs, typically reinforced with mesh to reduce subsequent recurrence. However, even with certain available techniques, approximately 1 in 3 repaired hernias can recur, and with each failed repair the chance of success decreases and costs increases. The compounded challenge of failed repairs coupled with associated costs and morbidity, underscores the need for prevention.

One technique to prevent IH is to use prophylactic mesh augmentation (PMA) at the index abdominal surgery procedure to reinforce the fascia of before herniation actually occurs. PMA can be implemented to reduce risk and morbidity, and contain cost in certain high risk patients undergoing abdominal fascial incisions.

A type of IH that occurs in small port sites after surgery is called port site hernia (PSH). PSH is a complication of laparoscopic surgery, carrying a risk of strangulation due to the small size of the defect involved.

A simple, reliable, and precise mechanism and system to provide a prophylactic mesh to small port sites is needed.

SUMMARY

The disclosed subject matter provides a mesh delivery system to deliver prophylactic mesh to small port sites.

In one aspect of the disclosed subject matter, systems for mesh augmentation are provided. In example embodiments, a system can include a telescoping sheath and a small mesh patch with pre-integrated affixation barbs to allow anchoring. The telescoping sheath can be a mesh tension-applicator to engage with the mesh through a mating process with a fastener. Following mating, the mesh can be spatially controlled and incrementally tensioned and precisely affixed to the anterior abdominal fascia or any other tissue construct. The disclosed subject matter can reduce certain technical intra-operative challenges of handling mesh and affixing it to the fascia that are encountered when hand-suturing.

In accordance with an exemplary embodiment, a system for affixing mesh to a fascial incision can include a mesh strip integrated with one or more pre-fabricated and pre-integrated affixation barbs.

BRIEF DESCRIPTION OF THE DRAWINGS

Further features, the nature, and various advantages of the disclosed subject matter will be more apparent from the following detailed description and the accompanying drawings in which:

FIGS. 2A-H illustrate diagrams of the different phases in which the mesh can be positioned and fastened to the telescoping sheath to prepare it for delivery to a target site in accordance with an exemplary embodiment of the disclosed subject matter.

FIG. 4A illustrates a front view of the pusher tube based delivery system depicted in FIG. 3 in a first phase of operation in accordance with another exemplary embodiment of the disclosed subject matter.

FIG. 4B illustrates a magnified sub-view of the bottom portion of the pusher tube based delivery system depicted in FIG. 4A in a first phase of operation in accordance with an exemplary embodiment of the disclosed subject matter.

FIG. 5A illustrates a front view of the pusher tube based delivery system depicted in FIG. 3 in a second phase of operation in accordance with another exemplary embodiment of the disclosed subject matter.

FIG. 5B illustrates a magnified sub-view of the bottom portion of the pusher tube based delivery system depicted in FIG. 5A in a second phase of operation in accordance with an exemplary embodiment of the disclosed subject matter.

FIGS. 14A-H illustrate diagrams of the different phases in which a telescoping sheath delivery system can be prepared for delivering a mesh to a target site in accordance with an exemplary embodiment of the disclosed subject matter.

FIG. 15A illustrates a front view of the telescoping sheath delivery system depicted in FIGS. 14A-H in a first phase of operation in accordance with another exemplary embodiment of the disclosed subject matter.

FIG. 15B illustrates a magnified sub-view of the bottom portion of the telescoping sheath delivery system depicted in FIG. 15A in a first phase of operation in accordance with an exemplary embodiment of the disclosed subject matter.

FIG. 16A illustrates a front view of the telescoping sheath delivery system depicted in FIGS. 14A-H in a second phase of operation in accordance with another exemplary embodiment of the disclosed subject matter.

FIG. 16B illustrates a magnified sub-view of the bottom portion of the telescoping sheath delivery system depicted in FIG. 16A in a second phase of operation in accordance with an exemplary embodiment of the disclosed subject matter.

FIG. 17A illustrates a front view of the telescoping sheath delivery system depicted in FIGS. 14A-H in a third phase of operation in accordance with another exemplary embodiment of the disclosed subject matter.

FIG. 17B illustrates a magnified sub-view of the bottom portion of the telescoping sheath delivery system depicted in FIG. 17A in a third phase of operation in accordance with an exemplary embodiment of the disclosed subject matter.

FIG. 18A illustrates a front view of the telescoping sheath delivery system depicted in FIGS. 14A-H in a fourth phase of operation in accordance with another exemplary embodiment of the disclosed subject matter.

FIG. 18B illustrates a magnified sub-view of the bottom portion of the telescoping sheath delivery system depicted in FIG. 18A in a fourth phase of operation in accordance with an exemplary embodiment of the disclosed subject matter.

FIGS. 19A-H illustrate diagrams of the different phases in which an exemplary telescoping sheath based delivery system in which the mesh to be delivered can be initially grasped with a memory material based suture, can be prepared for delivering a mesh to a target site in accordance with an exemplary embodiment of the disclosed subject matter.

FIGS. 24A-H illustrate diagrams of the different phases of operation an exemplary telescoping sheath based delivery system in which the mesh to be delivered can be initially grasped at defined fixation points with nickel titanium (NiTi) fingers and the NiTi fingers can be retracted after mesh deployment. FIGS. 27A-H illustrate diagrams of the different phases in which the NiTi finger based delivery system can be prepared for delivering a mesh to a target site in accordance with an exemplary embodiment of the disclosed subject matter.

FIG. 27A illustrates a front view of the NiTi finger based delivery system depicted in FIGS. 24A-H in a third phase of operation in accordance with another exemplary embodiment of the disclosed subject matter.

FIG. 27B illustrates a magnified sub-view of the bottom portion of the NiTi finger based delivery system depicted in FIG. 27A in a third phase of operation in accordance with an exemplary embodiment of the disclosed subject matter.

FIGS. 29A-H illustrate diagrams of the different phases in which the rotary cutting mechanism based delivery system can be prepared for delivering a mesh to a target site in accordance with an exemplary embodiment of the disclosed subject matter.

FIG. 30A illustrates a front view of the rotary cutting mechanism based delivery system depicted in FIGS. 29A-H in a first phase of operation in accordance with another exemplary embodiment of the disclosed subject matter.

FIG. 30B illustrates a magnified sub-view of the bottom portion of the rotary cutting mechanism based delivery system depicted in FIG. 30A in a first phase of operation in accordance with an exemplary embodiment of the disclosed subject matter.

FIG. 31A illustrates a front view of the rotary cutting mechanism based delivery system depicted in FIGS. 29A-H in a second phase of operation in accordance with another exemplary embodiment of the disclosed subject matter.

FIG. 31B illustrates a magnified sub-view of the bottom portion of the rotary cutting mechanism based delivery system depicted in FIG. 31A in a second phase of operation in accordance with an exemplary embodiment of the disclosed subject matter.

FIG. 43A-D illustrate that the telescoping laparoscopic mesh delivery system(s) can deliver the mesh using an interior energizer.

Figure 1:
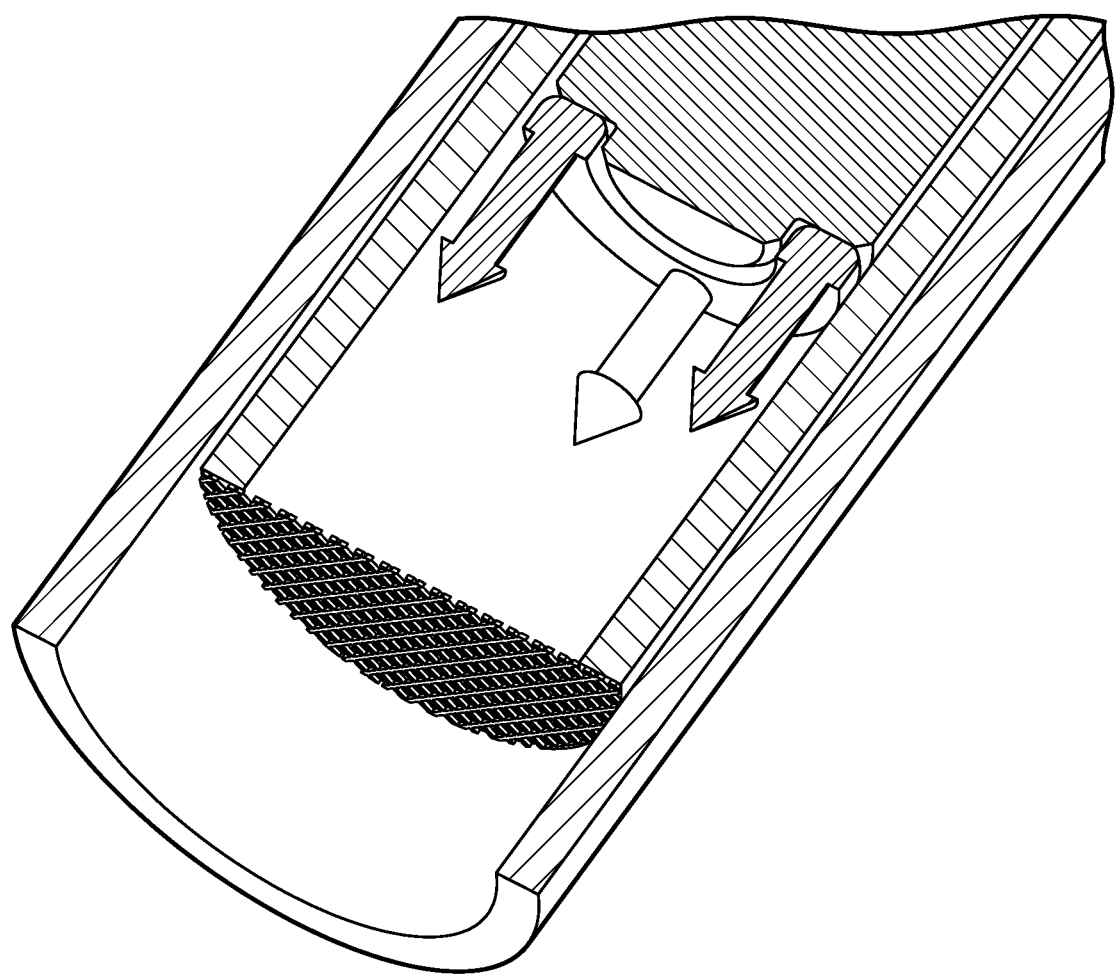
FIG. 1 illustrates a cross-sectional view of a bottom portion of a telescoping sheath with a mesh patch in accordance with an exemplary embodiment of the disclosed subject matter.

Throughout the drawings, the same reference numerals and characters, unless otherwise stated, are used to denote like features, elements, components or portions of the illustrated embodiments. Moreover, while the disclosed subject matter will now be described in detail with reference to the figures, it is done so in connection with the illustrative embodiments.

DETAILED DESCRIPTION

The disclosed subject matter provides systems and methods for delivering prophylactic mesh to small port sites.

Generally, for purpose of illustration and not limitation, one aspect of the disclosed subject matter includes a custom mesh applicator, in the form of a telescoping sheath, to engage with a pre-fabricated mesh strip, then stretch and precisely affix a mesh strip to one or more subcutaneous tissues of the abdomen at the small port site. As used herein, the term "mesh strip" is not limited to a mesh of any particular geometric. One of skill in the art will appreciate, for example, that a "mesh strip" can include a mesh construct of differing geometry, size, or composition.

As embodied herein, the fastener-anchors can include a fastener for engaging with the applicator and an anchor for insertion into tissue at the small port site. The fastener-anchors can be formed from a single piece or can include a plurality of pieces. For example, as described herein, the fastener for engaging with the applicator and the anchor for insertion into the small port site can be separate pieces coupled or affixed together. Alternatively, the fastener for engaging with the applicator and the anchor for insertion to the small port site can include different portions of a single piece. For purpose of clarity, the term "fastener," as used herein, can refer to the fastener-anchor collectively.

In some embodiments, fasteners can be adapted to be integrated with a mesh strip. The fastener can be disposed over the mesh strip such that an anchor is passed through a loop or hole of the mesh. Additionally and/or alternatively, and in accordance with an exemplary embodiment, the fastener can include a plurality of radial arms, each of which have one or more structural features suitable for integration with the mesh strip. For example, each radial arm can include a tab or post that is short relative to the anchor and can be inserted into a loop or hole of the mesh strip. In this manner, the fastener can be integrated across a larger surface area of the mesh to achieve stability during tensioning and enhance integration into mesh. Additionally and or alternatively, the fasteners can be pre-integrated with the mesh and manufactured together. For example, and not limitation, the fasteners can be integrally formed with or bonded to the mesh.

As embodied herein, for purpose of illustration, fasteners in accordance with various embodiments can include three components. First, the fasteners can include a fastener portion or mating post for interfacing with the applicator as described herein. Second, the fasteners can include an anchor or tissue penetrating mechanism. This mechanism can be an existing anchor or tacks or a special purpose anchor configured to integrate with the system described herein. The anchor/tissue penetrating mechanism can, for example, snap into the fastener portion. Third, the fasteners can include an under piece or bottom piece that integrates with the fastener portion/mating post to lock the fasteners into the mesh to be controlled with our without the tissue penetrating mechanism. The anchor/tissue penetrating mechanism can, for example, snap into the fastener portion or the bottom piece.

Moreover, in certain embodiments, the fasteners need not be pre-integrated with an anchor. Rather, for example and not limitation, the fasteners can include a top fastener portion and a bottom portion for affixation to the mesh and can also include a target, such as a hole or sink, for receiving an anchor after tensioning has occurred. That is, the fasteners can be integrated into the mesh so that the applicator may be used to appropriately tension the mesh and then, once the mesh has been tensioned and positioned over a desired area, e.g., a tissue incision, the anchors can be inserted and the mesh can be affixed to the tissue.

Additionally and/or alternatively, in connection with certain embodiments, the fasteners can be interested into the mesh such that an applicator can tension the mesh and allow for subsequent insertion of tacks or anchors through other areas of the mesh. For example, the fasteners can have a grommet shape, and the applicator can have protrusions adapted to be inserted into the center of the fasteners to allow for tensioning. One of skill in the art will appreciate that the fasteners of this embodiments, as well as others, can be formed in the mesh or can be formed from separate pieces and integrated with the mesh. Once the mesh is tensioned, the surgeon can apply tacks or anchors and then release the applicator by withdrawing the protrusions from the fasteners.

For purpose of illustration, and not limitation, additional embodiments of the mesh strip will be described. As described herein, the mesh strip is the material that can be affixed onto the subcutaneous tissue at the small port site during surgical access to the abdomen. The fasteners can be the anchors that are attached to the mesh strip in order to serve 2 purposes: (i) to interact with the tissue by penetrating and affixing onto it; and (ii) to interact with the applicator (e.g., the laparoscopic telescoping sheath) and allow for full control and the ability to quantify the amount of tension being put on the mesh strip. The mesh strip can include, for example, Phasix mesh or polyprophylene monofilament. One of skill in the art will appreciate that various types of mesh strip can be used. The mesh strip can be cut in a variety of orientations. For example, the mesh strip can be cut in a horizontal configuration, a vertical configuration, or at an angle, such as 45 degrees. The mesh strip can also have a variety of dimensions as desired. The number of fasteners on each side of the mesh can also be varied. For example, the mesh strip can have 2 or 3 fasteners per side.

In certain embodiments, the disclosed mesh strip can be formed from a permanent synthetic absorbable or non-absorbable mesh, a biologic mesh, or bio-absorbable mesh or a hybrid mesh formed from components of each. The mesh strip can be integrated with any number of uni-directional fasteners in various orientations and positions. In an embodiment, each fastener can be disposed at an edge of the mesh strip. The anchor of each fastener can include one or more barbed affixations adapted for a predetermined depth of fascia penetration. In an exemplary embodiment the mesh may be anchored by the automated application of biologic or biomedical adhesive or glue, either discretely or in combination with mechanical anchoring.

In addition to the aforementioned embodiments the mesh strip can have a variety of different sizes and shapes and orientations. Additionally the mesh can have features that allowing it to self-adhere, allow for user mediated mechanical fixation, and additionally can simply be glued to the fascial tissue. Additionally the mesh can be applied to one or both sides that is the anterior posterior surface of the aponeurosis. Additionally the mesh strip can be delivered via an external device onto the fascial tissue.

Several different types of meshes and/or mesh strips can be used with the disclosed subject matter. For purposes of illustration and not limitation, self-adhesive meshes, prolene soft mesh, polypropylene mesh, polyester mesh, vicryl mesh, monocryl mesh, porous meshes, laminate meshes, bio-absorbable meshes, non-absorbable meshes, biologic meshes, multi-layered meshes, composite meshes, integrated design meshes, synthetic meshes, and several other types of meshes can be used. The disclosed subject matter is not limited to any particular type or types of meshes that can be used for enhancing a fascia closure. The mesh strip can be cut in a variety of orientations. For example, the mesh strip can be cut in a horizontal configuration, a vertical configuration, or at an angle, such as 45 degrees. Cutting at a 45-degree angle can change the stretching characteristics of the mesh and can allow the mesh to have a higher stiffness. In other embodiments, the mesh strip can be cut in other angles and/or orientations.

In some embodiments, the mesh can be affixed to the fascia using an adhesive. The adhesive can be a synthetic and/or biological fluid and/or liquid material used to affix the mesh to the fascia with or without sutures. In some embodiments, the mesh can be affixed to the fascia by applying acrylate compounds to the mesh (e.g., n-butyl cyanoacrylate (GLUBRAN 2), n-hexyl cyanoacrylate (IFABOND), and n-octyl cyanoacrylate (EVOBOND)). In some embodiments, the adhesive used to affix the mesh to the fascia can be fibrin glue.

Description will now be made to various embodiments of this aspect of the disclosed subject matter for purpose of illustration and not limitation. Although the embodiments described herein are described primarily with reference to laparoscopic hernia repair and/or hernia prevention, one of skill in the art would appreciate that the subject matter disclosed herein can also be applied to a variety of other procedures. For example, in addition to being used to treat and augment hernia tissue closures, the disclosed subject matter can be utilized for open inguinal hernia repair for mesh reinforcement. As another example, for purpose of illustration and not limitation, the disclosed subject matter can also be utilized for laparoscopic surgery, including laparoscopic hiatal hernia, ventral or incisional hernia, inguinal hernia, or the like. Additionally, the disclosed subject matter can be utilized for augmentation and/or reinforcement of laparoscopic port sites following laparoscopic procedures.

Moreover, although the embodiments herein are described primarily with reference to the tensioning and affixation of mesh constructs, one of skill in the art will also appreciate that the disclosed subject matter can also include tensioning and applying other constructs, such as tissue, in a similar manner by integrating fasteners into those constructs. For example, the disclosed subject matter can be utilized to apply a tension-set soft tissue for skin closure or to incrementally close a wound subject to the application of tension. Other applications intended to fall within the scope of the disclosed subject matter include, for purpose of illustration and not limitation, reinforcement and re-contouring of the fascia after rectus fascia plication for abdominoplasty (using mesh), and tendon or joint repair, where tendon can be adapted into the fastener anchor and controlled and tensioned with an applicator so as to re-affix or reconstruct the tendon or joint capsule.

FIG. 1 illustrates a cross-sectional view of a bottom portion of a telescoping sheath with a mesh patch. FIGS. 2A-H illustrate diagrams of the different phases in which the mesh can be positioned and fastened to the telescoping sheath to prepare it for delivery to a target site. As shown in FIGS. 2A-D, the bottom portion of the telescoping sheath includes the mesh. FIGS. 2E-H are magnified sub-views of the bottom portion of the telescoping mesh shown in FIGS. 2A-D, respectively. The inner and outer tubes of the telescoping sheath can grasp the mesh and position the mesh as shown in the first and second phases (e.g., phase 0 and phase 1) as shown in FIGS. 2A, 2B, 2E, and 2F. Movement of a pusher tube of the telescoping sheath can assist with fixating a fastener to the mesh in the third phase (e.g., phase 2) as shown in FIGS. 2C and 2G. In the fourth phase (e.g., phase 3), the delivery system, which includes the mesh, can be removed from the telescoping sheath as shown in FIGS. 2D and 211.

Figure 3:
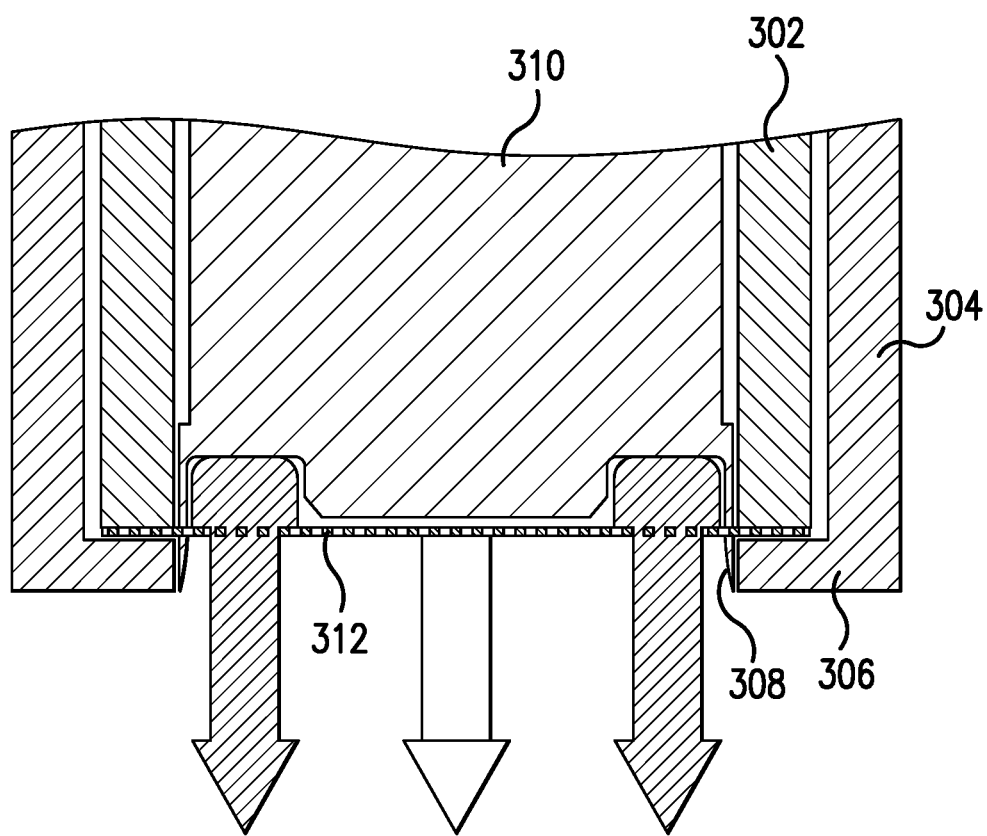
FIG. 3 illustrates a cross-sectional view of an exemplary telescoping sheath based delivery system that uses a pusher tube to position and deliver the mesh in accordance with another exemplary embodiment of the disclosed subject matter.

FIG. 3 illustrates a cross-sectional view of an exemplary telescoping sheath based delivery system shown in FIGS. 1 and 2 that uses a pusher tube to position and deliver the mesh. As FIG. 3 shows, the mesh 312 can be grasped with inner tubes 302 and outer tubes 304, deployed, and then cut with a pusher 310. Component 306 can hold the mesh 312 in place, and in particular can hold the excess mesh that will not be used in place, and cutting guide 308 can trim the excess mesh, thereby allowing the central mesh to be fastened and incorporated into the incision. In some embodiments, component 306 and cutting guide 308 can represent a mechanism for the mesh 312 to be held with inside the system of FIG. 3.

FIG. 4A illustrates a front view of the pusher tube based delivery system depicted in FIG. 3 in a first phase of operation. FIG. 4B illustrates a magnified sub-view of the bottom portion of the pusher tube based delivery system depicted in FIG. 4A in a first phase of operation. As FIGS. 4A and 4B illustrate, the mesh can be secured between the inner and the outer tube of the bottom portion of the telescoping sheath. A fastener can be attached to a middle portion of the pusher tube. The pusher tube can have a sharp edge along its outer diameter to sever the mesh.

FIG. 5A illustrates a front view of the pusher tube based delivery system depicted in FIG. 3 in a second phase of operation. FIG. 5B illustrates a magnified sub-view of the bottom portion of the pusher tube based delivery system depicted in FIG. 5A in a second phase of operation. As FIGS. 5A and 5B illustrate, in the second phase, the pusher tube can be moved forward to engage the fastener that can be attached to it with the mesh.

Figure 6A:
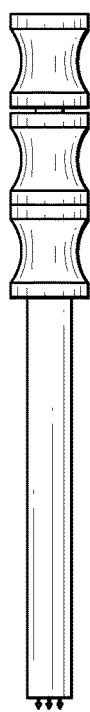
FIG. 6A illustrates a front view of the pusher tube based delivery system depicted in FIG. 3 in a third phase of operation in accordance with another exemplary embodiment of the disclosed subject matter.
Figure 6B:
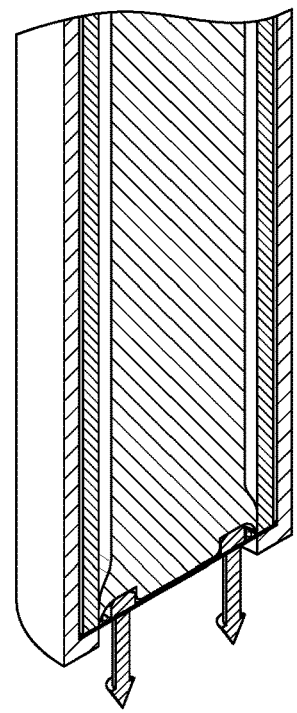
FIG. 6B illustrates a magnified sub-view of the bottom portion of the pusher tube based delivery system depicted in FIG. 6A in a third phase of operation in accordance with an exemplary embodiment of the disclosed subject matter.

FIG. 6A illustrates a front view of the pusher tube based delivery system depicted in FIG. 3 in a third phase of operation. FIG. 6B illustrates a magnified sub-view of the bottom portion of the pusher tube based delivery system depicted in FIG. 6A in a third phase of operation. As FIGS. 6A and 6B illustrate, in the third phase, the pusher tube can be further advanced forward than in the second phase to cut the mesh.

Figure 7A:
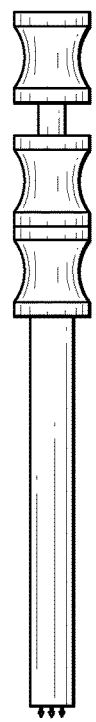
FIG. 7A illustrates a front view of the pusher tube based delivery system depicted in FIG. 3 in a fourth phase of operation in accordance with another exemplary embodiment of the disclosed subject matter.
Figure 7B:
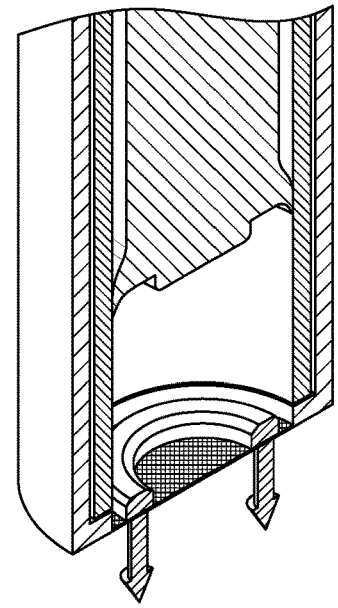
FIG. 7B illustrates a magnified sub-view of the bottom portion of the pusher tube based delivery system depicted in FIG. 7A in a fourth phase of operation in accordance with an exemplary embodiment of the disclosed subject matter.

FIG. 7A illustrates a front view of the pusher tube based delivery system depicted in FIG. 3 in a fourth phase of operation. FIG. 7B illustrates a magnified sub-view of the bottom portion of the pusher tube based delivery system depicted in FIG. 7A in a fourth phase of operation. As FIGS. 7A and 7B illustrate, in the fourth phase, the pusher tube can be released, leaving the mesh and the fastener, ready to be delivered to the target site.

Figure 8:
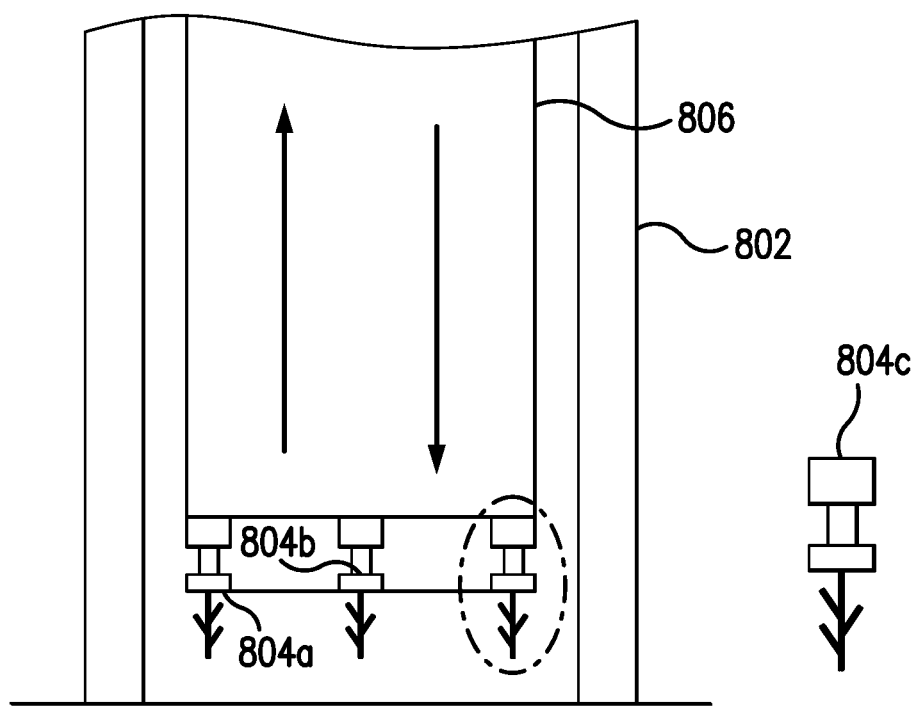
FIG. 8 illustrates a cross-sectional view of an exemplary telescoping sheath based delivery system that uses a mesh that can be pre-attached to a fastener that can be fixed to a pusher via a frangible joint to deliver the mesh in accordance with another exemplary embodiment of the disclosed subject matter.

FIG. 8 illustrates a cross-sectional view of an exemplary telescoping sheath based delivery system that uses a mesh that can be pre-attached to a fastener that can be fixed to a pusher via a frangible joint to deliver the mesh. In some embodiments, the fastener can be fixed to the pusher by other elements instead of a frangible joint (e.g., perforated material, plastic ring, nichrome wire, etc.).

The exemplary telescoping sheath based delivery system of FIG. 8 can include an outer sheath 802, anvil 806 for delivery of the mesh system. The delivery system can include a top surface 804A of the fastener associated with the mesh. The delivery system can also include a breakaway component 804B on the anterior surface of the fastener anchor. The fastener anchor can be connected to the mating component on the anvil, allowing for release of the mesh and fastener anchor system. The delivery system can also include a mated and/or connected and/or fixed fastener 804C and a component on the anvil which can be secured.

Figures 9A, 9B, 9C, 9D:
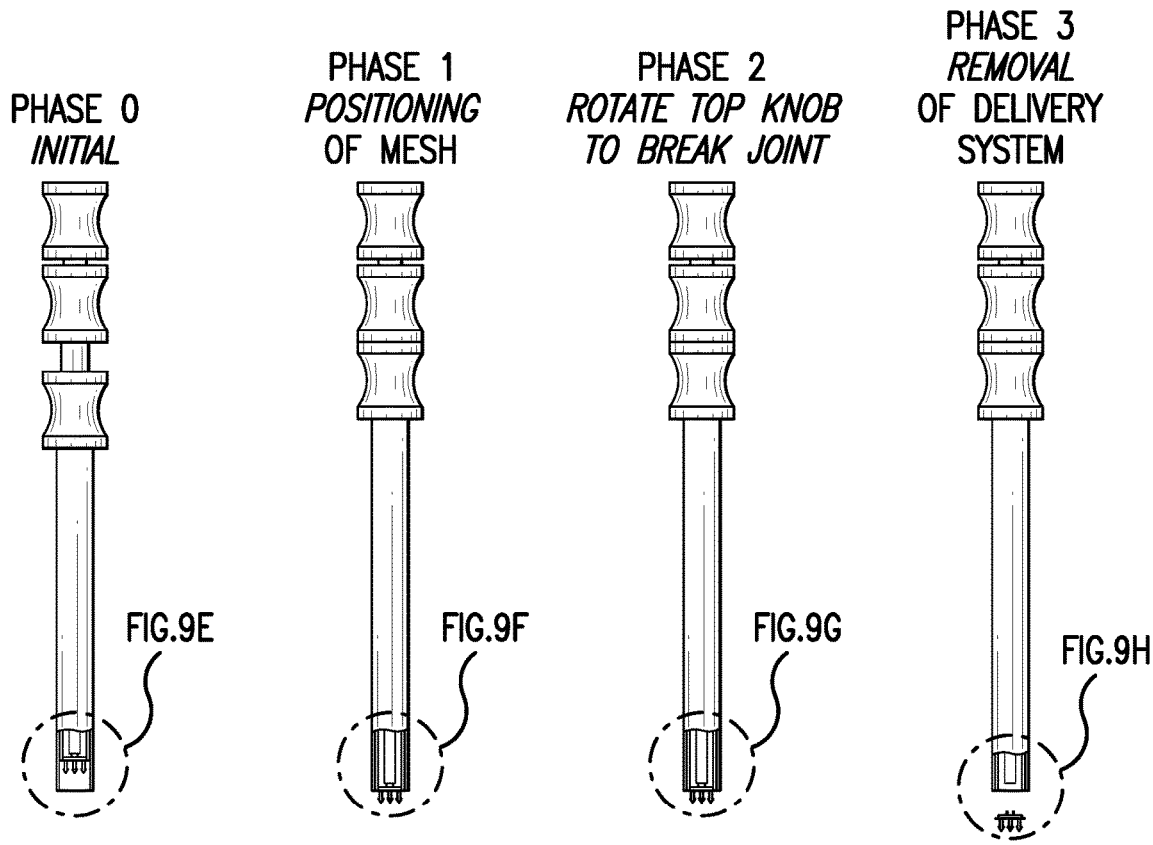
FIGS. 9A-H illustrate diagrams of the different phases in which the frangible joint based delivery system can be prepared for delivering a mesh to a target site in accordance with an exemplary embodiment of the disclosed subject matter.
Figures 9E, 9F, 9G, 9H:
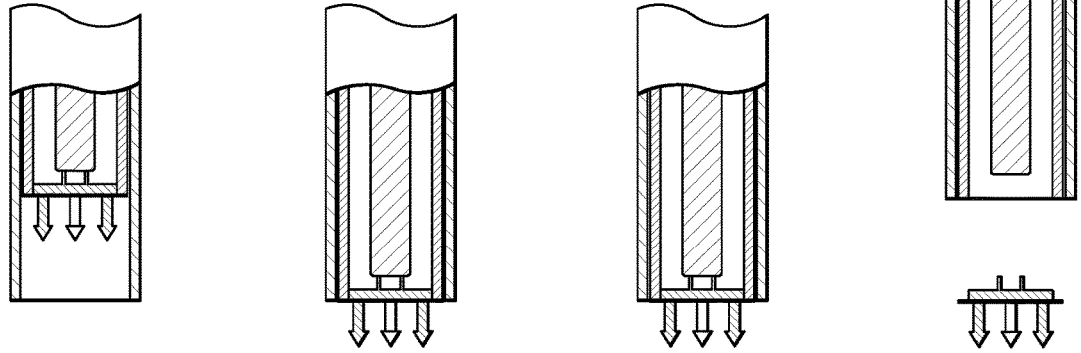

FIGS. 9A-H illustrate diagrams of the different phases in which the frangible joint based delivery system can be prepared for delivering a mesh to a target site. As shown in FIGS. 9A-D, the bottom portion of the telescoping sheath includes the mesh. FIGS. 9E-H are magnified sub-views of the bottom portion of the telescoping mesh shown in FIGS. 9A-D, respectively. The inner tubes of the telescoping sheath can grasp the mesh and position the mesh as shown in the first and second phases (e.g., phase 0 and phase 1) as shown in FIGS. 9A, 9B, 9E, and 9F. Movement of a pusher tube of the telescoping sheath can assist with fixating a fastener to the mesh in the third phase (e.g., phase 2) as shown in FIGS. 9C and 9G. Furthermore, in the third phase, the top knob of the telescoping sheath can be rotated to break the joint. In the fourth phase (e.g., phase 3), the delivery system, which includes the mesh, can be removed from the telescoping sheath as shown in FIGS. 9D and 9H. FIGS. 9A-H illustrate the breakaway version that of the delivery system that is illustrated by FIG. 8.

Figure 10A:
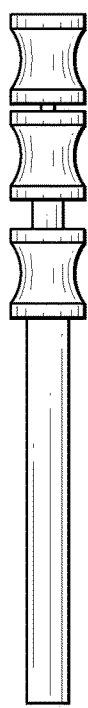
FIG. 10A illustrates a front view of the frangible joint based delivery system depicted in FIGS. 8 and 9 in a first phase of operation in accordance with another exemplary embodiment of the disclosed subject matter.
Figure 10B:
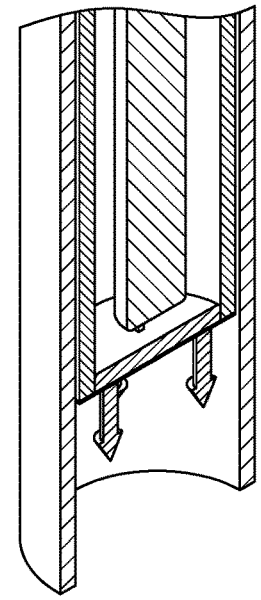
FIG. 10B illustrates a magnified sub-view of the bottom portion of the frangible joint based delivery system depicted in FIG. 10A in a first phase of operation in accordance with an exemplary embodiment of the disclosed subject matter.

FIG. 10A illustrates a front view of the frangible joint based delivery system depicted in FIGS. 8 and 9 in a first phase of operation in accordance with another exemplary embodiment of the disclosed subject matter. FIG. 10B illustrates a magnified sub-view of the bottom portion of the frangible joint based delivery system depicted in FIG. 10A in a first phase of operation. As FIGS. 10A and 10B illustrate, in the first phase, the mesh can be attached to the inner tube of the telescoping sheath. The fastener can be weakly joined to the pusher tube in a middle portion of the pusher tube. For example, the ability of the fastener to be weakly joined can include the ability to be broken and/or torn away by the user, allowing the manual and/or automated tensioning of the tube to reliably detach. One or more fasteners can be pre-attached to the mesh.

Figure 11A:
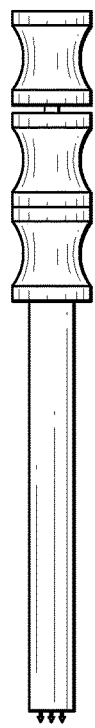
FIG. 11A illustrates a front view of the frangible joint based delivery system depicted in FIGS. 8 and 9 in a second phase of operation in accordance with another exemplary embodiment of the disclosed subject matter.
Figure 11B:
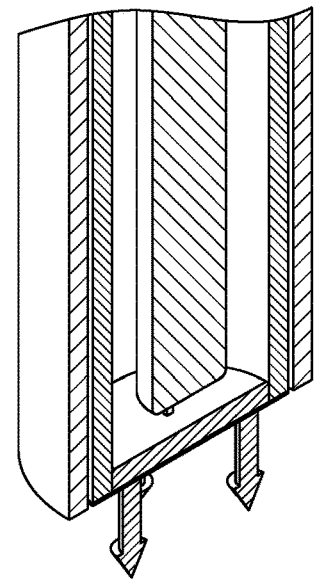
FIG. 11B illustrates a magnified sub-view of the bottom portion of the frangible joint based delivery system depicted in FIG. 11A in a second phase of operation in accordance with an exemplary embodiment of the disclosed subject matter.

FIG. 11A illustrates a front view of the frangible joint based delivery system depicted in FIGS. 8 and 9 in a second phase of operation. FIG. 11B illustrates a magnified sub-view of the bottom portion of the frangible joint based delivery system depicted in FIG. 11A in a second phase of operation. As FIGS. 11A and 11B illustrate, in the second phase, the pusher and the middle tubes can be advanced forward to secure the fastener and the mesh to the target tissue to which the mesh is to be attached and/or delivered.

Figure 12A:
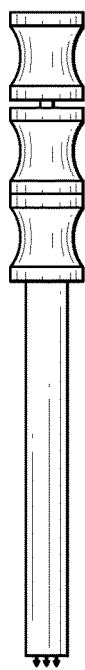
FIG. 12A illustrates a front view of the frangible joint based delivery system depicted in FIGS. 8 and 9 in a third phase of operation in accordance with another exemplary embodiment of the disclosed subject matter.
Figure 12B:
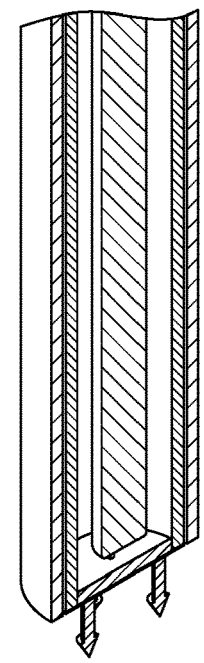
FIG. 12B illustrates a magnified sub-view of the bottom portion of the frangible joint based delivery system depicted in FIG. 12A in a third phase of operation in accordance with an exemplary embodiment of the disclosed subject matter.

FIG. 12A illustrates a front view of the frangible joint based delivery system depicted in FIGS. 8 and 9 in a third phase of operation. FIG. 12B illustrates a magnified sub-view of the bottom portion of the frangible joint based delivery system depicted in FIG. 12A in a third phase of operation. As FIGS. 12A and 12B illustrate, in the third phase, the pusher tube can be rotated using the top knob of the telescoping sheath to break the joint with the fastener.

Figure 13A:
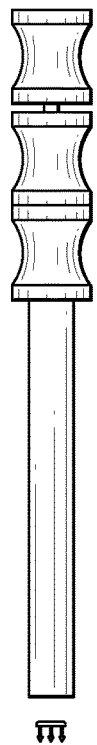
FIG. 13A illustrates a front view of the frangible joint based delivery system depicted in FIGS. 8 and 9 in a fourth phase of operation in accordance with another exemplary embodiment of the disclosed subject matter.
Figure 13B:
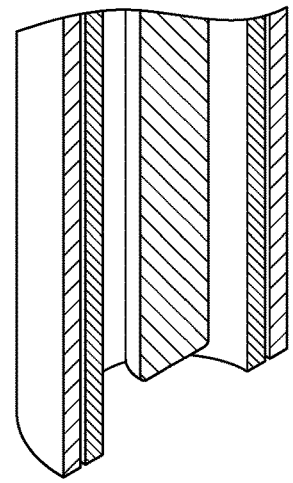
FIG. 13B illustrates a magnified sub-view of the bottom portion of the frangible joint based delivery system depicted in FIG. 13A in a fourth phase of operation in accordance with an exemplary embodiment of the disclosed subject matter.
Figure 13B:
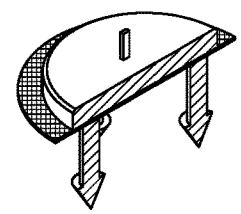

FIG. 13A illustrates a front view of the frangible joint based delivery system depicted in FIGS. 8 and 9 in a fourth phase of operation. FIG. 13B illustrates a magnified sub-view of the bottom portion of the frangible joint based delivery system depicted in FIG. 13A in a fourth phase of operation. As FIGS. 13A and 13B illustrate, in the fourth phase, the delivery system can be removed from the telescoping sheath The mesh can be removed from the telescoping sheath by being withdrawn separately and/or integrally.

FIGS. 14A-H illustrate diagrams of the different phases in which the telescoping sheath delivery system can be prepared for delivering a mesh to a target site. As shown in FIGS. 14A-D, the bottom portion of the telescoping sheath includes the mesh. FIGS. 14E-H are magnified sub-views of the bottom portion of the telescoping mesh shown in FIGS. 14A-D, respectively. In the first phase (e.g., phase 0), the mesh can be positioned as shown in FIGS. 14A and 14E. In the second phase (e.g., phase 1), the mesh can be secured with the pusher tube as shown in FIGS. 14B and 14F. Movement of the pusher tube of the telescoping sheath can cut the mesh with a fastener in the third phase (e.g., phase 2) as shown in FIGS. 14C and 14G. In the fourth phase (e.g., phase 3), the delivery system, which includes the mesh, can be removed from the telescoping sheath as shown in FIGS. 14D and 14H. In some embodiments, the plunger can dislodge the mesh assembly.

FIG. 15A illustrates a front view of the telescoping sheath delivery system depicted in FIGS. 14A-H and in a first phase of operation. FIG. 15B illustrates a magnified sub-view of the bottom portion of the telescoping sheath delivery system depicted in FIG. 15A in a first phase of operation. As FIGS. 15A and 15B illustrate, in the first phase, the mesh can be attached to the inner tube at only four corners of the mesh. The fastener can be attached to the pusher tube and the fastener can have a cutting edge on its outer periphery.

FIG. 16A illustrates a front view of the telescoping sheath delivery system depicted in FIGS. 14A-H in a second phase of operation. FIG. 16B illustrates a magnified sub-view of the bottom portion of the telescoping sheath delivery system depicted in FIG. 16A in a second phase of operation. As FIGS. 16A and 16B illustrate, in the second phase, the pusher tube can be advanced forward to engage the fastener with the mesh.

FIG. 17A illustrates a front view of the telescoping sheath delivery system depicted in FIGS. 14A-H in a third phase of operation. FIG. 17B illustrates a magnified sub-view of the bottom portion of the telescoping sheath delivery system depicted in FIG. 17A in a third phase of operation. As FIGS. 17A and 17B illustrate, in the third phase, the pusher tube can be advanced forward to its full extent to cut the mesh at the fixation points.

FIG. 18A illustrates a front view of the telescoping sheath delivery system depicted in FIGS. 14A-H in a fourth phase of operation. FIG. 18B illustrates a magnified sub-view of the bottom portion of the telescoping sheath delivery system depicted in FIG. 18A in a fourth phase of operation. As FIGS. 18A and 18B illustrate, in the fourth phase, the delivery system can be removed from the telescoping sheath The mesh can be removed from the telescoping sheath by being withdrawn separately and/or integrally.

FIGS. 19A-H illustrates diagrams of the different phases of operation of an exemplary telescoping sheath based delivery system in which the mesh to be delivered can be initially grasped with a memory material based (e.g., nitinol) suture and the suture can be removed after mesh deployment. In some embodiments, any other type of shape-memory material and/or alloy (e.g., Ag—Cd 44/49 at. % Cd, Au—Cd 46.5/50 at. % Cd, Cu—Al—Ni 14/14.5 wt % Al and 3/4.5 wt % Ni, Cu—Sn approx. 15 at % Sn, Cu—Zn 38.5/41.5 wt. % Zn, Cu—Zn—X (X=Si, Al, Sn), Fe—Pt approx. 25 at. % Pt, Mn—Cu 5/35 at % Cu, Fe—Mn—Si, Co—Ni—Al, Co—Ni—Ga, Ni—Fe—Ga, Ti—Nb, Ni—Ti approx. 55-60 wt % Ni, Ni—Ti—Hf, Ni—Ti—Pd, Ni—Mn—Ga, etc.) in addition and/or instead of nitinol can be used for the sutures. FIGS. 19A-H illustrates diagrams of the different phases in which the memory material suture based delivery system can be prepared for delivering a mesh to a target site. As shown in FIGS. 19A-D, the bottom portion of the telescoping sheath includes the mesh. FIGS. 19E-H are magnified sub-views of the bottom portion of the telescoping mesh shown in FIGS. 19A-D, respectively. In the first phase (e.g., phase 0), the mesh can be positioned as shown in FIGS. 19A and 19E. In the second phase (e.g., phase 1), the mesh can be fixed using a fastener as the pusher tube advances forward along the telescoping sheath as shown in FIGS. 19B and 19F. Further movement of the pusher tube of the telescoping sheath can ungrip the mesh in the third phase (e.g., phase 2) as shown in FIGS. 19C and 19G. In the fourth phase (e.g., phase 3), the delivery system, which includes the mesh, can be removed from the telescoping sheath as shown in FIGS. 19D and 19H.

Figure 20A:
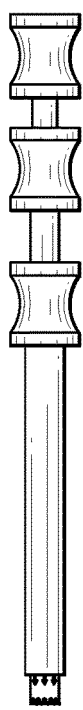
FIG. 20A illustrates a front view of the memory material suture based delivery system depicted in FIGS. 19A-H in a first phase of operation in accordance with another exemplary embodiment of the disclosed subject matter.
Figure 20B:
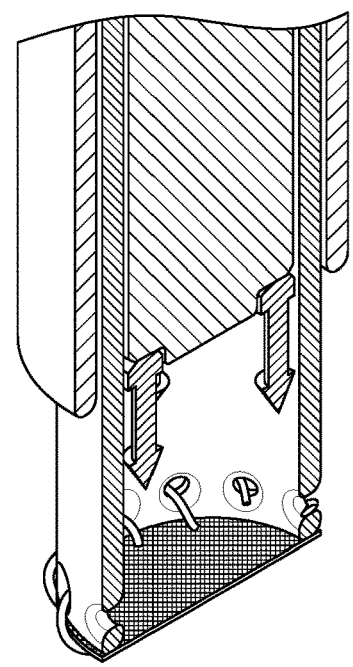
FIG. 20B illustrates a magnified sub-view of the bottom portion of the memory material suture based delivery system depicted in FIG. 20A in a first phase of operation in accordance with an exemplary embodiment of the disclosed subject matter.

FIG. 20A illustrates a front view of the memory material suture based delivery system depicted in FIGS. 19A-H in a first phase of operation. FIG. 20B illustrates a magnified sub-view of the bottom portion of the memory material suture based delivery system depicted in FIG. 20A in a first phase of operation. As FIGS. 20A and 20B illustrate, in the first phase, the mesh can be attached to the inner tube with a suture. The fastener can be attached to the pusher tube.

Figure 21A:
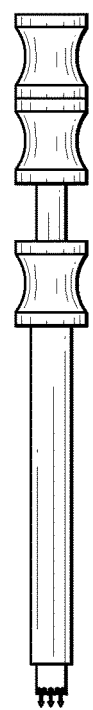
FIG. 21A illustrates a front view of the memory material suture based delivery system depicted in FIGS. 19A-H in a second phase of operation in accordance with another exemplary embodiment of the disclosed subject matter.
Figure 21B:
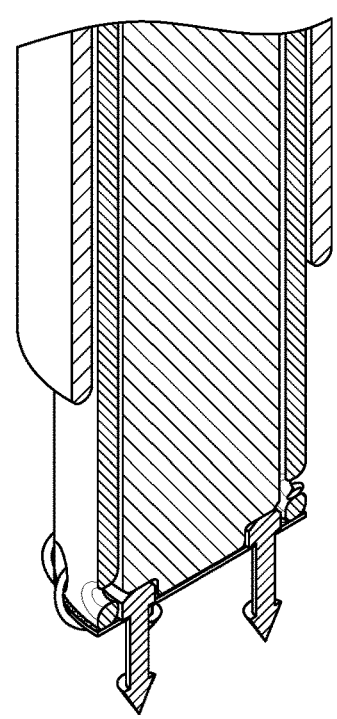
FIG. 21B illustrates a magnified sub-view of the bottom portion of the memory material suture based delivery system depicted in FIG. 21A in a second phase of operation in accordance with an exemplary embodiment of the disclosed subject matter.

FIG. 21A illustrates a front view of the memory material based delivery system depicted in FIGS. 19A-H in a second phase of operation. FIG. 21B illustrates a magnified sub-view of the bottom portion of the memory material based delivery system depicted in FIG. 21A in a second phase of operation. As FIGS. 21A and 21B illustrate, in the second phase, the pusher tube can be advanced forward and the fastener can be engaged with the mesh. The fasteners can be driven (e.g., nailed) through the mesh, and can be glued as well.

Figure 22A:
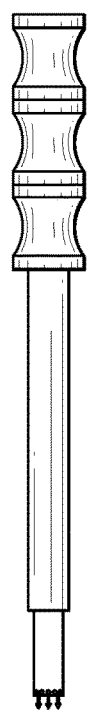
FIG. 22A illustrates a front view of the memory material suture based delivery system depicted in FIGS. 19A-H in a third phase of operation in accordance with another exemplary embodiment of the disclosed subject matter.
Figure 22B:
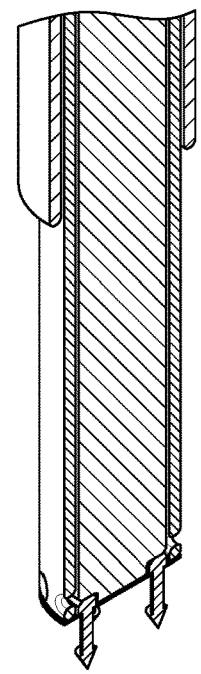
FIG. 22B illustrates a magnified sub-view of the bottom portion of the memory material suture based delivery system depicted in FIG. 22A in a third phase of operation in accordance with an exemplary embodiment of the disclosed subject matter.

FIG. 22A illustrates a front view of the memory material suture based delivery system depicted in FIGS. 19A-H in a third phase of operation. FIG. 22B illustrates a magnified sub-view of the bottom portion of the memory material suture based delivery system depicted in FIG. 22A in a third phase of operation. As FIGS. 22A and 22B illustrate, in the third phase, the memory material suture can be removed. The suture can be removed by being cut and withdrawn.

Figure 23A:
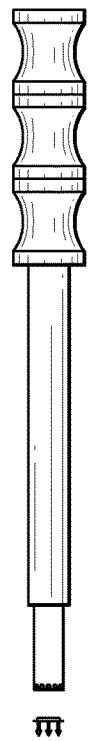
FIG. 23A illustrates a front view of the memory material suture based delivery system depicted in FIGS. 19A-H in a fourth phase of operation in accordance with another exemplary embodiment of the disclosed subject matter.
Figure 23B:
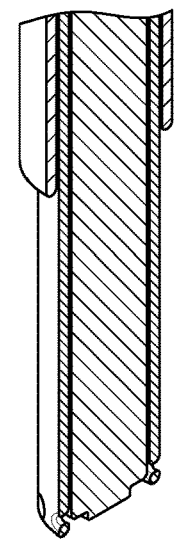
FIG. 23B illustrates a magnified sub-view of the bottom portion of the memory material suture based delivery system depicted in FIG. 23A in a fourth phase of operation in accordance with an exemplary embodiment of the disclosed subject matter.
Figure 23B:
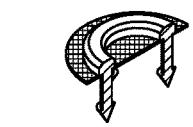

FIG. 23A illustrates a front view of the memory material suture based delivery system depicted in FIGS. 19A-H in a fourth phase of operation. FIG. 23B illustrates a magnified sub-view of the bottom portion of the memory material suture based delivery system depicted in FIG. 23A in a fourth phase of operation. As FIGS. 23A and 23B illustrate, in the fourth phase, the delivery system can be removed from the telescoping sheath by being withdrawn from the telescoping sheath.

FIGS. 24A-H illustrates diagrams of the different phases of operation of an exemplary telescoping sheath based delivery system in which the mesh to be delivered can be initially grasped at defined fixation points with nickel titanium (NiTi) fingers and the NiTi fingers can be retracted after mesh deployment. FIGS. 24A-H illustrates diagrams of the different phases in which the NiTi finger based delivery system can be prepared for delivering a mesh to a target site. As shown in FIGS. 24A-D, the bottom portion of the telescoping sheath includes the mesh. FIGS. 24E-H are magnified sub-views of the bottom portion of the telescoping mesh shown in FIGS. 24A-D, respectively. In the first phase (e.g., phase 0), the mesh can be positioned as shown in FIGS. 24A and 24E. In the second phase (e.g., phase 1), the mesh can be fixed using a fastener as the pusher tube advances forward along the telescoping sheath as shown in FIGS. 24B and 24F. Further movement of the pusher tube of the telescoping sheath can release the suture in the third phase (e.g., phase 2) as shown in FIGS. 24C and 27G. In the fourth phase (e.g., phase 3), the delivery system, which includes the mesh, can be removed from the telescoping sheath as shown in FIGS. 24D and 24H.

Figure 25A:
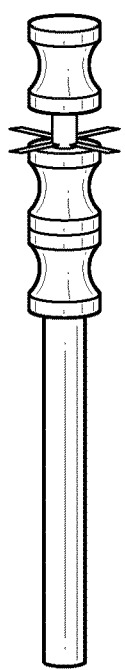
FIG. 25A illustrates a front view of the NiTi finger based delivery system depicted in FIGS. 24A-H in a first phase of operation in accordance with another exemplary embodiment of the disclosed subject matter.
Figure 25B:
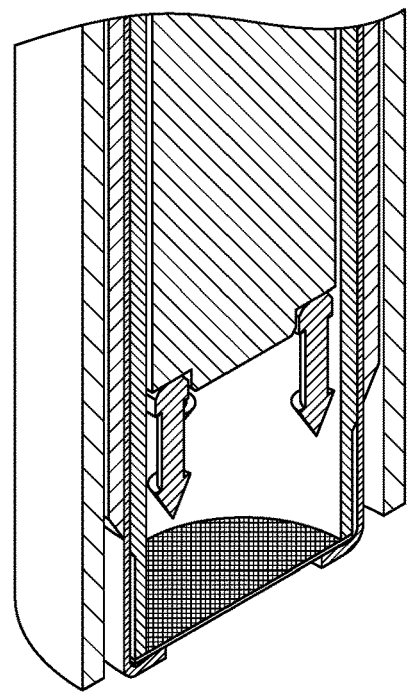
FIG. 25B illustrates a magnified sub-view of the bottom portion of the NiTi finger based delivery system depicted in FIG. 25A in a first phase of operation in accordance with an exemplary embodiment of the disclosed subject matter.

FIG. 25A illustrates a front view of the NiTi finger based delivery system depicted in FIGS. 24A-H in a first phase of operation. FIG. 25B illustrates a magnified sub-view of the bottom portion of the NiTi finger based delivery system depicted in FIG. 25A in a first phase of operation. As FIGS. 25A and 25B illustrate, in the first phase, the mesh can be secured between the inner tube of the telescoping sheath and the retractable NiTi fingers.

Figure 26A:
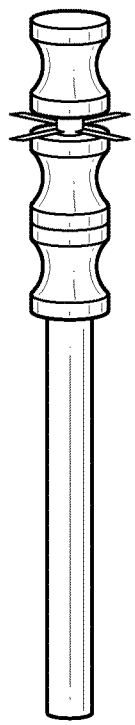
FIG. 26A illustrates a front view of the NiTi finger based delivery system depicted in FIGS. 24A-H in a second phase of operation in accordance with another exemplary embodiment of the disclosed subject matter.
Figure 26B:
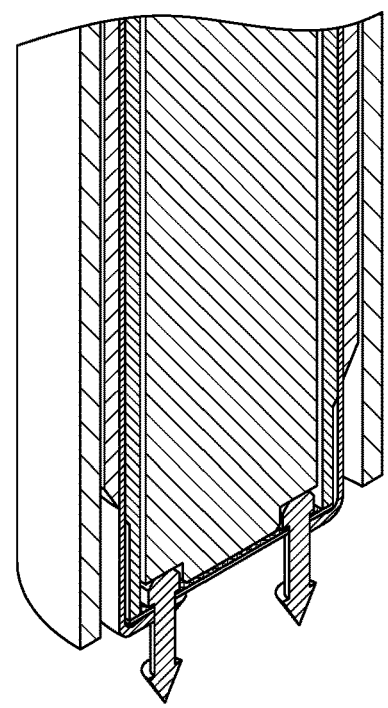
FIG. 26B illustrates a magnified sub-view of the bottom portion of the NiTi finger based delivery system depicted in FIG. 26A in a second phase of operation in accordance with an exemplary embodiment of the disclosed subject matter.

FIG. 26A illustrates a front view of the NiTi finger based delivery system depicted in FIGS. 24A-H in a second phase of operation. FIG. 26B illustrates a magnified sub-view of the bottom portion of the NiTi finger based delivery system depicted in FIG. 26A in a second phase of operation. As FIGS. 26A and 26B illustrate, in the second phase, the pusher tube can be advanced forward to engage the fastener with the mesh.

Figure 27A:
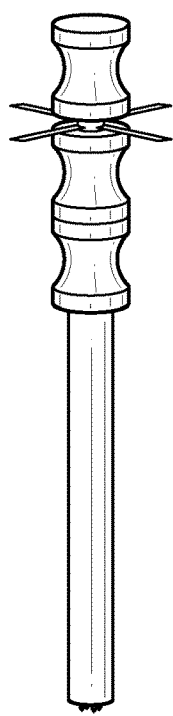
Figure 27B:
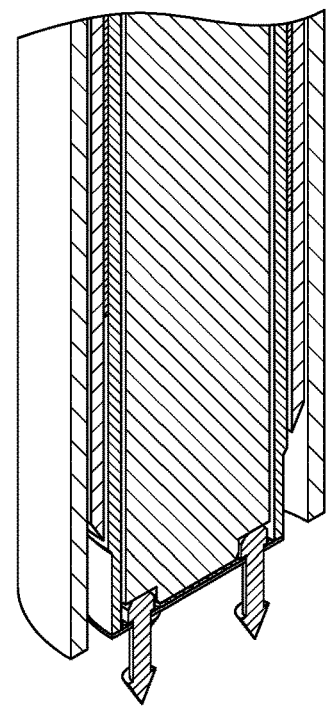

FIG. 27A illustrates a front view of the NiTi finger based delivery system depicted in FIGS. 24A-H in a third phase of operation. FIG. 27B illustrates a magnified sub-view of the bottom portion of the NiTi finger based delivery system depicted in FIG. 27A in a third phase of operation. As FIGS. 27A and 27B illustrate, in the third phase, the NiTi fingers can be retracted to release the mesh. The NiTi fingers can be retracted manually and/or mechanically.

Figure 28A:
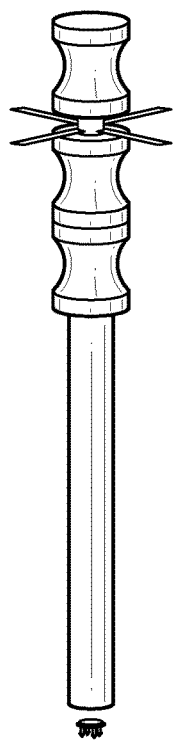
FIG. 28A illustrates a front view of the NiTi finger based delivery system depicted in FIGS. 24A-H in a fourth phase of operation in accordance with another exemplary embodiment of the disclosed subject matter.
Figure 28B:
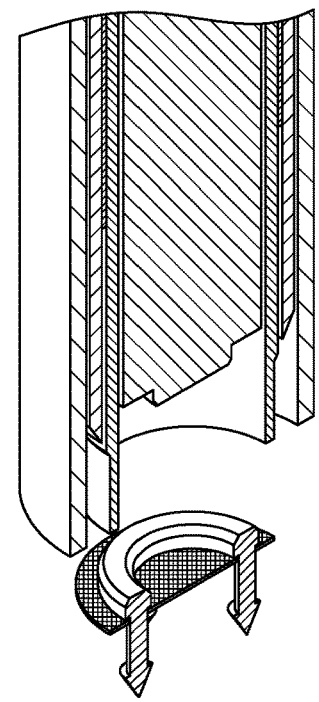
FIG. 28B illustrates a magnified sub-view of the bottom portion of the NiTi finger based delivery system depicted in FIG. 28A in a fourth phase of operation in accordance with an exemplary embodiment of the disclosed subject matter.

FIG. 28A illustrates a front view of the NiTi finger based delivery system depicted in FIGS. 24A-H in a fourth phase of operation. FIG. 28B illustrates a magnified sub-view of the bottom portion of the NiTi finger based delivery system depicted in FIG. 28A in a fourth phase of operation. As FIGS. 28A and 28B illustrate, in the fourth phase, the delivery system can be removed from the telescoping sheath. The mesh can be removed from the telescoping sheath by being withdrawn separately and/or integrally.

Figure 29A:
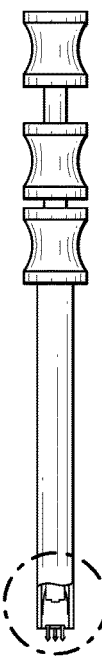
FIGS. 29A-H illustrate diagrams of the different phases of operation of an exemplary telescoping sheath based delivery system in which the mesh to be delivered can be initially grasped at defined fixation points, deployed, and cut using rotary cutting mechanism after mesh deployment.
Figure 29B:
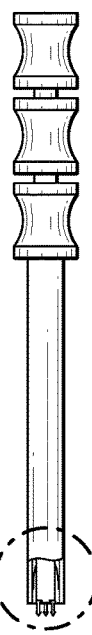
Figure 29C:
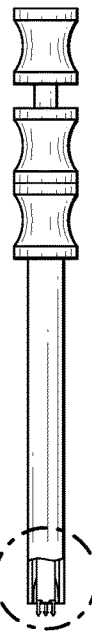
Figure 29D:
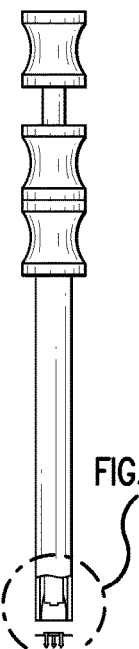
Figure 29E:
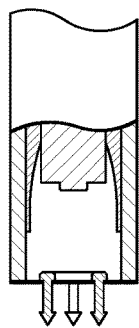
Figure 29F:
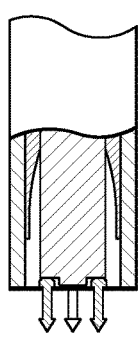
Figure 29G:
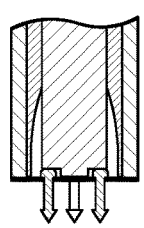
Figure 29H:
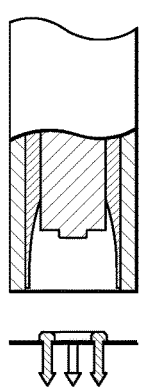

FIGS. 29A-H illustrates diagrams of the different phases of operation of an exemplary telescoping sheath based delivery system in which the mesh to be delivered can be initially grasped at defined fixation points, deployed, and cut using rotary cutting mechanism after mesh deployment. Example embodiments of such rotary cutting mechanisms can include can opener, reciprocating blade, angled blade, ring cutter, etc. FIGS. 29A-H illustrates diagrams of the different phases in which the rotary cutting mechanism based delivery system can be prepared for delivering a mesh to a target site. As shown in FIGS. 29A-D, the bottom portion of the telescoping sheath includes the mesh. FIGS. 29E-H are magnified sub-views of the bottom portion of the telescoping mesh shown in FIGS. 29A-D, respectively. In the first phase (e.g., phase 0), the mesh can be positioned as shown in FIGS. 29A and 29E. In the second phase (e.g., phase 1), the mesh can be secured as the pusher tube advances forward along the telescoping sheath as shown in FIGS. 29B and 29F. In the third phase (e.g., phase 2), the mesh can be cut by rotating the inner tube as shown in FIGS. 29C and 29G. In the fourth phase (e.g., phase 3), the delivery system, which includes the mesh, can be removed from the telescoping sheath as shown in FIGS. 29D and 29H.

FIG. 30A illustrates a front view of the rotary cutting mechanism based delivery system depicted in FIGS. 29A-H in a first phase of operation. FIG. 30B illustrates a magnified sub-view of the bottom portion of the rotary cutting mechanism based delivery system depicted in FIG. 30A in a first phase of operation. As FIGS. 30A and 30B illustrate, in the first phase, the mesh can be attached to the outer tube of the telescoping sheath. The fastener can be pre-attached to the mesh. The mesh can be attached to the outer tuber to provide access for cutting.

FIG. 31A illustrates a front view of the rotary cutting mechanism based delivery system depicted in FIGS. 29A-H in a second phase of operation. FIG. 31B illustrates a magnified sub-view of the bottom portion of the rotary cutting mechanism based delivery system depicted in FIG. 31A in a second phase of operation. As FIGS. 31A and 31B illustrate, in the second phase, the pusher tube can be advanced forward to secure the fastener.

Figure 32A:
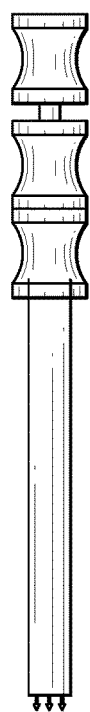
FIG. 32A illustrates a front view of the rotary cutting mechanism based delivery system depicted in FIGS. 29A-H in a third phase of operation in accordance with another exemplary embodiment of the disclosed subject matter.
Figure 32B:
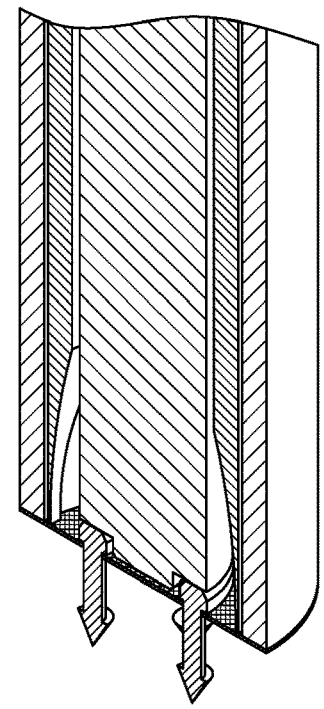
FIG. 32B illustrates a magnified sub-view of the bottom portion of the rotary cutting mechanism based delivery system depicted in FIG. 32A in a third phase of operation in accordance with an exemplary embodiment of the disclosed subject matter.

FIG. 32A illustrates a front view of the rotary cutting mechanism based delivery system depicted in FIGS. 29A-H in a third phase of operation. FIG. 32B illustrates a magnified sub-view of the bottom portion of the rotary cutting mechanism based delivery system depicted in FIG. 32A in a third phase of operation. As FIGS. 32A and 32B illustrate, in the third phase, the inner tube of the telescoping sheath can be advanced forward further and can be rotated to cut the mesh. The inner tube can be rotated using the knobs on the sheath either manually, mechanically, or according to an automated process.

Figure 33A:
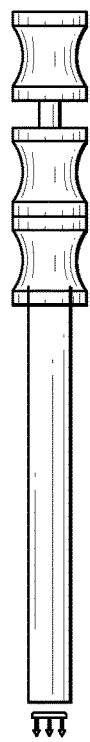
FIG. 33A illustrates a front view of the rotary cutting mechanism based delivery system depicted in FIGS. 29A-H in a fourth phase of operation in accordance with another exemplary embodiment of the disclosed subject matter.
Figure 33B:
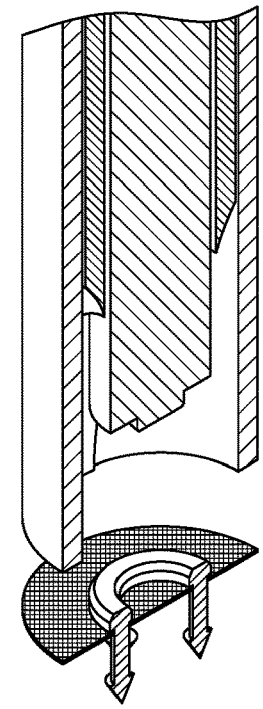
FIG. 33B illustrates a magnified sub-view of the bottom portion of the rotary cutting mechanism based delivery system depicted in FIG. 33A in a fourth phase of operation in accordance with an exemplary embodiment of the disclosed subject matter.

FIG. 33A illustrates a front view of the rotary cutting mechanism based delivery system depicted in FIGS. 29A-H in a fourth phase of operation. FIG. 33B illustrates a magnified sub-view of the bottom portion of the rotary cutting mechanism based delivery system depicted in FIG. 33A in a fourth phase of operation. As FIGS. 33A and 33B illustrate, in the fourth phase, the delivery system can be removed from the telescoping sheath. The mesh can be removed from the telescoping sheath by being withdrawn separately and/or integrally.

Figure 34A:
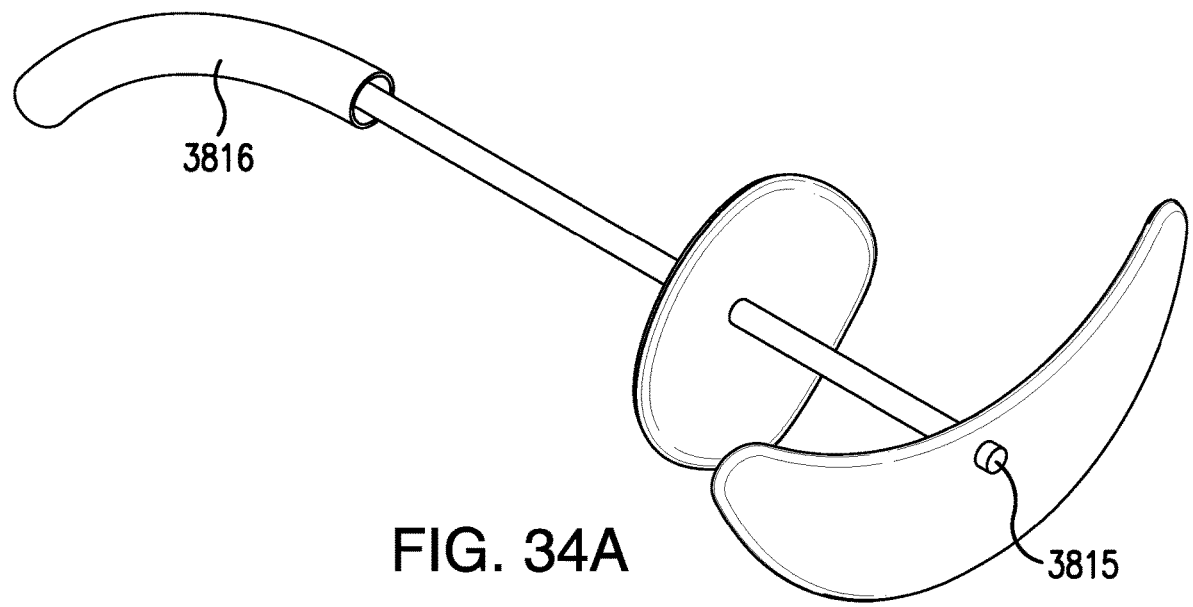
FIGS. 34A-G illustrate different views of an exemplary crescent member shaped telescoping laparoscopic mesh delivery system.
Figure 34B:
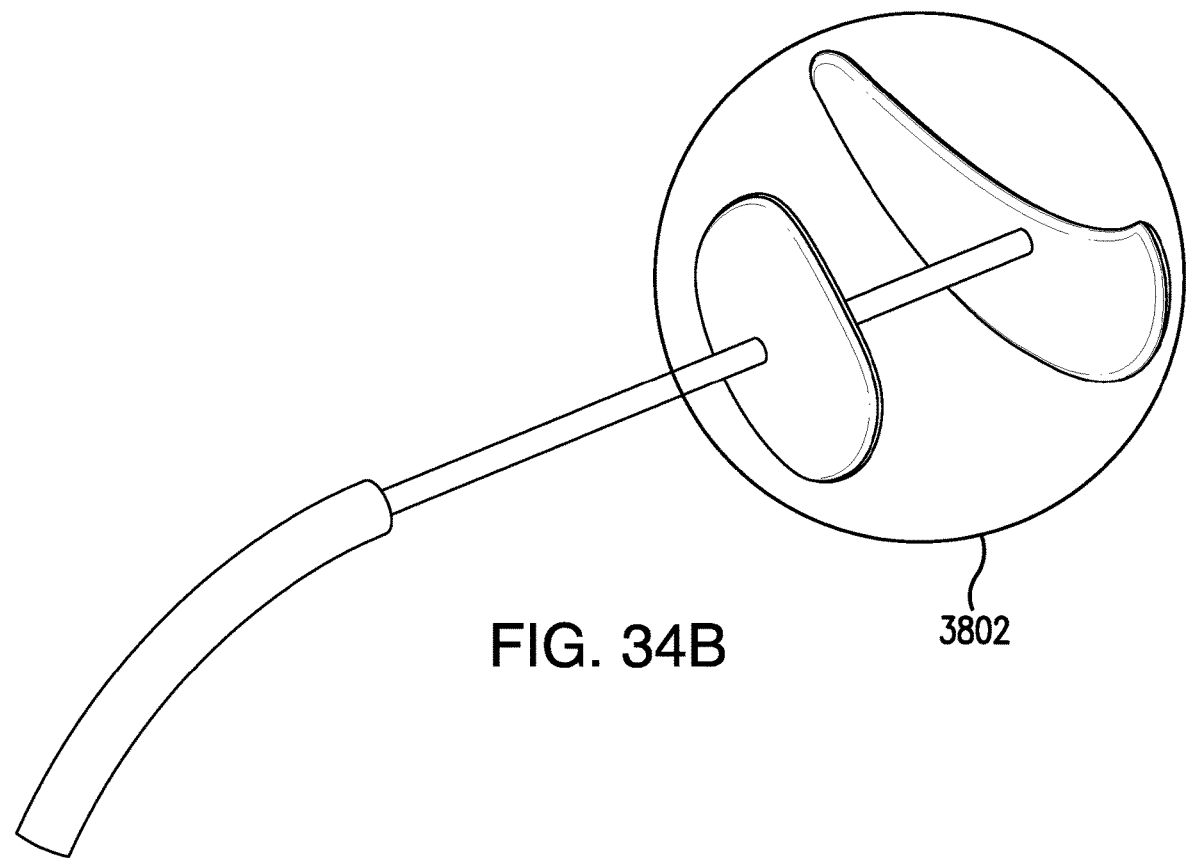
Figure 34C:
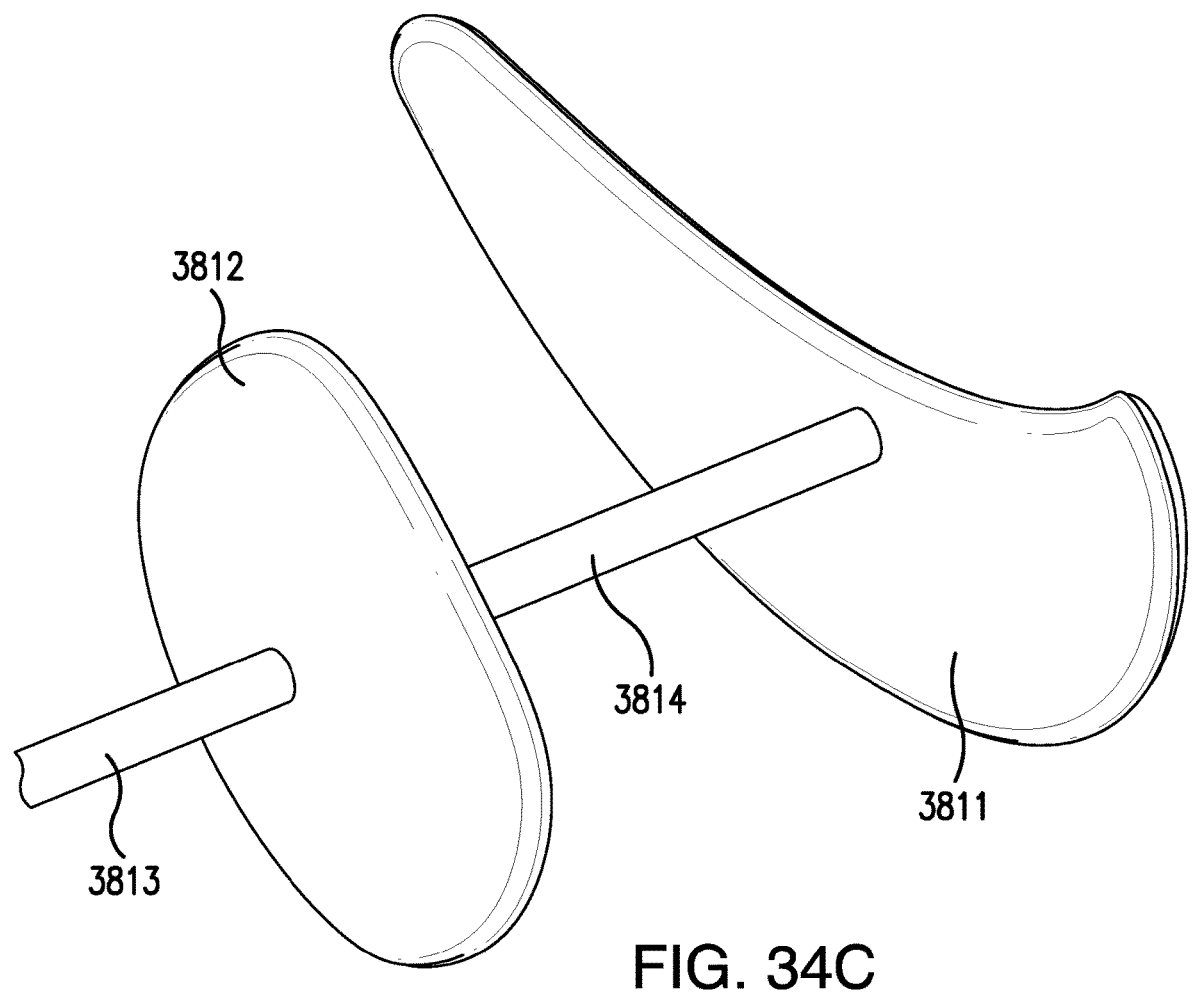

FIGS. 34A-G illustrate different views of an exemplary crescent member shaped telescoping laparoscopic mesh delivery system. FIG. 34C is an enlarged view of portion 3802 of FIG. 34B. The crescent member shaped telescoping laparoscopic mesh delivery system can include a distal closure member 3811 of the surgical mesh and a proximal closure member 3812 of the surgical mesh connected and/or coupled together by a closure member coupling 3814. The crescent member shaped telescoping laparoscopic mesh delivery system can include an introducer tip 3813. A guidewire 3817 can be inserted into the telescoping sheath at the guidewire location 3815. The introducer shaft 3816 can be used to deliver the distal closure member 3811 and the proximal closure member 3812 to the appropriate target location in the fascial tissue at which the distal closure member 3811 of the mesh and the proximal closure member 3812 of the mesh are to be deployed. The distal closure member 3811 and the proximal closure member 3812 can both be mesh portions that can be applied to opposite sides of the fascial tissue once the distal closure member 3811 and the proximal closure member 3812 are fully deployed and in contact with the fascial tissue.

In some embodiments, the proximal closure member 3812 can be attached to the top side of the fascia and the distal closure member 3811 can be attached to the underside of the fascia. The proximal closure member 3812 and the distal closure member 3811 can be opened from a pre-folded delivery configuration into a partially deployed configuration shown by pulling on the guidewire 3817.

Figure 34D:
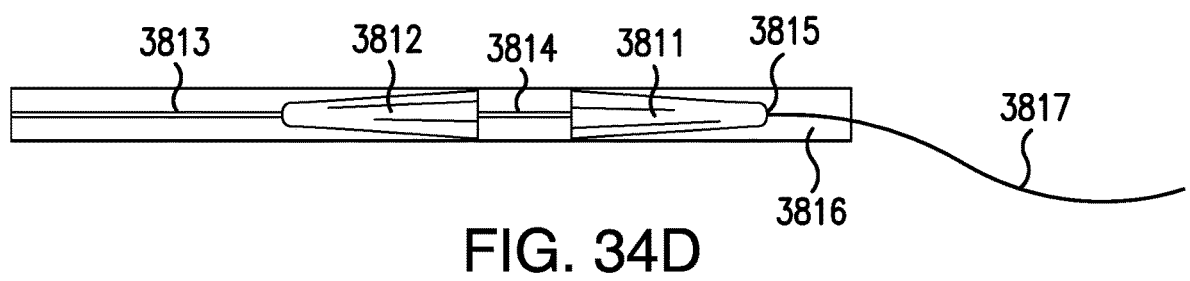
Figure 34E:
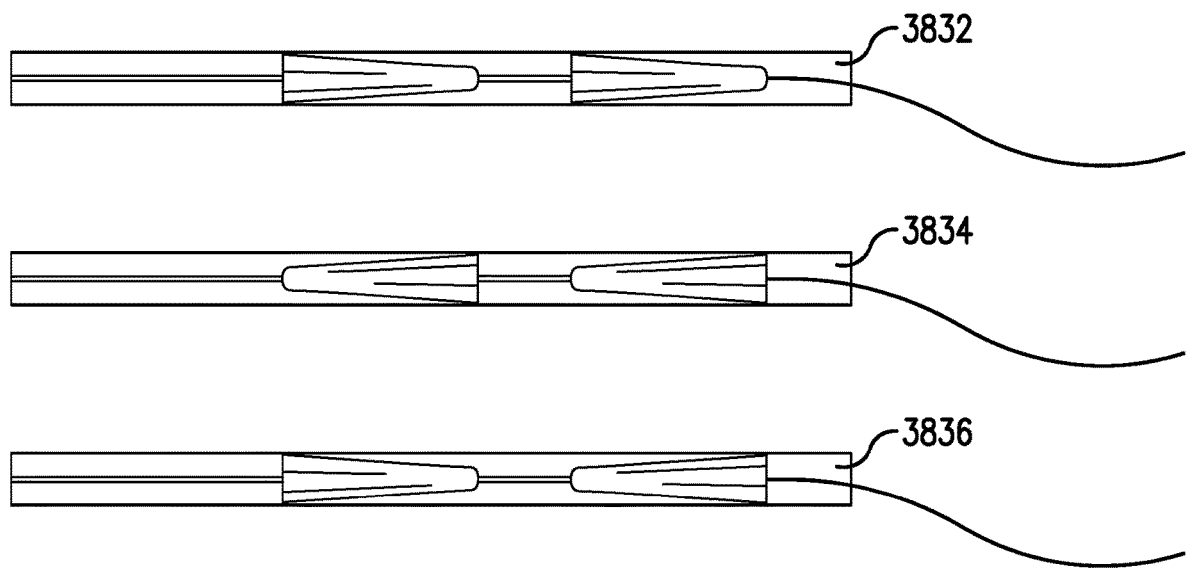
Figure 34F:
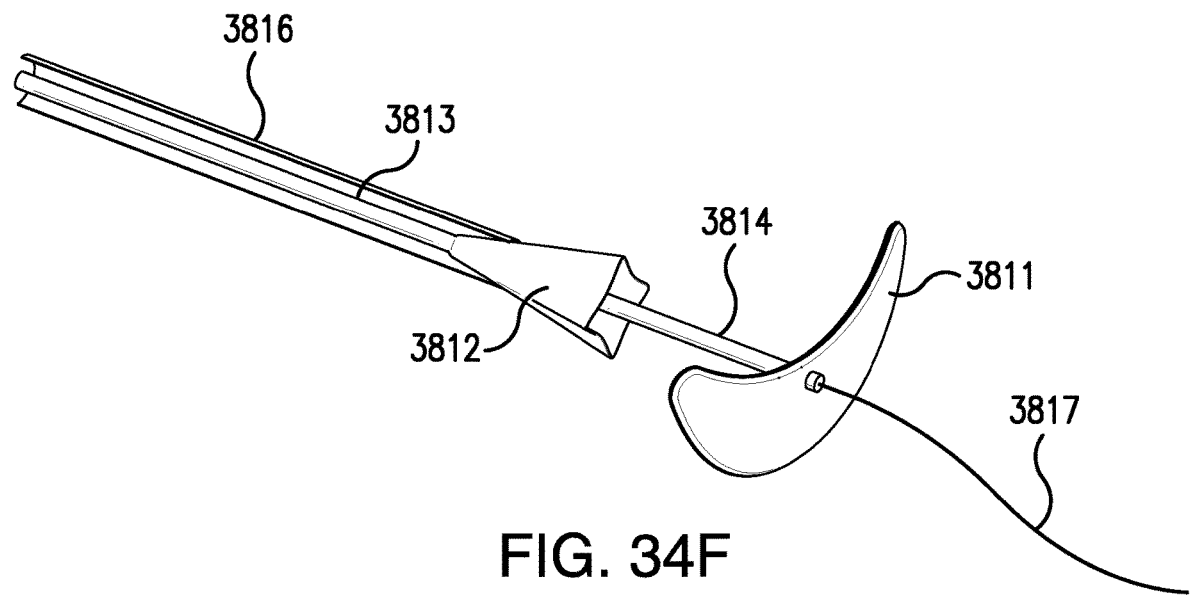
Figure 34G:
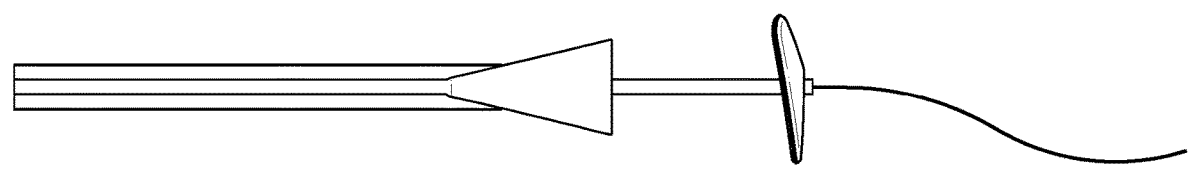

FIG. 34D is a side-view of the crescent member shaped telescoping laparoscopic mesh delivery system in a mesh delivery configuration. FIG. 34E illustrates alternate positions and/or configurations 3832, 3834, and 3836 of the distal closure member 3811 and proximal closure member 3812 during mesh delivery. FIGS. 34F and 34G illustrate different views of the crescent member shaped telescoping laparoscopic mesh delivery system in a partial deployment configuration in which the proximal closure member 3812 is not fully deployed but the distal closure member 3811 is deployed. In some embodiments, the crescent member shaped telescoping laparoscopic mesh delivery system can be in a partially deployed configuration once the guidewire 3817 pulls the distal closure member 3811 out of the introducer shaft 3816 from the mesh delivery configuration of FIG. 34D. In the partially deployed configuration, the guidewire 3817 can still be in the process of being pulled and, accordingly, the proximal closure member 3812 can still not be fully deployed as it is being extracted out of the introducer shaft 3816.

Figure 35A:
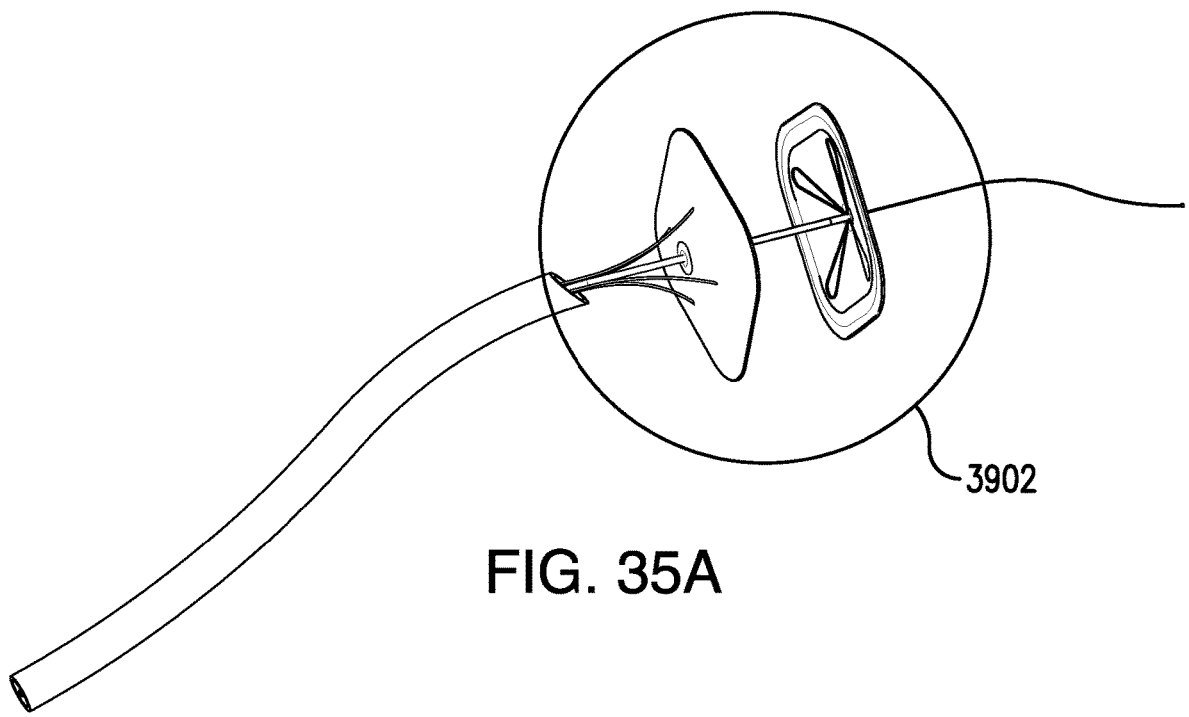
FIGS. 35A-I illustrate different views and embodiments of exemplary double member shaped telescoping laparoscopic mesh delivery system.
Figure 35B:
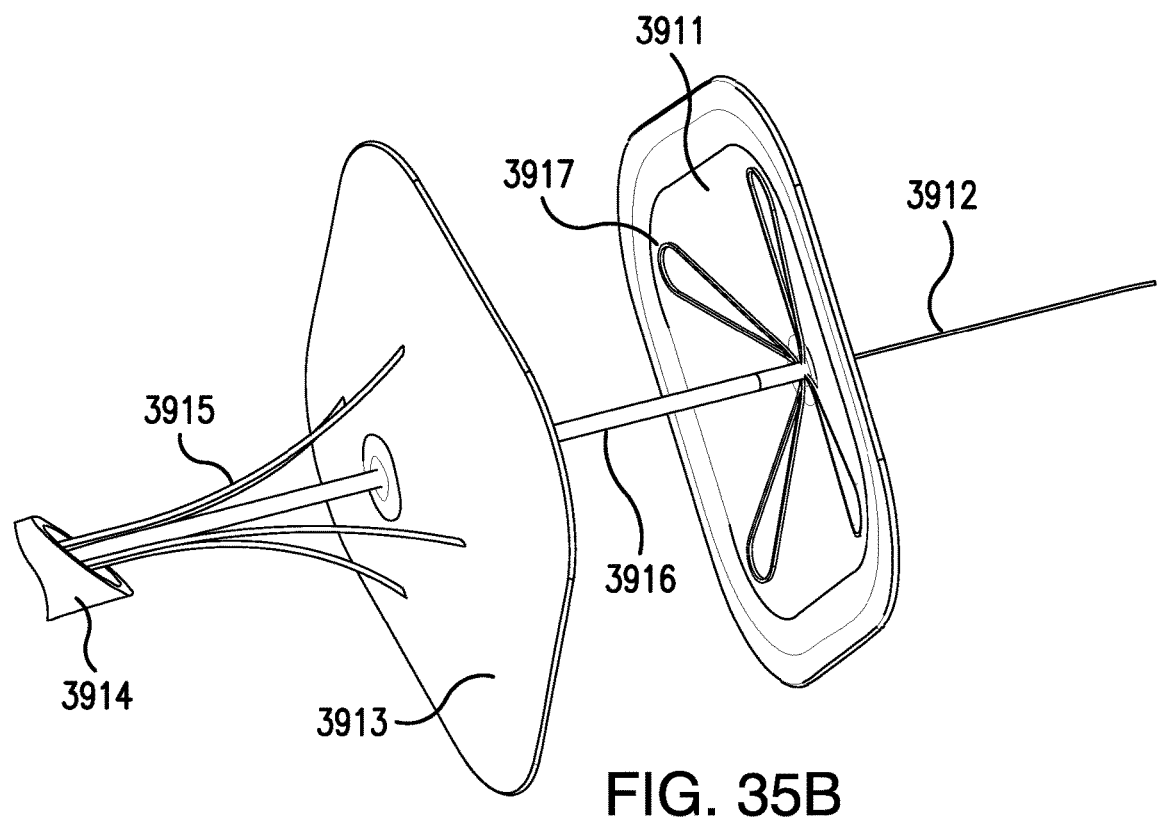
Figure 35C:
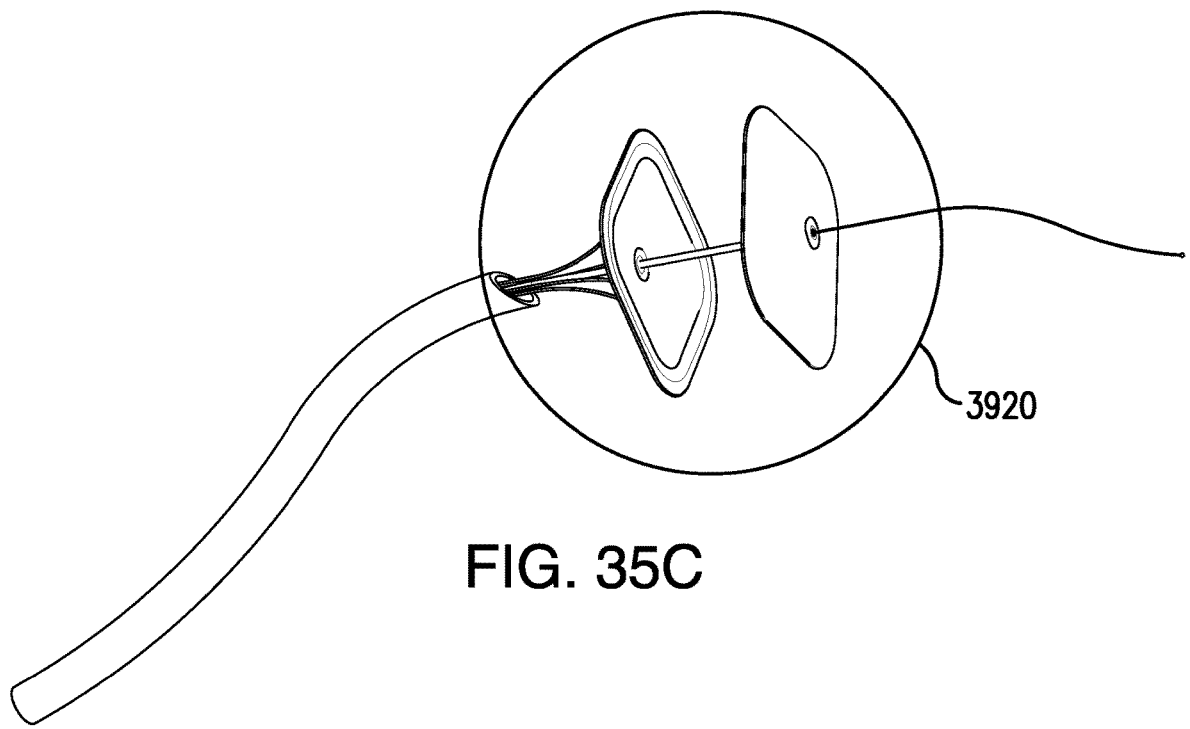
Figure 35D:
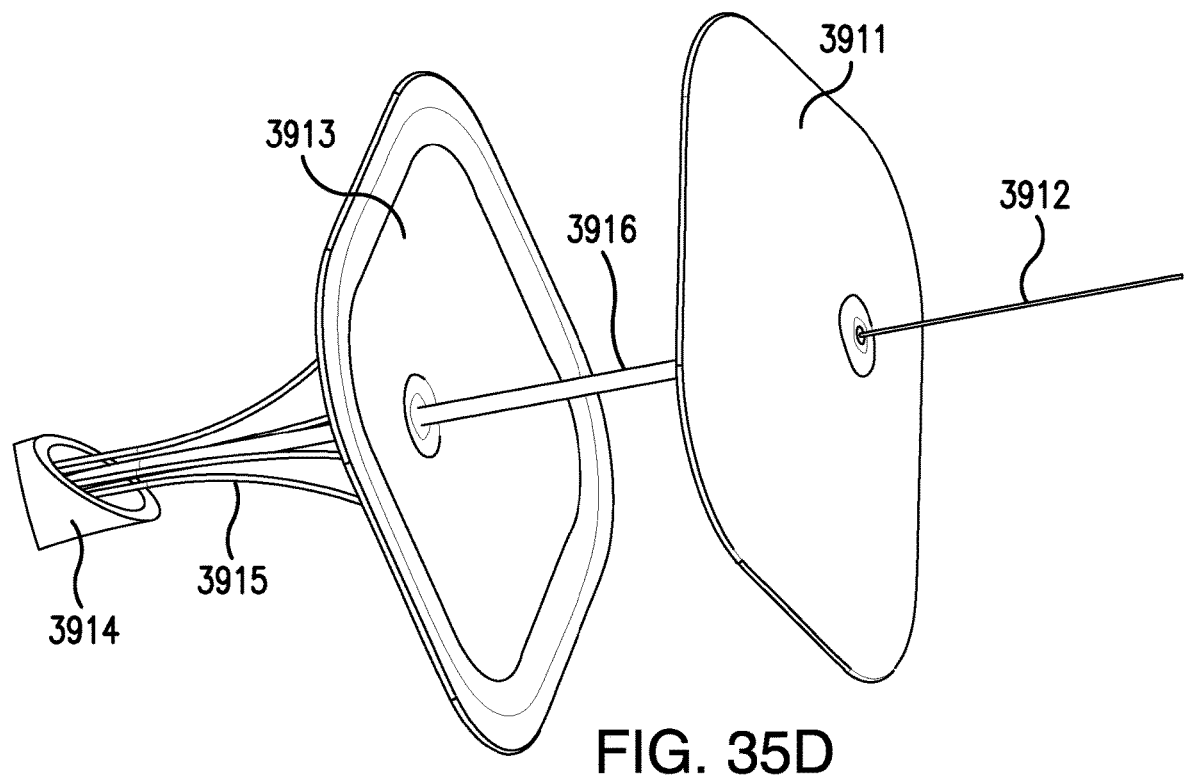
Figure 35E:
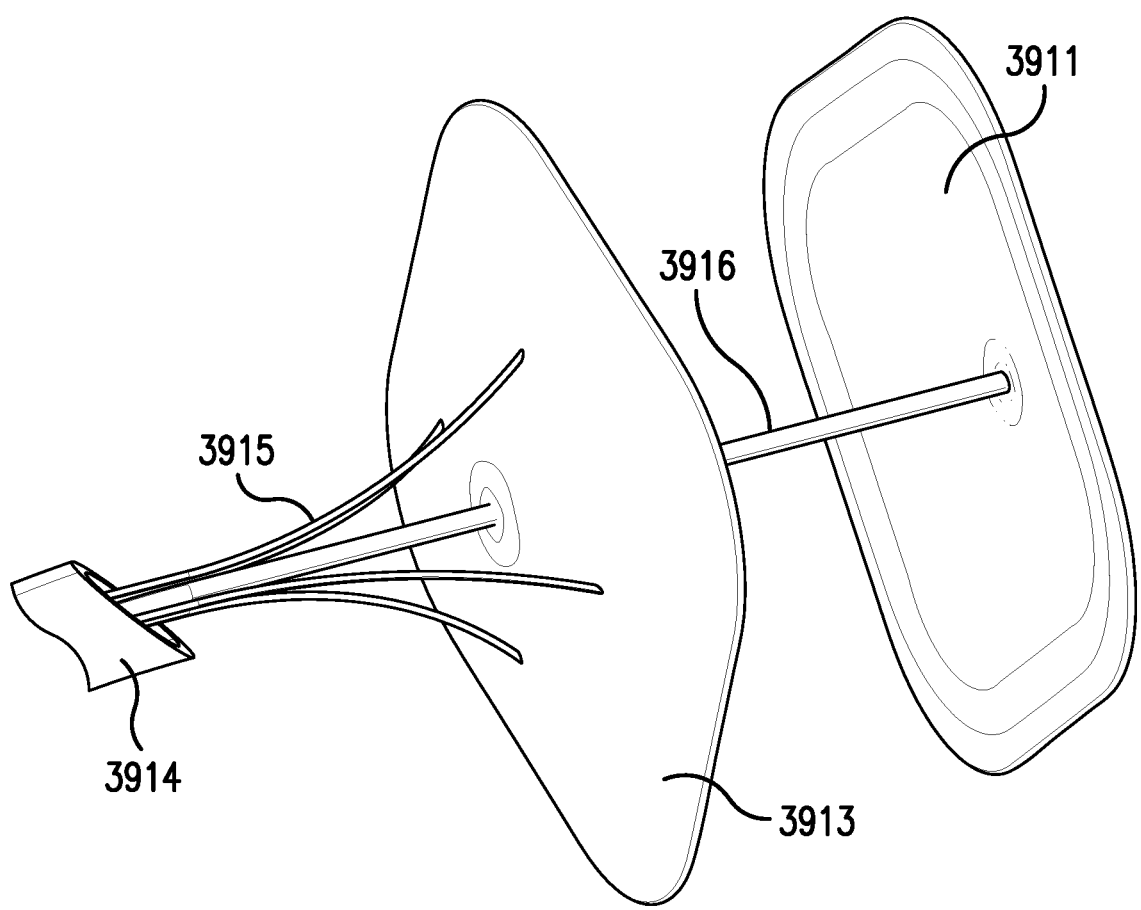

FIGS. 35A-I illustrate different views and embodiments of exemplary double member shaped telescoping laparoscopic mesh delivery system. FIG. 35B is an enlarged view of portion 3902 of FIG. 35A. FIG. 35D is an enlarged view of portion 3920 of FIG. 35C. FIGS. 35A and 35B show a different embodiment of the double member shaped telescoping laparoscopic mesh delivery system than the embodiment shown in FIGS. 35C and 35D. FIG. 35E illustrates a different embodiment of the double member shaped telescoping laparoscopic mesh delivery system than the embodiments shown in FIGS. 35A-35D.

For each of the embodiments illustrated in FIGS. 35A-H, the double member shaped telescoping laparoscopic mesh delivery system can include a distal closure member 3911 of a mesh and a proximal closure member 3913 of the mesh connected and/or coupled using a closure member coupling 3916. In some embodiments, the double member shaped telescoping laparoscopic mesh delivery system can include a guidewire 3912. The distal closure member 3911 and the proximal closure member 3913 can both be mesh portions that can be applied to opposite sides of the fascial tissue once the distal closure member 3811 and the proximal closure member 3913 are fully deployed and in contact with the fascial tissue. In some embodiments, the distal closure member 3911 can be applied to the underside of the fascial and the proximal closure member 3913 can be applied to the top side of the fascia.

In some embodiments, the introducer tip 3914 can be connected and/or coupled to the a proximal closure member 3913 using an external support and/or delivery structure 3915. As shown in FIG. 35B, the guidewire 3912 can fit inside the hollow closure member coupling 3916. The closure member coupling 3916 can be attached to the delivery structure 3915, which can be coupled to the introducer 3914.

In the embodiment illustrated in FIGS. 35A and 35B, the distal closure member 3911 can include an internal support structure 3917. In some embodiments, the internal support structure 3917 can be a spring wire that can be designed to help the distal closure member 3911 spring open from a delivery configuration to a fully deployed configuration once the distal closure member 3911 is at the appropriate target site of the fascial tissue to which it is to be attached. FIGS. 35-D illustrate an embodiment of the double member shaped telescoping laparoscopic mesh delivery system without such an internal support structure.

Figure 35F:
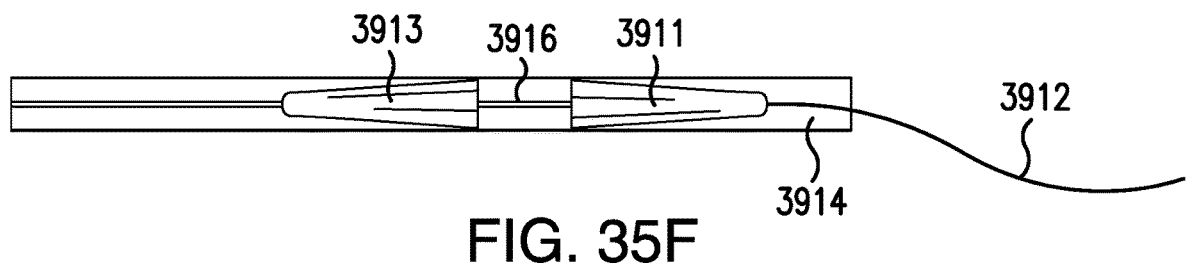

While FIGS. 35A-E illustrate views of the double member shaped telescoping laparoscopic mesh delivery system in a fully deployed configuration, FIG. 35F illustrates a side-view of the double member shaped telescoping laparoscopic mesh delivery system in a mesh delivery configuration. As illustrated in FIG. 35F, the distal closure member 3911 and the proximal closure member 3913 can be folded in a compressed shape inside the introducer 3914. In some embodiments, once the introducer 3914 is positioned at the appropriate portion of the fascia where the mesh is to be deployed, pulling the guidewire 3912 can release the distal closure member 3911 of the mesh and the proximal closure member 3913 of the mesh such that the distal closure member 3911 is on one side of the fascial tissue and the proximal closure member 3913 is on the other side of the fascial tissue. Both the distal closure member 3911 and the proximal closure member 3913 be affixed onto each side of the fascial tissue that they are each respectively in contact with, resulting in the fully deployed configuration of FIGS. 35A-E.

In some embodiments, the double member shaped telescoping laparoscopic mesh delivery system can be pre-folded into a collapsed state while being spring loaded in the delivery configuration. The distal closure member 3911 and the proximal closure member 3913 can be pre-folded around the closure member coupling 3916. The telescoping laparoscopic mesh delivery system can be in the folded delivery configuration when it is being delivered through the fascial incision instead of being in a fully deployed configuration during delivery to prevent the deployed mesh from interfering with the fascia and getting stuck in the fascial incision and/or widening the fascial incision. In some embodiments, the telescoping laparoscopic mesh delivery system can be inserted laparoscopically (e.g., the telescoping laparoscopic mesh delivery system can be folded and wound around the closure member coupling 3916) while the mesh delivery system is being delivered through the fascial incision so that the distal closure member 3911 and the proximal closure member 3913 can be on opposite sides of the fascia.

In some embodiments, during delivery of the telescoping laparoscopic mesh delivery system to the target location on the fascia, the introducer 3914 can be oriented such that it faces the abdoment and/or fascia and can be pushed until it is located on the distal end of the fascia. The guidewire 3912 can be pulled such that the closure member coupling 3916 is pulled through the hole in the hole in the proximal closure member 3913. In some embodiments, the closure member coupling 3916 can detach upon withdrawal.

In some embodiments, pulling on the guidewire 3912 can cause the umbrella shaped pre-folded mesh (e.g, distal closure member 3911 and the proximal closure member 3913 in the delivery configuration) to spring open into a partially deployed configuration and then into a fully deployed configuration. Once the distal closure member 3911 is affixed onto the inside of the fascia, by pushing on closure member coupling 3916 and having the distal closure member 3911 open up from its pre-folded configuration into a deployed shape, the guidewire 3912 can be further pulled so that the proximal closure member 3913 is opened from its folded configuration in the partially deployed configuration and attached to the top side of the fascia, resulting in the fully deployed configuration. In some embodiments, the guidewire 3912 can be flexible. In other embodiments, the guidewire 3912 can be rigid.

In some embodiments, the spring loaded characteristics of the double member shaped telescoping laparoscopic mesh delivery system can be activated passively instead of actively activating it by pulling the guidewire 3912. For example, by pushing on the hollow closure member coupling 3916, the double member shaped telescoping laparoscopic mesh delivery system can be opened into a fully deployed configuration.

Figure 35G:
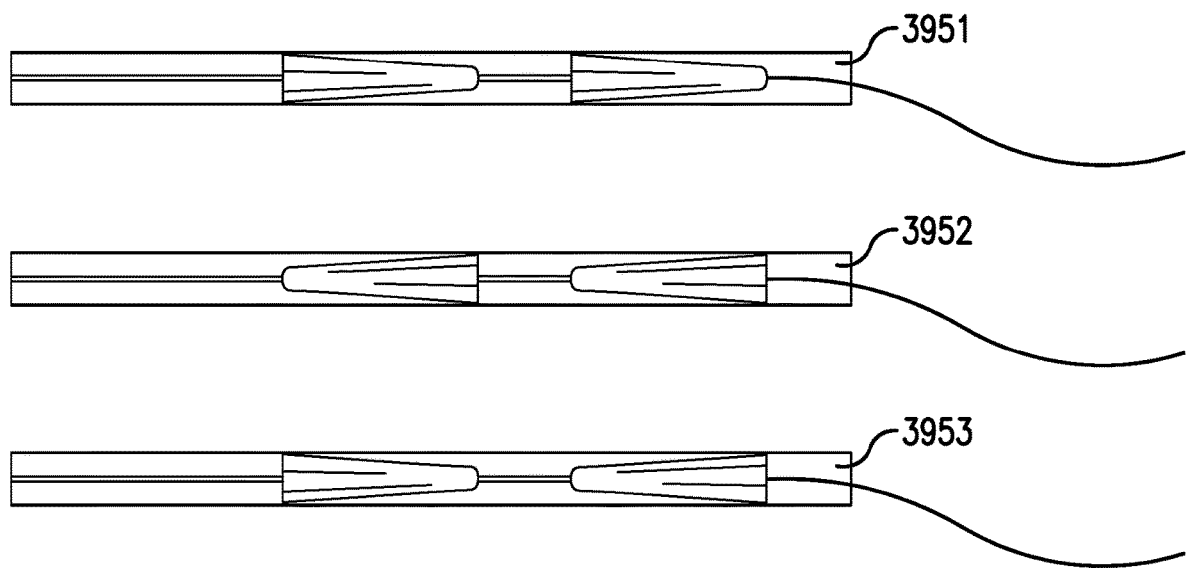

FIG. 35G illustrates alternate positions and/or configurations 3951, 3952, and 3953 of the distal closure member and proximal closure member during mesh delivery. As shown in configurations 3951, 3952, and 3953, the distal closure member 3911 and the proximal closure member 3913 can be in various different orientations with respect to each other and the fascial tissue (e.g., facing each other, facing opposite each other, facing the target tissue, facing away from the target tissue, etc.).

Figure 35H:
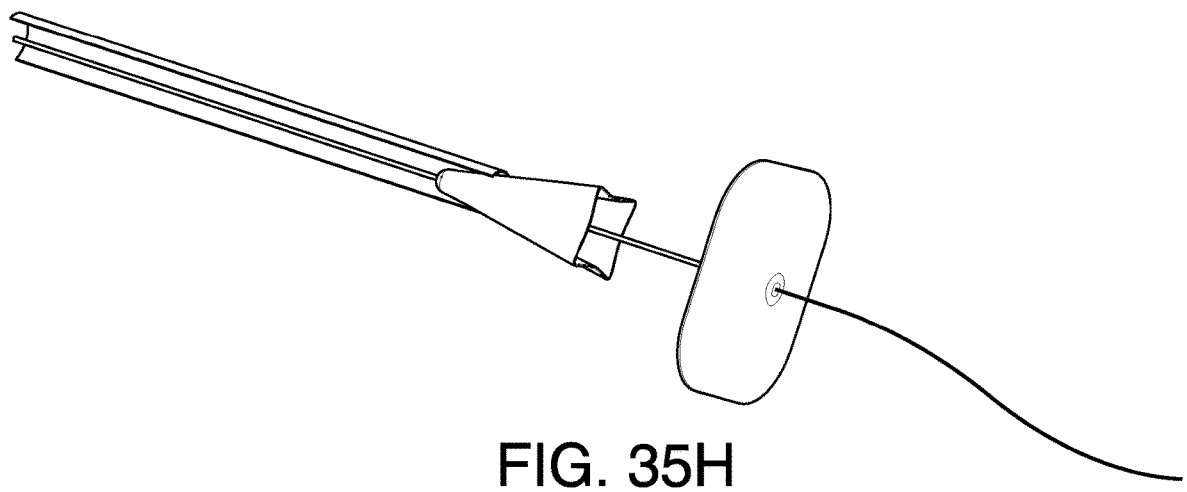
Figure 35I:
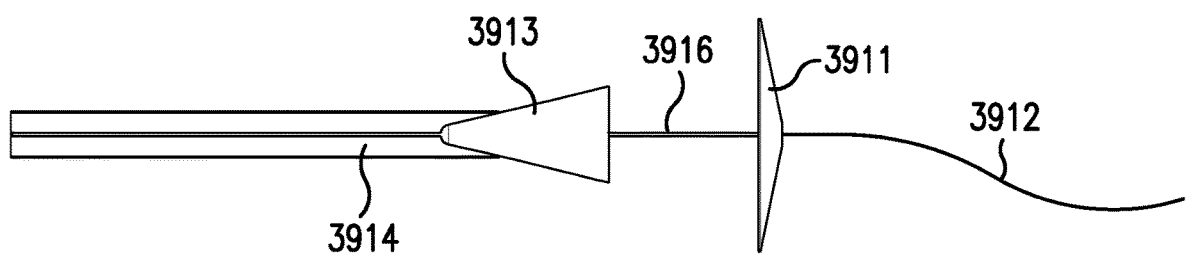

FIGS. 35H and 35I illustrate different side views of the double member shaped telescoping laparoscopic mesh delivery system in a partially deployed configuration with the internal support structure and guidewire 3912 shown. The partially deployed configuration can occur when the guidewire 3912 is being pulled (e.g., when the telescoping laparoscopic mesh delivery system is at the desired location with respect to the fascial incision it is to apply the mesh to) once the telescoping laparoscopic mesh delivery system is in a delivery configuration as shown in FIG. 35F. As shown in FIG. 35I, the distal closure member 3911 can be fully deployed once the guidewire is pulled while the proximal closure member 3913 can still not be deployed in this partially deployed configuration.

FIG. 36A-F illustrate different views of an exemplary expanded wire coil telescoping laparoscopic mesh delivery system. The expanded wire coil telescoping laparoscopic mesh delivery system can include a distal closure member 4021 and a proximal closure member 4022 that can be connected and/or coupled with a closure member coupling 4024, The expanded wire coil telescoping laparoscopic mesh delivery system can also include an introducer shaft 4023. In some embodiments, the expanded wire coil telescoping laparoscopic mesh delivery system can be comprised of a single mesh member unlike the double member shaped telescoping laparoscopic mesh delivery system of FIG. 35 and the crescent member shaped telescoping laparoscopic mesh delivery system of FIG. 34. For example, the proximal closure member 4022 and the distal closure member 4021 can be part of the same mesh. The mesh used in the expanded wire coil telescoping laparoscopic mesh delivery system can have a different structure and/or composition than that of the mesh used in the double member shaped telescoping laparoscopic mesh delivery system of FIG. 35 and the crescent member shaped telescoping laparoscopic mesh delivery system of FIG. 34. For example, the expanded wire coil mesh can be a tubular mesh braid.

Figure 36A:
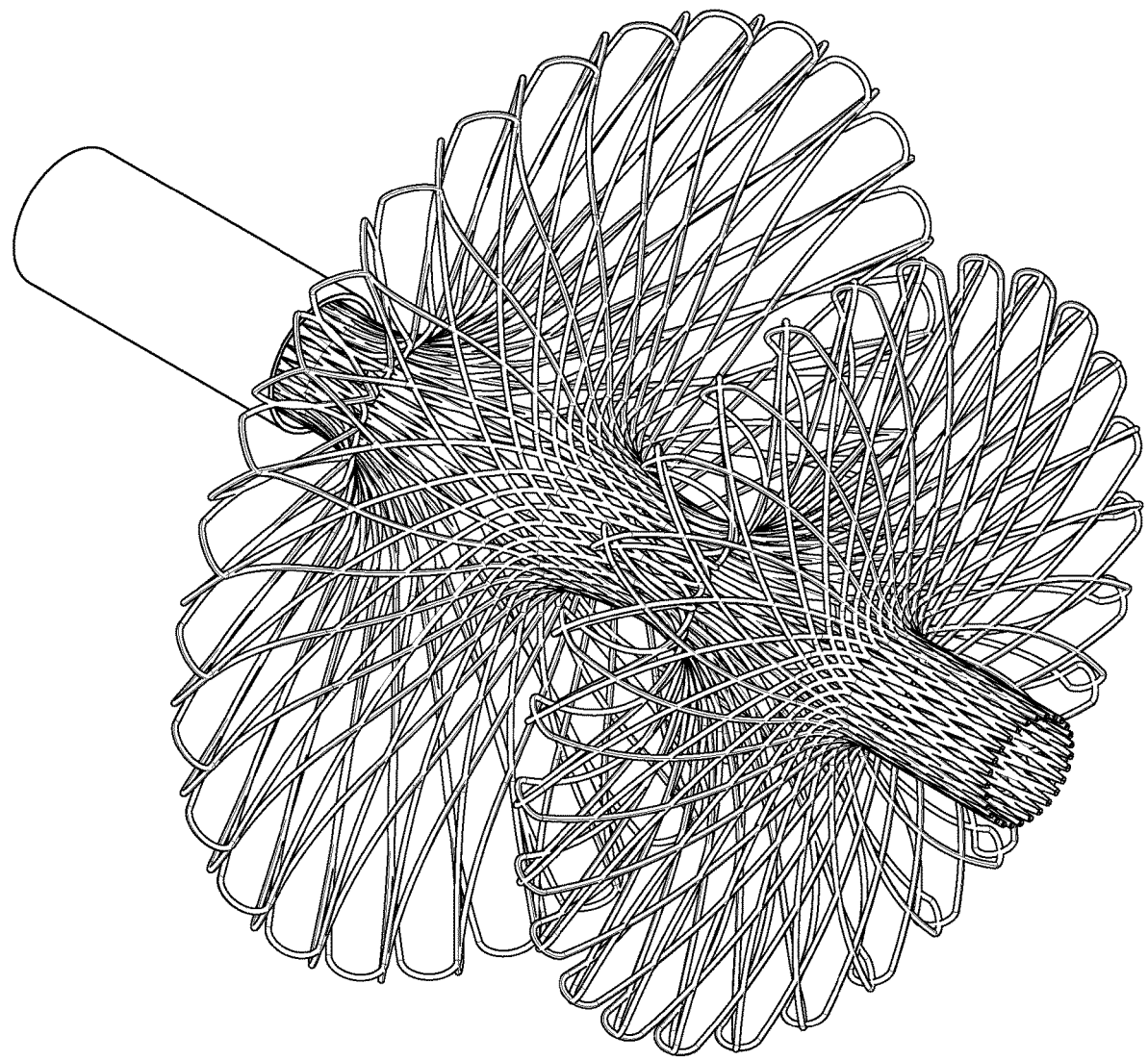
FIG. 36A-F illustrate different views of an exemplary expanded wire coil telescoping laparoscopic mesh delivery system.
Figure 36B:
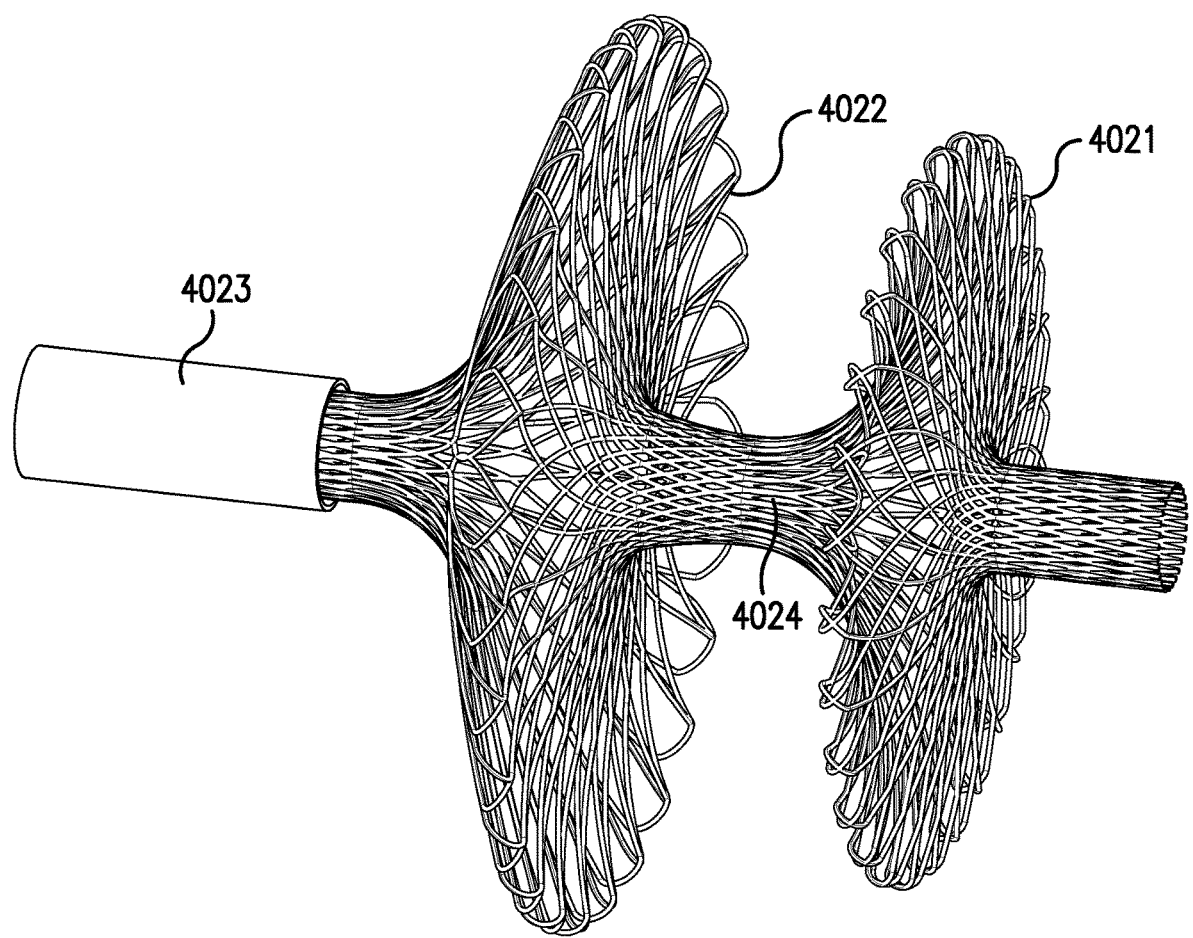
Figure 36C:
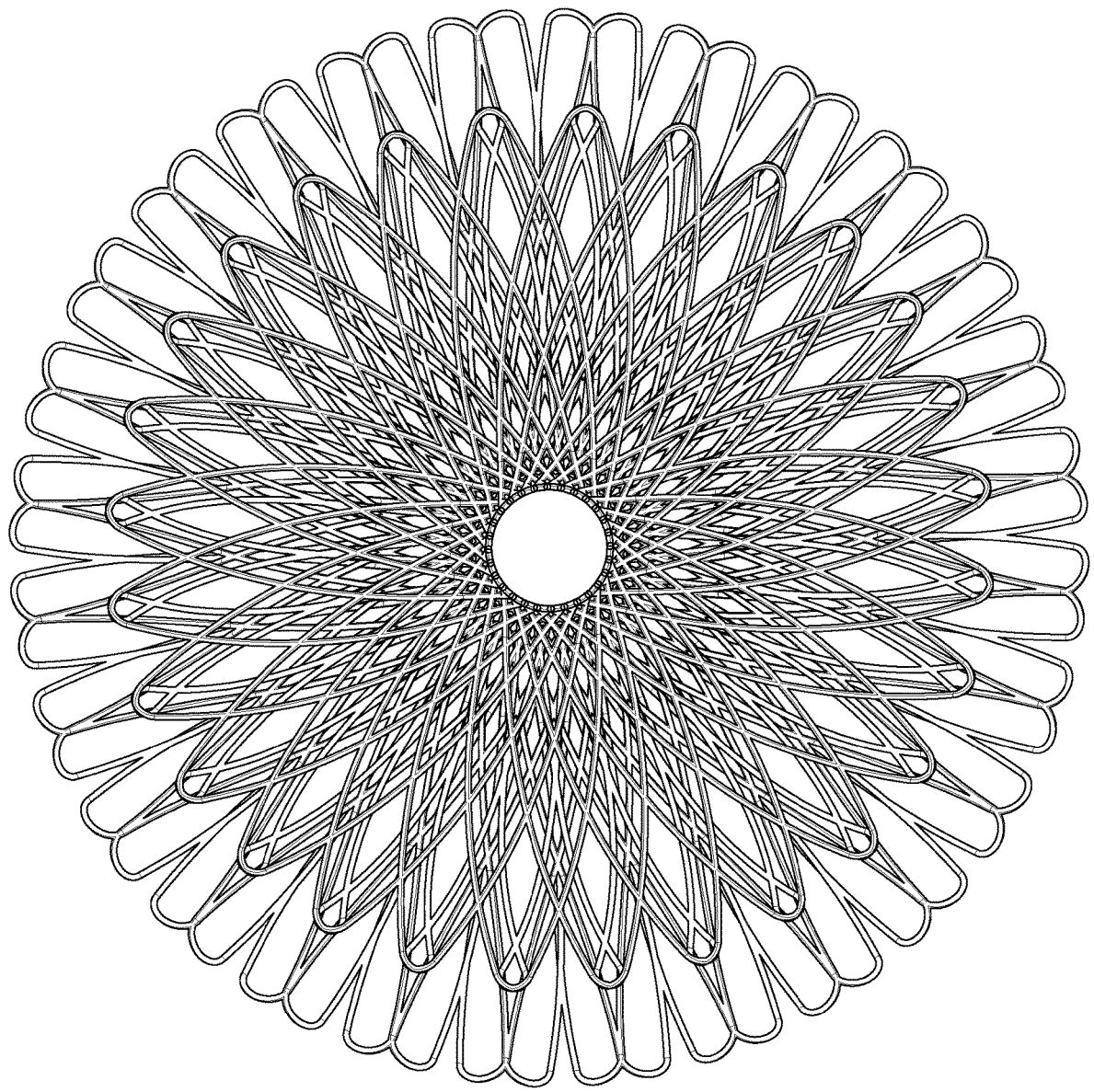
Figure 36D:
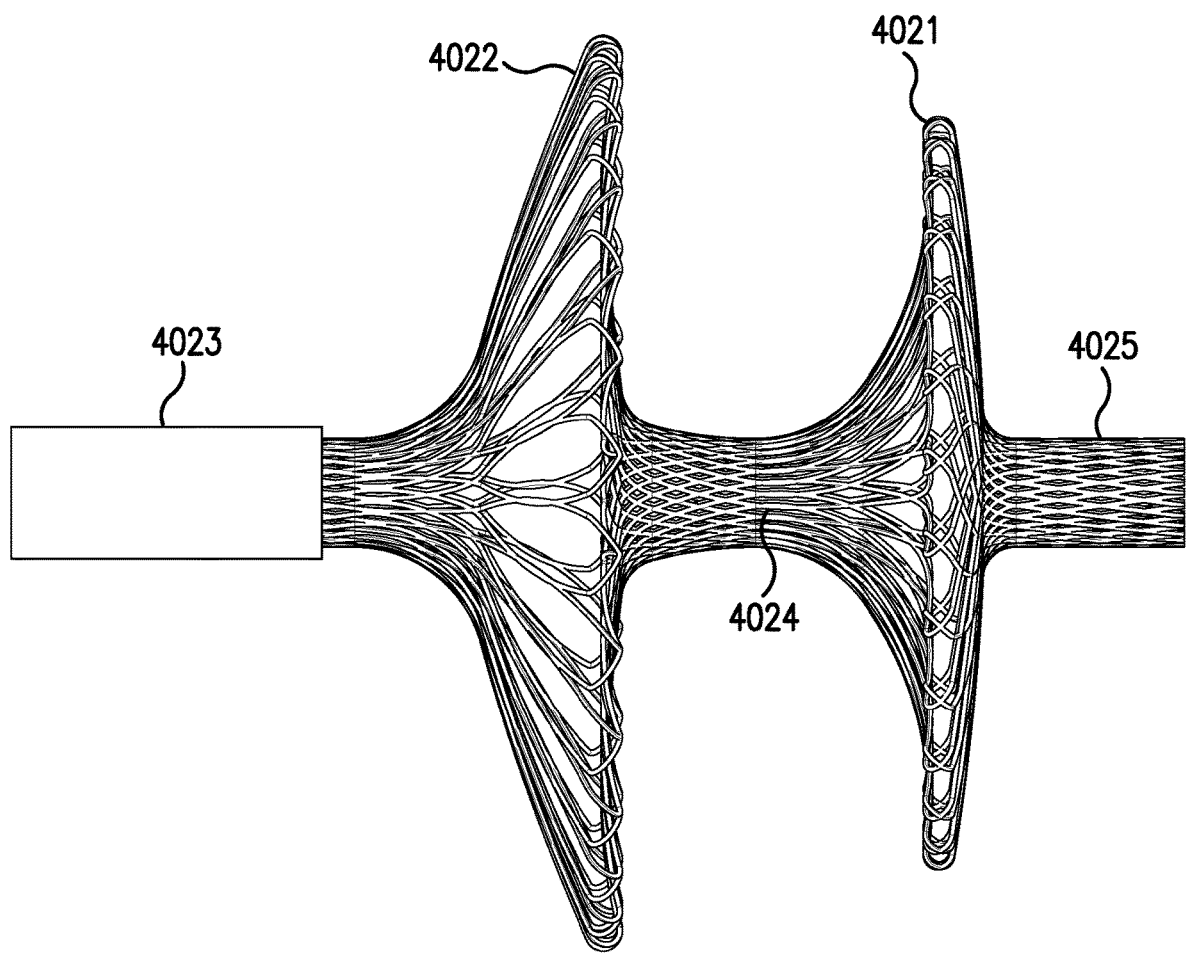
Figure 36E:
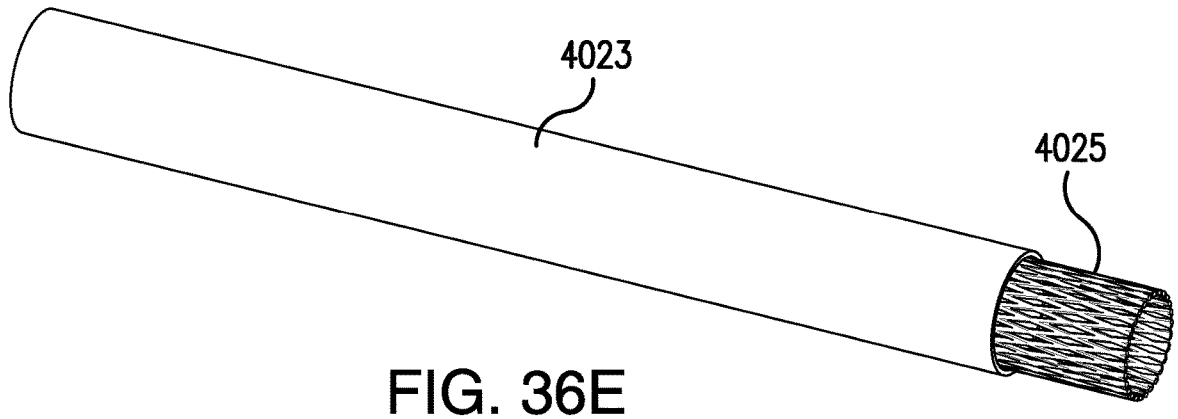
Figure 36F:
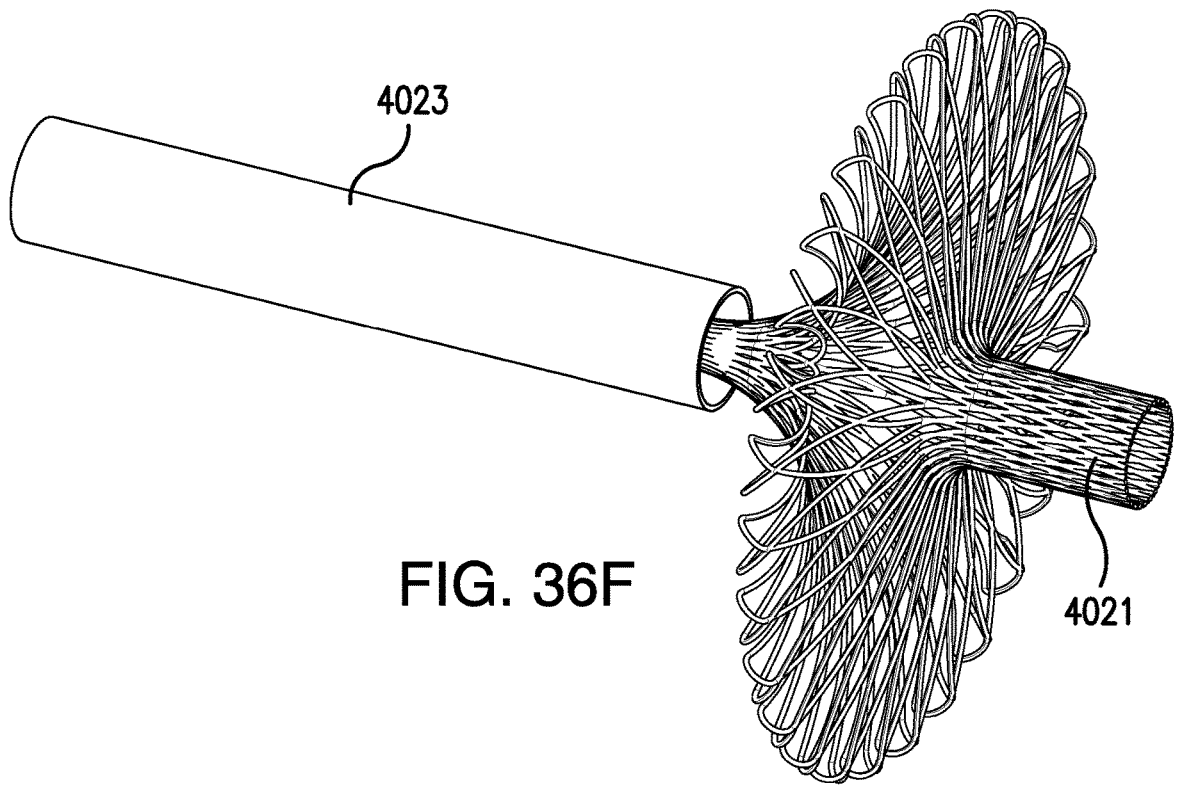

In some embodiments, the proximal closure member 4022 can be attached to the top side of the fascia and the distal closure member 4021 can be attached to the underside of the fascia. The proximal closure member 4022 and the distal closure member 4021 can be opened from a pre-folded delivery configuration as shown in FIG. 36E into a partially deployed configuration shown in FIG. 36F by pulling on the tip 4025 of the mesh. As illustrated in FIG. 36E, the mesh can be folded into a cylindrical shape in the delivery configuration and can be contained within the hollow introducer shaft 4023. Once the expanded wire coil telescoping laparoscopic mesh delivery system is at the target mesh delivery site (e.g., the fascial incision), the tip 4025 can be pulled so that the distal closure member 4021 can expand from its folded cylindrical shape to its deployed shape as shown in partially deployed view of FIG. 36F. Once the tip 4025 is further pulled, the proximal closure member 4022 can be withdrawn from the introducer shaft 4023 to be in a fully deployed configuration as shown in FIGS. 36A-D. In some embodiments, the expanded wire coil telescoping laparoscopic mesh delivery system can be opened from a delivery configuration to a fully deployed configuration (via the partially deployed configuration) in a single action (e.g., by pulling on the tip 4025) instead of the deployment stages being segmented into multiple different steps.

Figure 37A:
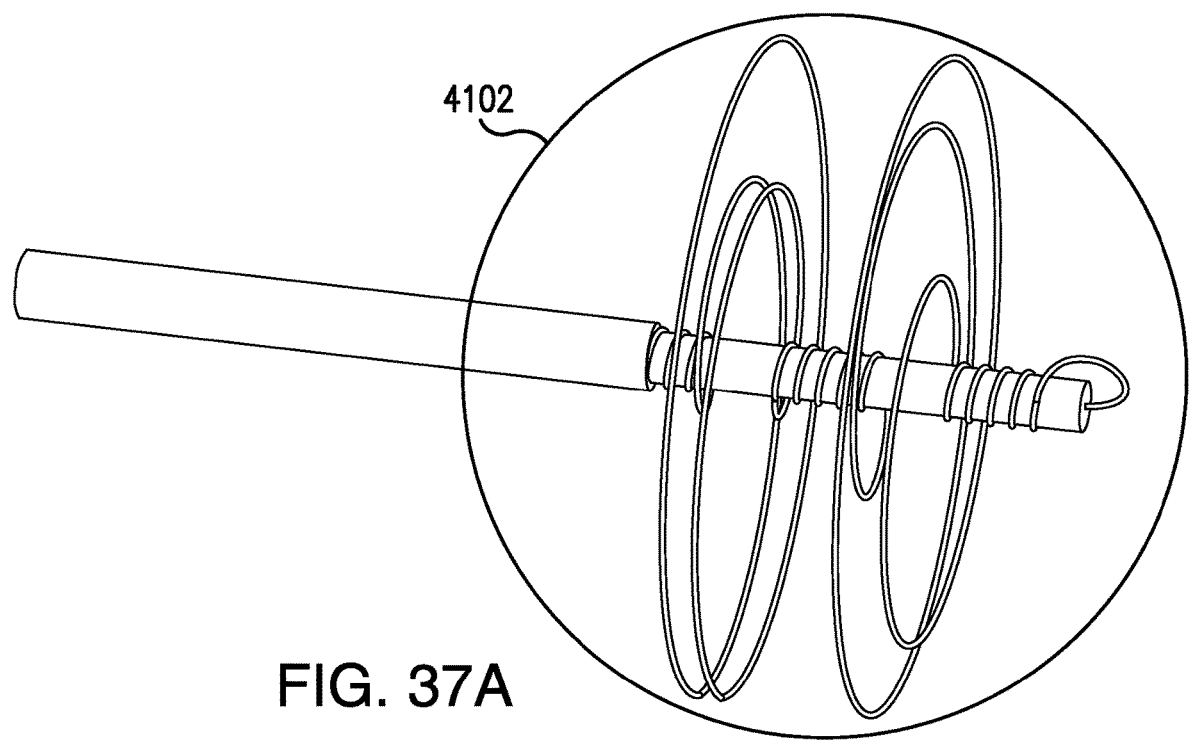
FIGS. 37A-E illustrate different views of an exemplary helex shaped telescoping laparoscopic mesh delivery system.
Figure 37B:
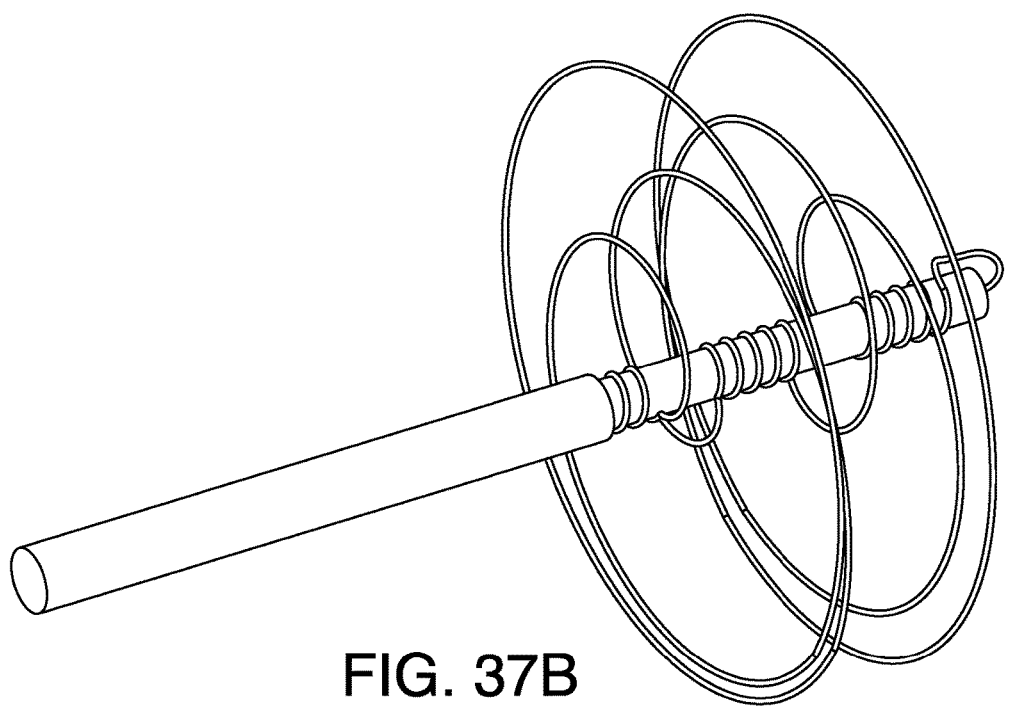

FIGS. 37A-E illustrate different views of an exemplary helex shaped telescoping laparoscopic mesh delivery system. FIG. 37B is an enlarged view of portion 4102 of FIG. 37A. The helex shaped telescoping laparoscopic mesh delivery system can include a distal closure member 4111 of the surgical mesh and a proximal closure member 4112 of the surgical mesh. Although the distal disclosure closure member 4111 and proximal closure member 4112 of FIGS. 37A-E do not show a mesh added onto the helex support structure underneath, any mesh can be applied onto the helical supporting arms of the distal disclosure closure member 4111 and proximal closure member 4112 shown in FIGS. 37A-E. In some embodiments, the mesh, which is applied onto the helex support structure shown in FIGS. 37A-E of the helex shaped telescoping laparoscopic mesh delivery system, can be rolled onto the surface of the fascial tissue surface.

In some embodiments, unlike the expanded wire coil telescoping laparoscopic mesh delivery system of FIG. 36, the double member shaped telescoping laparoscopic mesh delivery system of FIG. 35, and the crescent member shaped telescoping laparoscopic mesh delivery system of FIG. 34, the helex shaped telescoping laparoscopic mesh delivery system can be used without a mesh. For example, the distal disclosure closure member 4111 and proximal closure member 4112 can be any type of active closure devices (e.g., hooks), lithographically printed fixation device, a barb absorbable tack, etc.

In some embodiments, the helex member shaped telescoping laparoscopic mesh delivery system can include a receding introducer shaft 4113. The helex shaped telescoping laparoscopic mesh delivery system can also include a removable support substrate 4114.

Figure 37C:
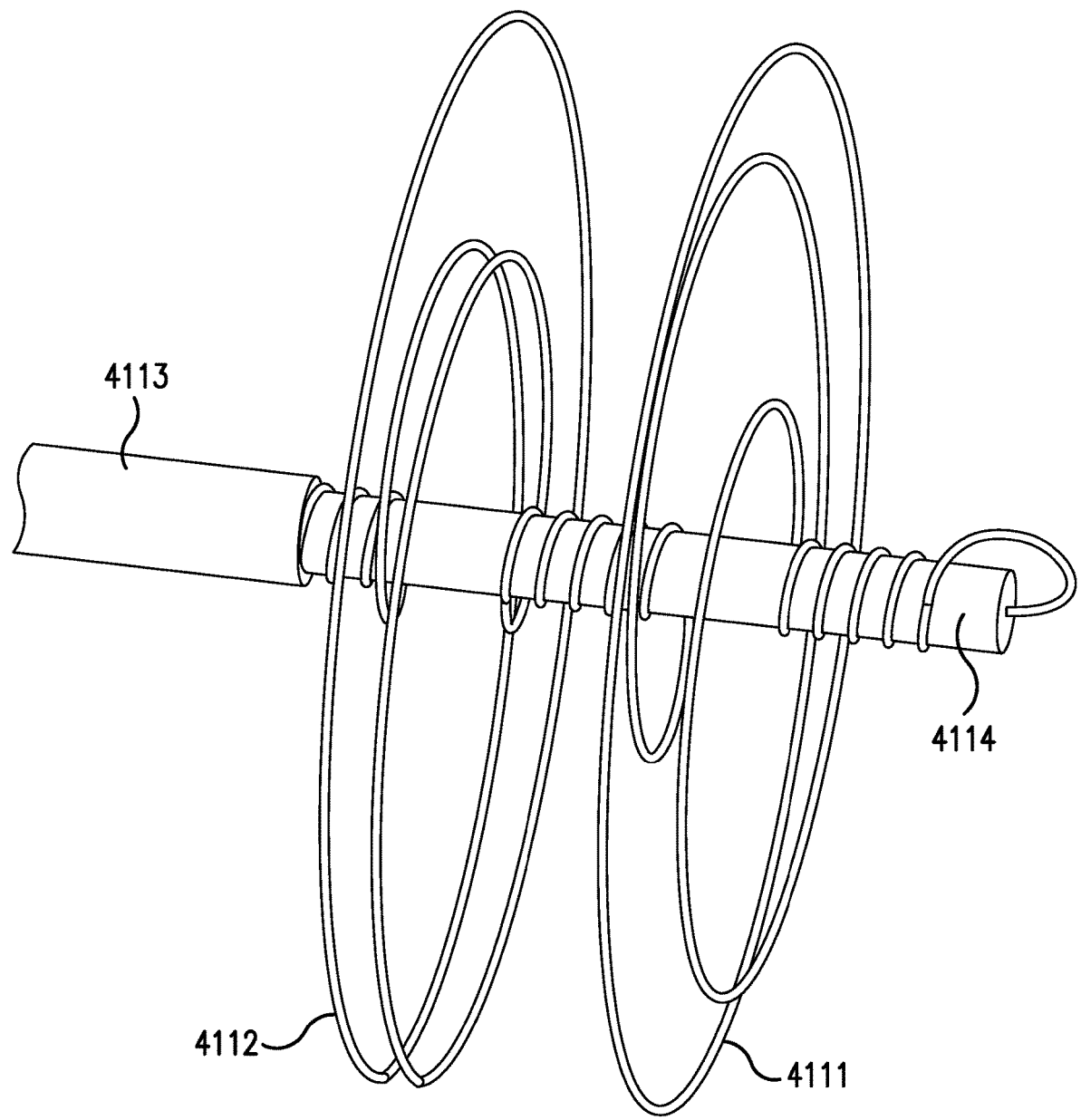
Figure 37D:
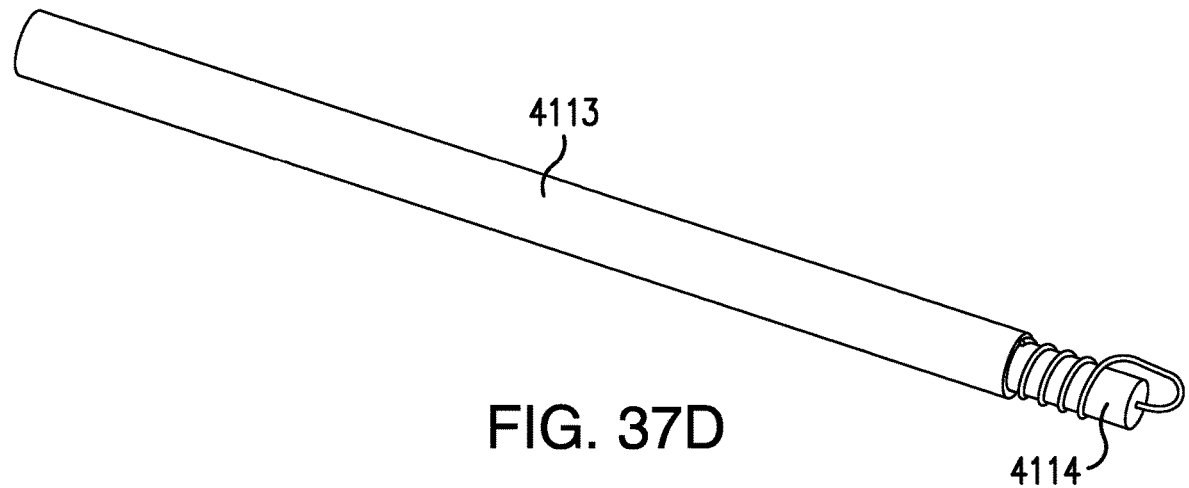
Figure 37E:
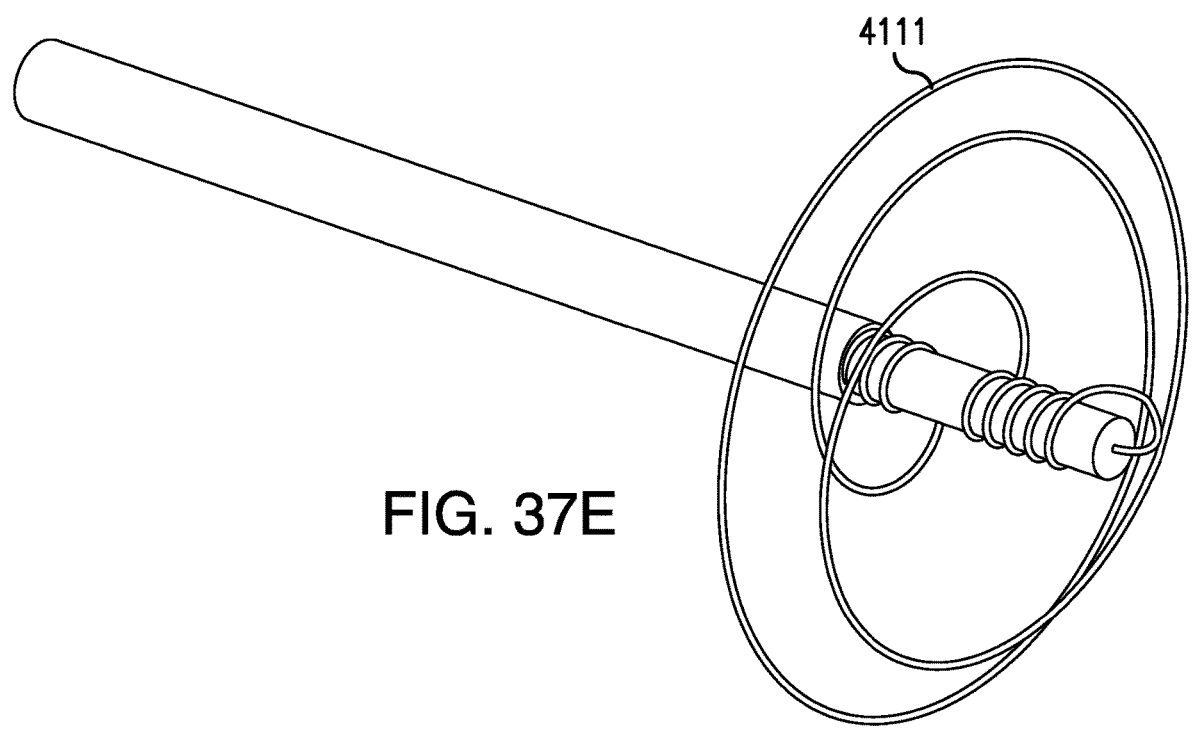

In some embodiments, the proximal closure member 4112 can be attached to the top side of the fascia and the distal closure member 4111 can be attached to the underside of the fascia. The proximal closure member 4112 and the distal closure member 4111 can be opened from a pre-folded delivery configuration as shown in FIG. 37D into a partially deployed configuration shown in FIG. 37E by pulling on the removable support substrate 4114. As illustrated in FIG. 37E, the helex can be folded into a cylindrical shape and/or wound around the removable support substrate 4114 in the delivery configuration and can be contained within the hollow receding introducer shaft 4113. Once the helex shaped telescoping laparoscopic mesh delivery system is at the target mesh delivery site (e.g., the fascial incision), the removable support substrate 4114 can be pulled so that the distal closure member 4111 can expand from its folded shape to its deployed shape as shown in partially deployed view of FIG. 37E. Once the removable support substrate 4114 is further pulled, the proximal closure member 4112 can be withdrawn from the receding introducer shaft 4023 to be in a fully deployed configuration as shown in FIGS. 37A-C.

FIGS. 38A-D illustrate different views of an exemplary offset ellipses shaped telescoping laparoscopic mesh delivery system. The offset ellipses shaped telescoping laparoscopic mesh delivery system can operate in similar fashion to either the the double member shaped telescoping laparoscopic mesh delivery system of FIG. 35 and/or the crescent member shaped telescoping laparoscopic mesh delivery system of FIG. 34, For example, the offset ellipses shaped telescoping laparoscopic mesh delivery system can include a distal closure member 4211 and a proximal closure member 4212 connected and/or coupled together by a closure member coupling 4215. The offset ellipses shaped telescoping laparoscopic mesh delivery system can include an introducer tip 4213, which can be surrounded by an introducer shaft 4214. A guidewire 4217 can be inserted into the telescoping sheath at the guidewire location 4216. The introducer shaft 4214 can be used to deliver the distal closure member 4211 and the proximal closure member 3812 to the appropriate target location in the fascial tissue at which the distal closure member 4211 of the mesh and the proximal closure member 4212 of the mesh are to be deployed. The distal closure member 4211 and the proximal closure member 3812 can both be mesh portions that can be applied to opposite sides of the fascial tissue once the distal closure member 4211 and the proximal closure member 4212 are fully deployed and in contact with the fascial tissue.

Unlike the double member shaped telescoping laparoscopic mesh delivery system of FIG. 35 and/or the crescent member shaped telescoping laparoscopic mesh delivery system of FIG. 34, the offset ellipses shaped telescoping laparoscopic mesh delivery system's distal closure member 4211 and a proximal closure member 4212 can be elliptical in shape and can be connected to the closure member coupling 4215, introducer tip 4213, and introducer shaft 4214 at location that is off-center from a center of the distal closure member 4211 and a proximal closure member 4212. Furthermore, the distal closure member 4211 and a proximal closure member 4212 can be oriented with respect to each other with a tilt angle (e.g., distal closure member 4211 and a proximal closure member 4212 can be aligned at a tilt to not be parallel to each other).

Figure 38A:
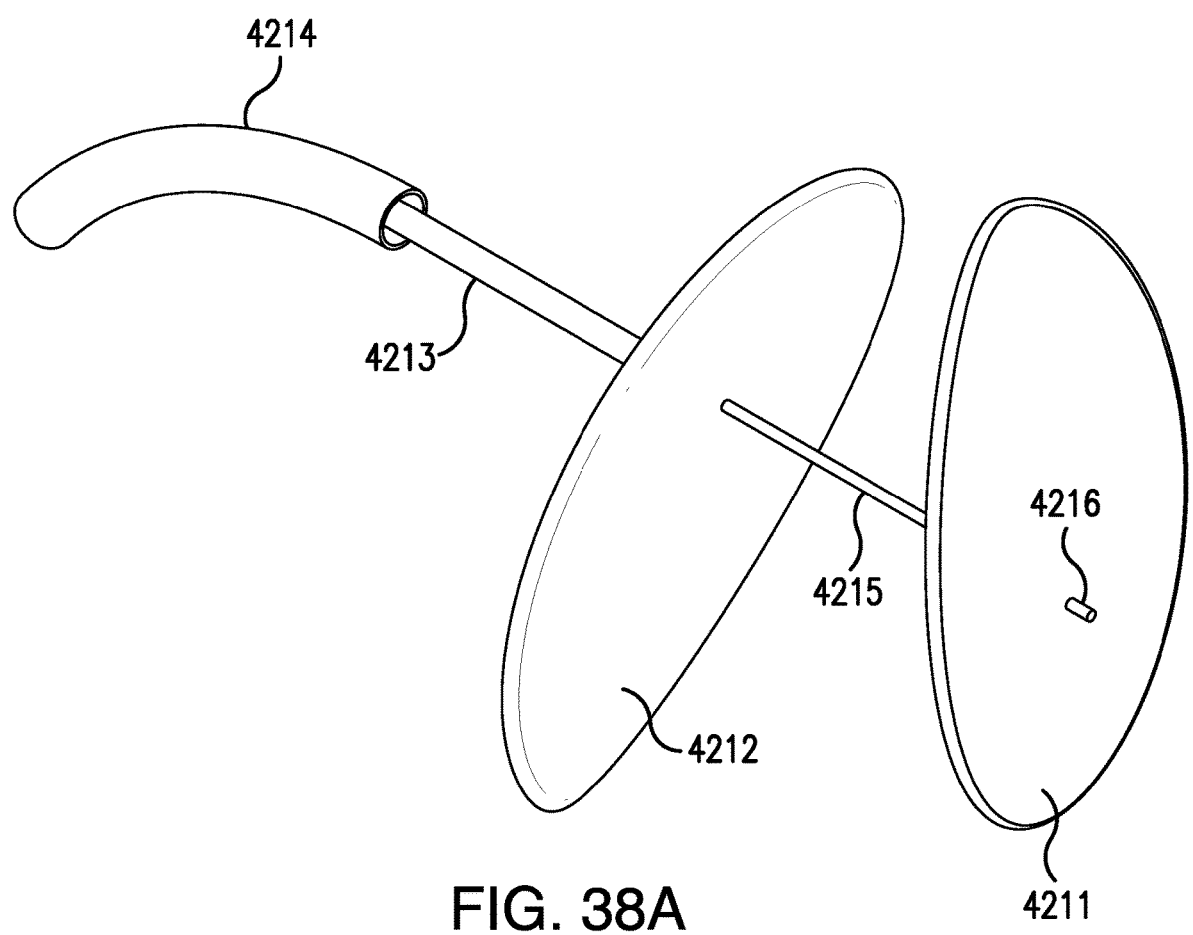
FIGS. 38A-D illustrate different views of an exemplary offset ellipses shaped telescoping laparoscopic mesh delivery system.
Figure 38B:
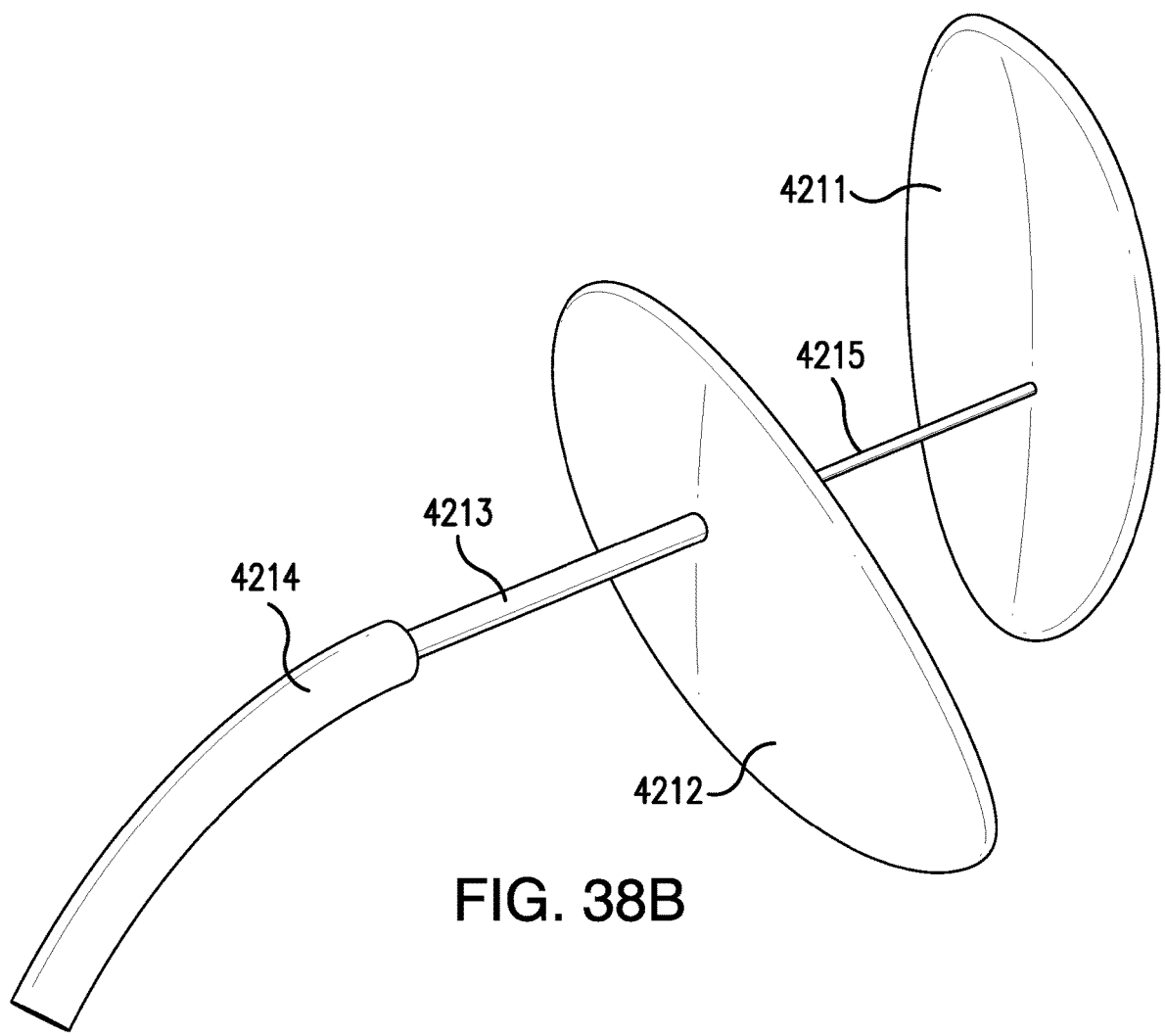
Figure 38C:
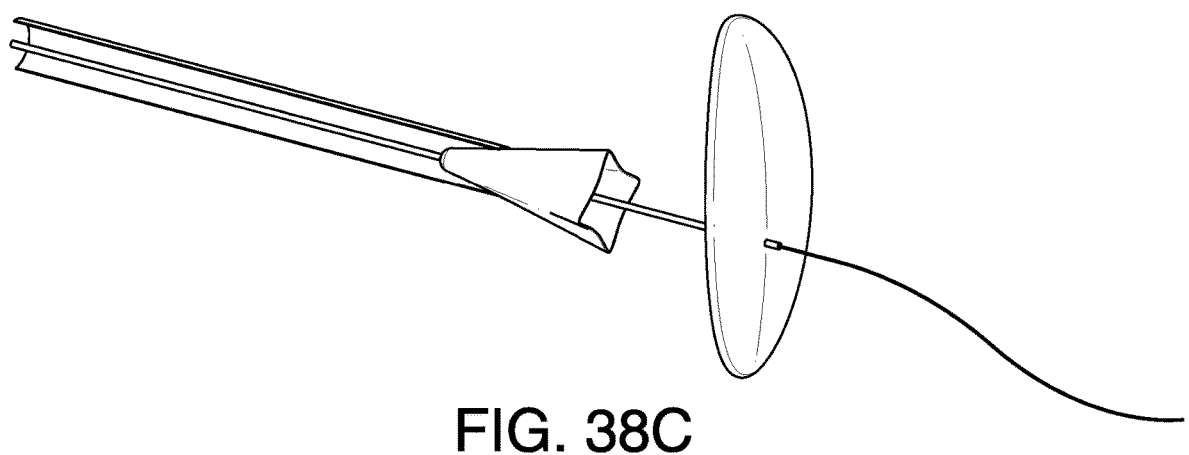
Figure 38D:
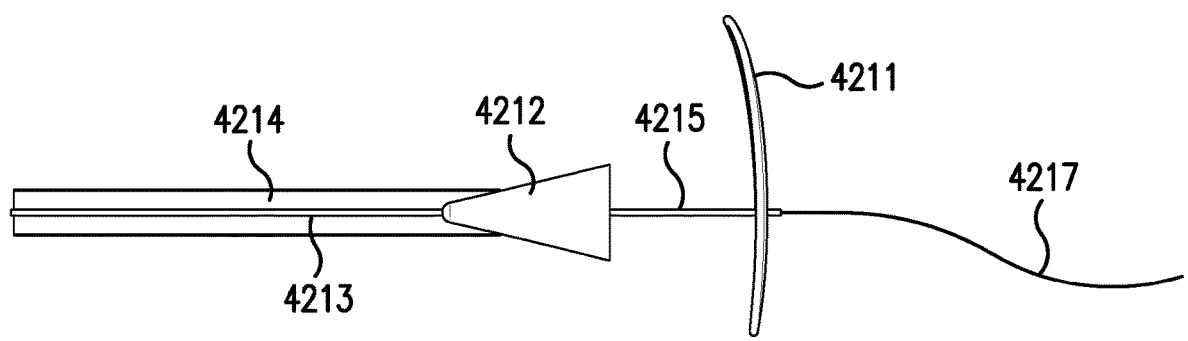

FIGS. 38C and 38D illustrate different views of the offset ellipses shaped telescoping laparoscopic mesh delivery system in a partial deployment configuration in which the proximal closure member 4212 is not fully deployed but the distal closure member 4211 is deployed. In some embodiments, the crescent member shaped telescoping laparoscopic mesh delivery system can be in a partially deployed configuration once the guidewire 4217 pulls the distal closure member 4211 out of the introducer shaft 3816 from a mesh delivery configuration. In the partially deployed configuration, the guidewire 4217 can still be in the process of being pulled and, accordingly, the proximal closure member 4212 can still not be fully deployed as it is being extracted out of the introducer shaft 4216.

In some embodiments, the proximal closure member 4212 can be attached to the top side of the fascia and the distal closure member 4211 can be attached to the underside of the fascia. The proximal closure member 4212 and the distal closure member 4211 can be opened from a pre-folded delivery configuration into a partially deployed configuration shown by pulling on the guidewire 4217.

Figure 39:
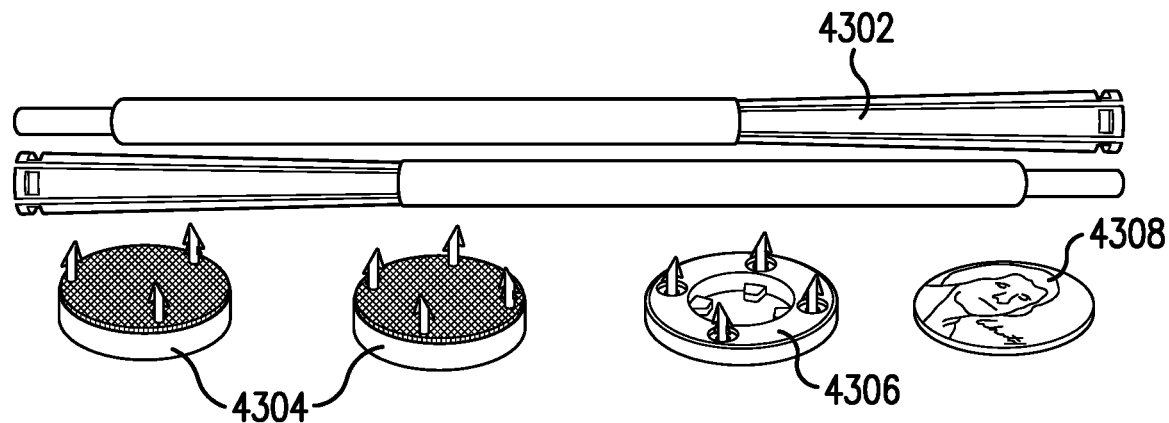
FIG. 39 illustrates an image of an exemplary telescoping laparoscopic mesh delivery system.

FIG. 39 illustrates an image of an exemplary telescoping laparoscopic mesh delivery system. The scale of the telescoping tube 4302 and the exemplary mesh retainer tacks 4304 and 4306 are illustrated by comparison to a U.S. nickel coin 4308.

Figure 40A:
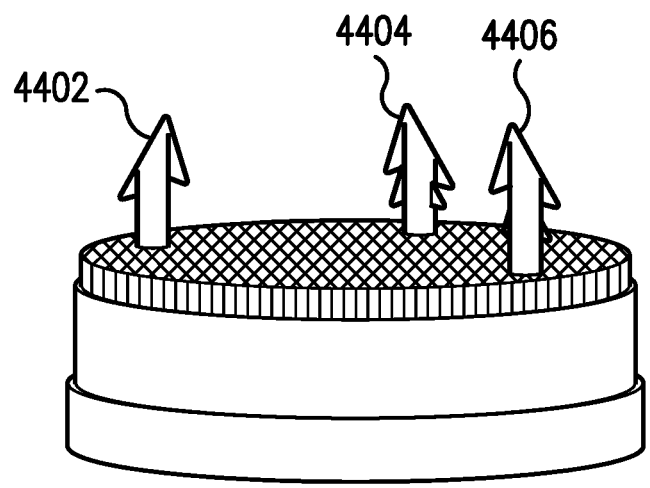
FIGS. 40A-C illustrate different retainer configurations.
Figure 40B:
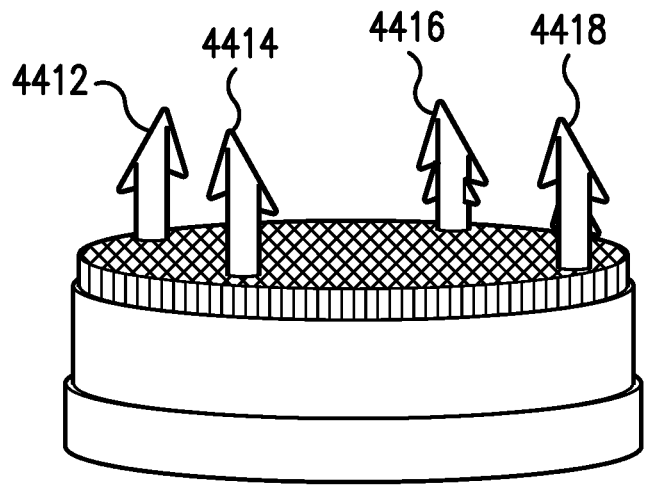
Figure 40C:
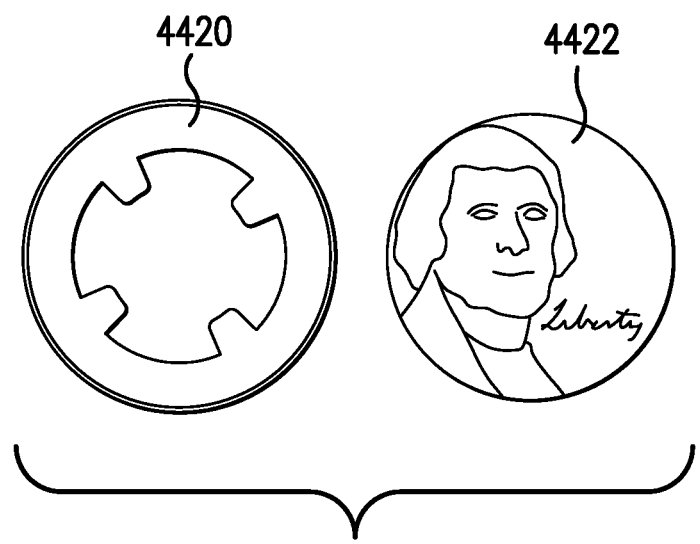

FIGS. 40A-C illustrate different retainer configurations. FIG. 40A illustrates a retainer having a three-barb configuration with barbs 4402, 4404, and 4406. FIG. 40B illustrates a retainer having a four-barb configuration with barbs 4412, 4414, 4416, and 4418. FIG. 40C illustrates scale of the four-barb retainer ring 4420 by comparison to a U.S. nickel coin 4422. According to the exemplary embodiment illustrated in FIG. 40C, the retainer ring 4420 can have a diameter of 21.21 mm and a thickness of 3.9 mm. The mesh in the retainer can be bonded to the retainer using cyanoacrylate UV-cure adhesives and then can be trimmed. In some embodiments, the mesh can be retained into the retainer by the barbs themselves. The mesh can peel back around the edges of the retainer. The mesh can be held back (e.g., flush) against the fascia stand-in.

Figure 41A:
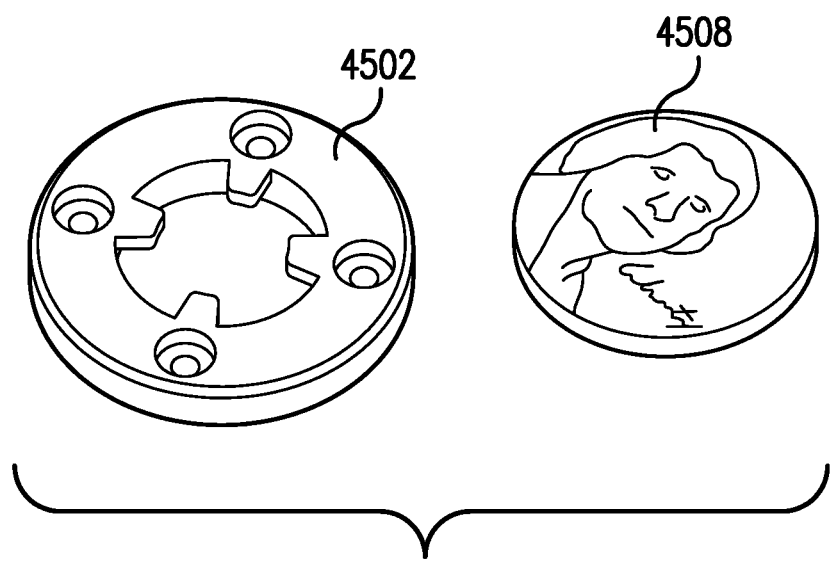
FIGS. 41A-B illustrate an embodiment in which retainers can include barb re-absorbable tacks.
Figure 41B:
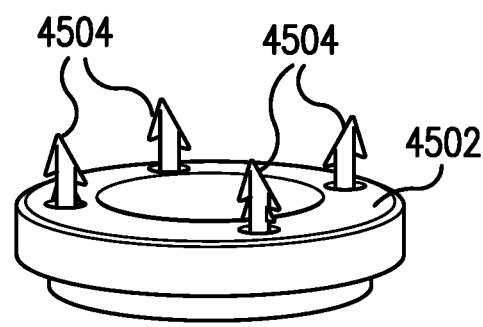

FIGS. 41A-B illustrate an embodiment in which retainers can include barb re-absorbable tacks. FIG. 41A illustrates the scale of retainer ring 4502 by comparison to a U.S.

nickel coin 4508. FIG. 41B illustrates that the retainer ring 4502 can include multiple (e.g., 4) barb re-absorbable tacks 4504 in the ring of the retainer 4502. The diameter of the retainer ring 4502 can be increased to maintain minimal wall thickness upon addition of the barb re-absorbable tacks. The retainer ring 4502 can be a fixation device that can be printed using serial lithography and/or other lithographic techniques (e.g., 3D printing, ion beam lithography etc.). The retainer ring 4502 can be left behind once it delivers the mesh to the fascial target site. For example, the retainer ring 4502 can be made of bioabsorbable and/or biocompatible materials.

In some embodiments, the disclosed telescoping laparoscopic mesh delivery system(s) can deliver the mesh using different mechanisms. FIGS. 42A-D, FIGS. 43A-D, and FIGS. 44A-D illustrate a few exemplary mechanisms for purpose of illustration and not limitation.

Figure 42A:
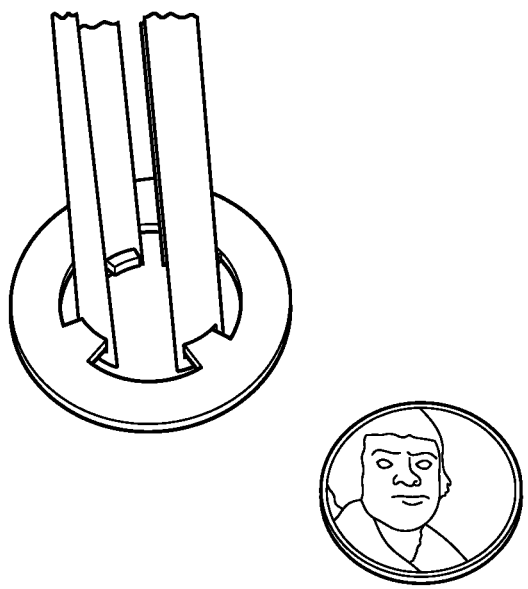
FIG. 42A-D illustrate a flow mechanism by which the telescoping laparoscopic mesh delivery system(s) can deliver the mesh.
Figure 42B:
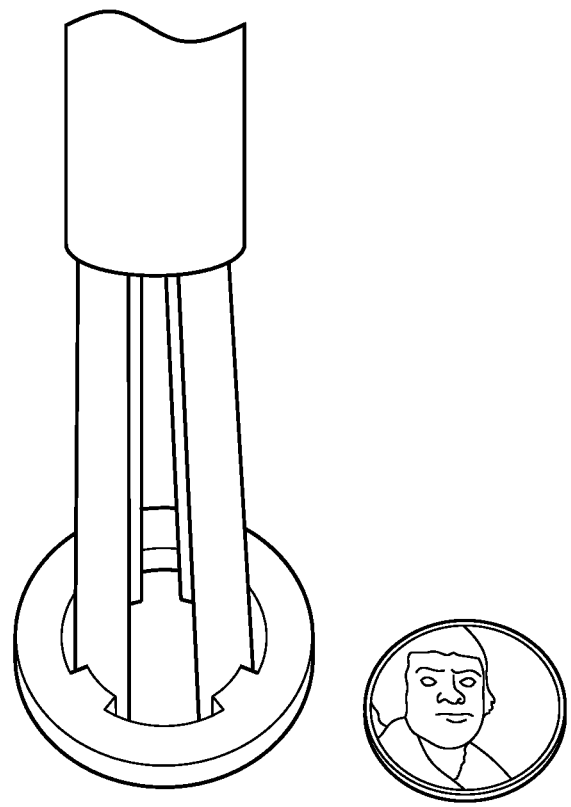
Figure 42C:
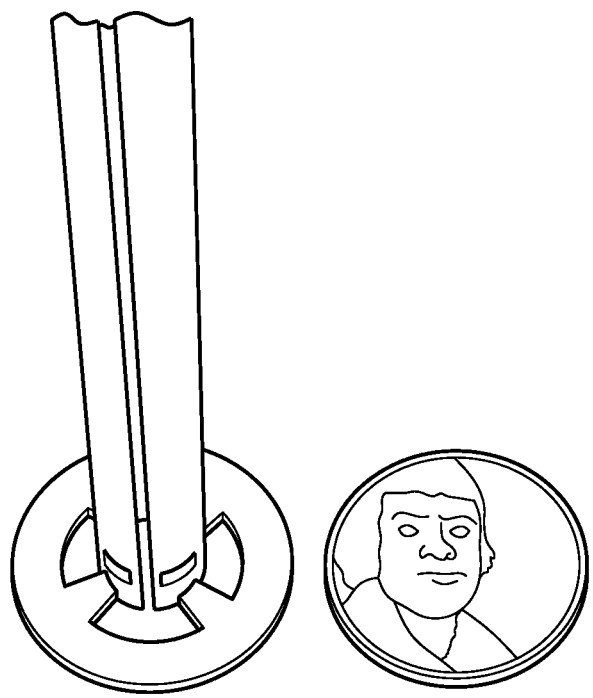
Figure 42D:
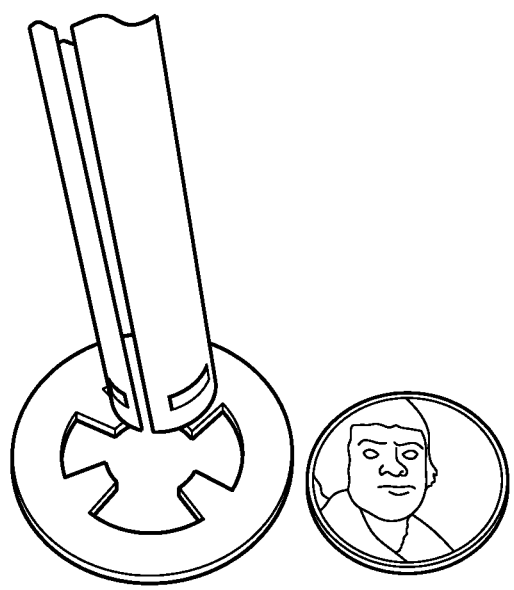

FIG. 42A-D illustrate a mechanism by which the telescoping laparoscopic mesh delivery system(s) can deliver the mesh. FIG. 42A shows that the mesh can be retained to the telescoping laparoscopic mesh delivery system. FIG. 42B shows that the mesh can be affixed to the telescoping laparoscopic mesh delivery system by pressing the mesh against the retainer ring against a hard surface such that the mesh is affixed to the delivery system by the retainer ring's barbed tacks. FIG. 42C shows that the retainer ring can be released from the telescoping laparoscopic mesh delivery system as pushing apparatus (e.g., push rod) is used to expel the mesh from the delivery system by pushing down on the retainer ring. FIG. 42D shows that the mesh with or without the retainer ring can be deployed from the telescoping laparoscopic mesh delivery system once the pushing apparatus expels the mesh from the affixed barbs.

Figure 43A:
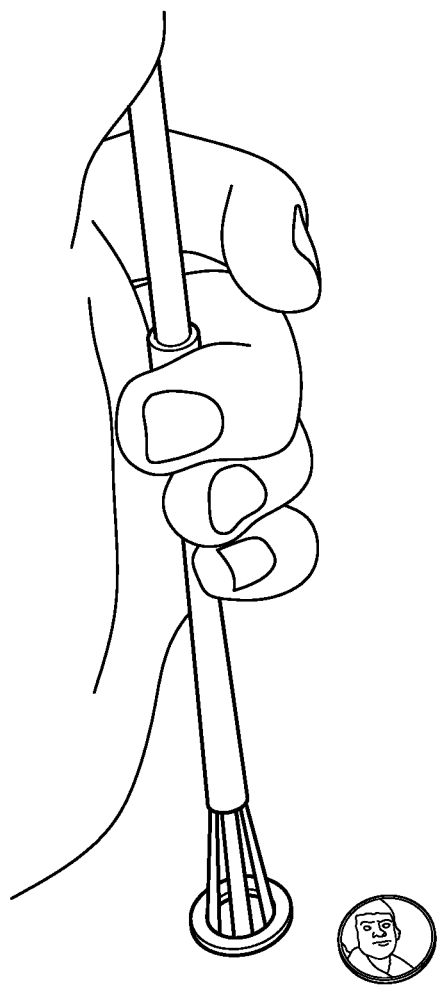
Figure 43B:
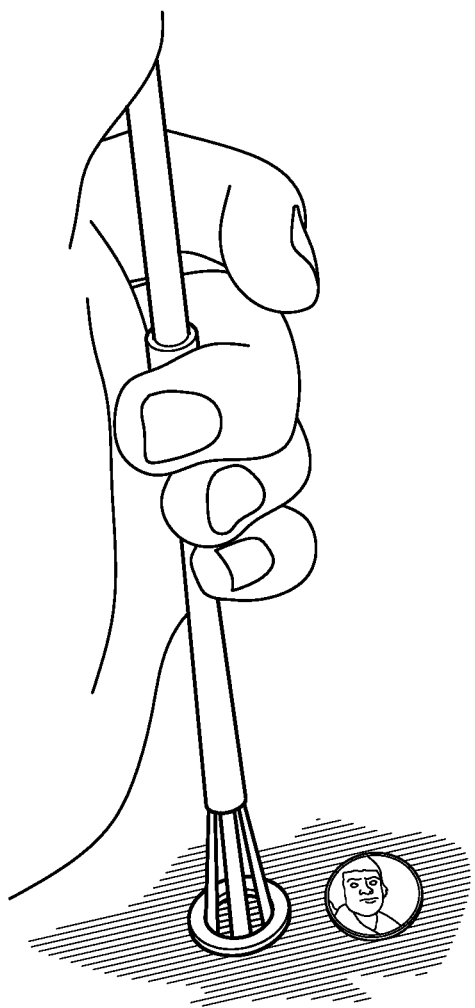

FIG. 43A-D illustrate that the telescoping laparoscopic mesh delivery system(s) can deliver the mesh using an interior energizer. In the embodiment illustrated in FIGS. 43A-D, the interior energizer can be a pull rod but other different types of interior energizers can be used. FIG. 43A shows that the mesh can be retained to the telescoping laparoscopic mesh delivery system. FIG. 43B shows that the mesh can be affixed to the telescoping laparoscopic mesh delivery system by pressing the mesh against the retainer ring against a hard surface such that the mesh is affixed to the delivery system by the retainer ring's barbed tacks. FIG. 43C shows that the pull rod can be released from a resting state to expel the mesh. FIG. 43D shows that the mesh can be deployed from the telescoping laparoscopic mesh delivery system once the pull rod has expelled the mesh. In some embodiments, the pull rod can be a laser cut wire made of a memory material. The pull rod can be configured such that pulling on the pull rod can increase the pressure and/or energy exerted on the retainer ring. As the pull rod is pulled by applying pressure outside the telescoping laparoscopic mesh delivery system, the pressure on the retainer ring increases until the retainer ring is expelled from the telescoping laparoscopic mesh delivery system.

Figure 44A:
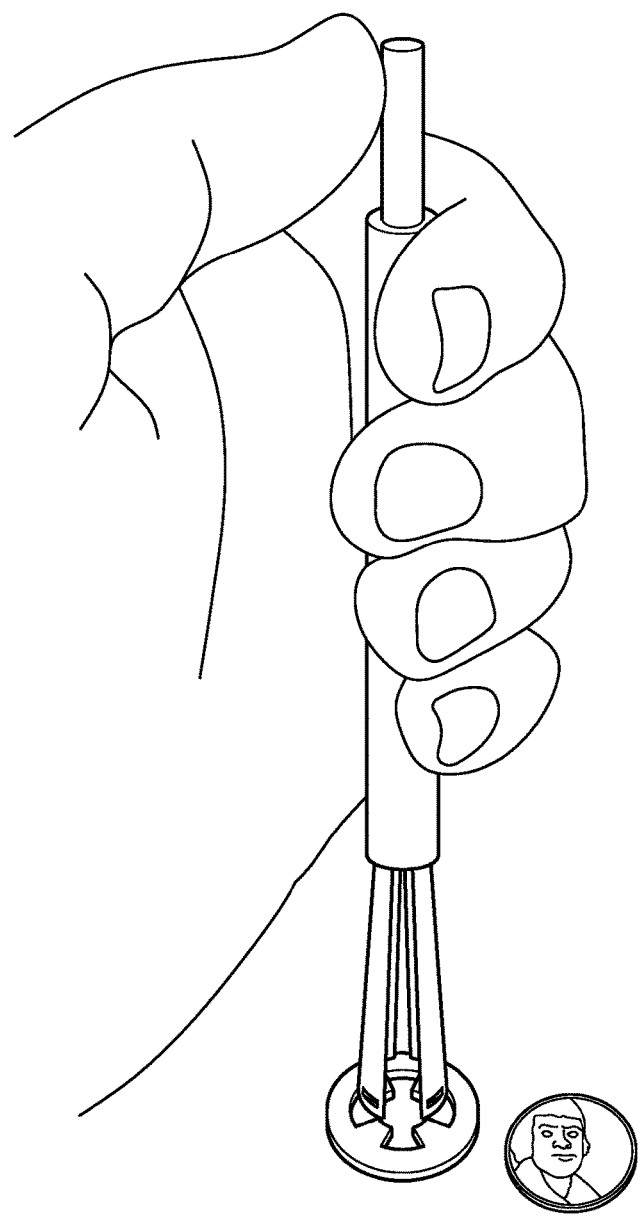
FIG. 44A-D illustrate that the telescoping laparoscopic mesh delivery system(s) can deliver the mesh using an exterior energizer.
Figure 44B:
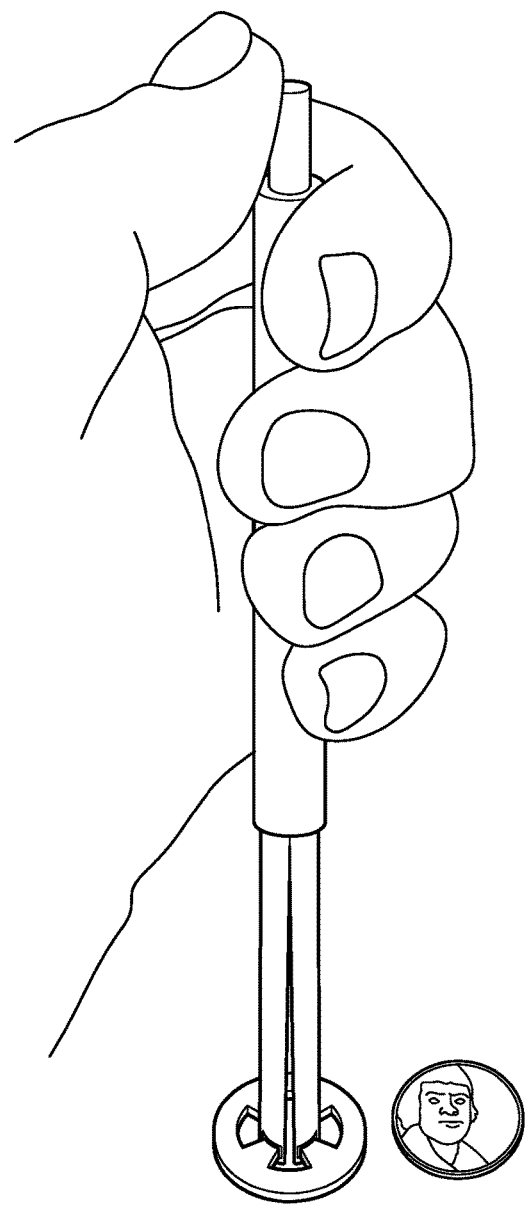
Figure 44C:
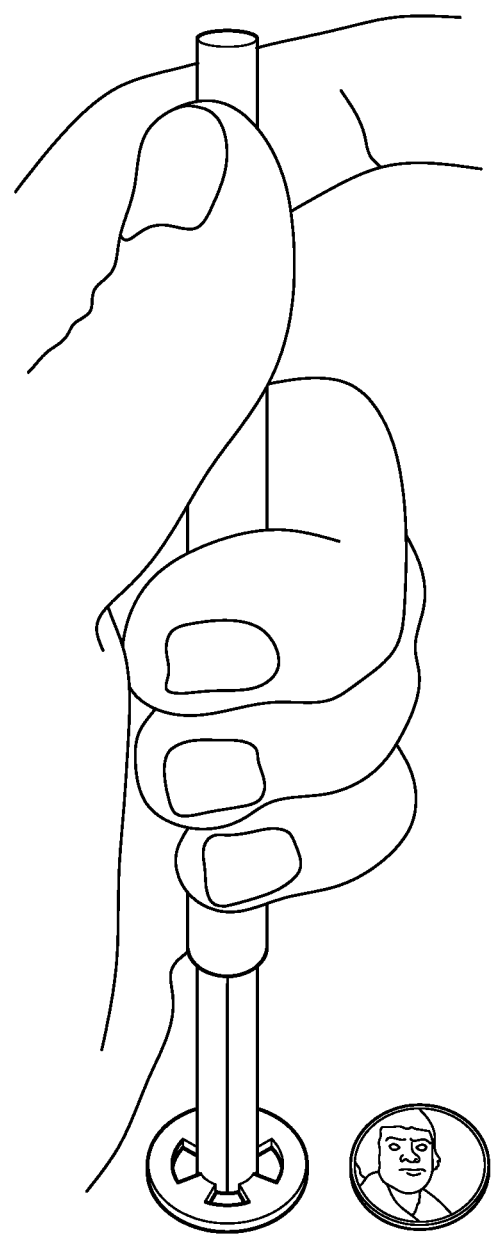
Figure 44D:
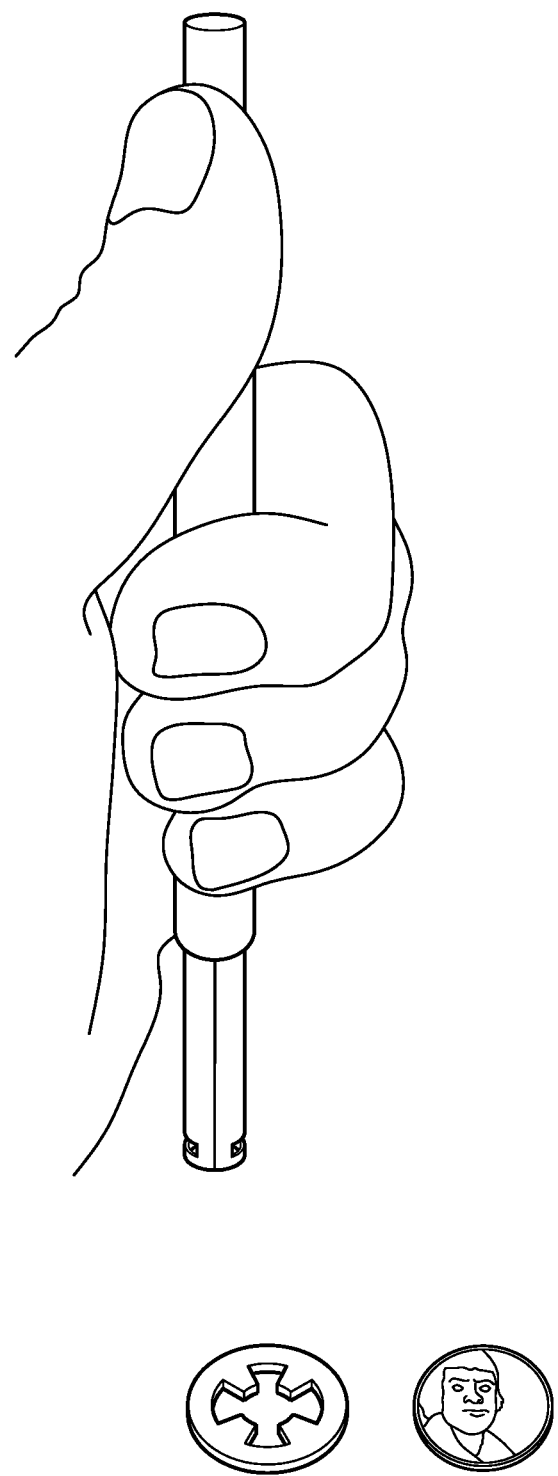

FIG. 44A-D illustrate that the telescoping laparoscopic mesh delivery system(s) can deliver the mesh using an exterior energizer. In the embodiment illustrated in FIGS. 44A-D, the exterior energizer can be a push rod but other different types of exterior energizers can be used. FIG. 44A shows that the mesh can be retained to the telescoping laparoscopic mesh delivery system. FIG. 44B shows that the mesh can be affixed to the telescoping laparoscopic mesh delivery system by pressing the mesh against the retainer ring against a hard surface such that the mesh is affixed to the delivery system by the retainer ring's barbed tacks. FIG. 44C shows that the push rod can be released from a resting state to expel the mesh from the delivery system. FIG. 44D shows that the mesh can be deployed from the telescoping laparoscopic mesh delivery system once the push rod has expelled the mesh. In some embodiments, the push rod can be a laser cut wire made of a memory material. The push rod can be configured such that pushing on the push rod can increase the pressure and/or energy and/or force exerted on the retainer ring. As the push rod is pushed by applying pressure outside the telescoping laparoscopic mesh delivery system, the pressure on the retainer ring increases until the retainer ring is expelled from the telescoping laparoscopic mesh delivery system.

In some embodiments, the interior energizer can be more effective at retaining the mesh than an exterior energizer. Due to flexibility of the SLA material used in the telescoping mesh delivery system, the exterior energizer cut-out flanges can be less stable when they are not restrained (e.g., during retention). In some embodiments, laser-cut hypotubes can be used to improve overall performance of the flanges in retaining their shape.

Figure 45A:
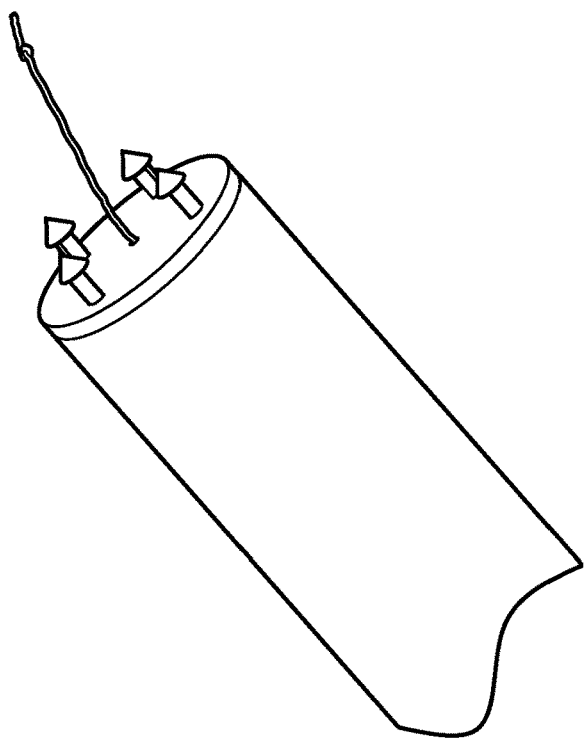
FIGS. 45A-C illustrate different views of an exemplary housing of an telescoping laparoscopic mesh delivery system.
Figure 45B:
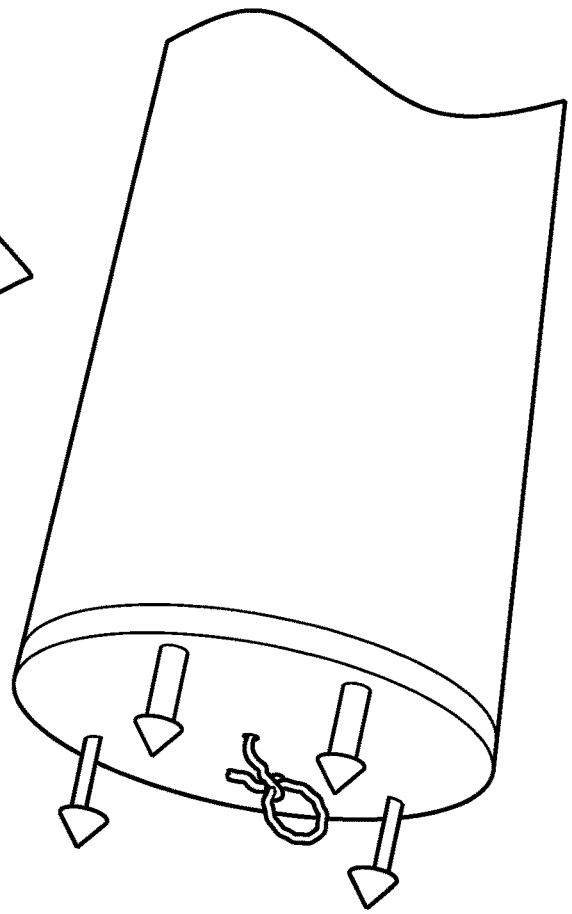
Figure 45C:
Figure 46A:
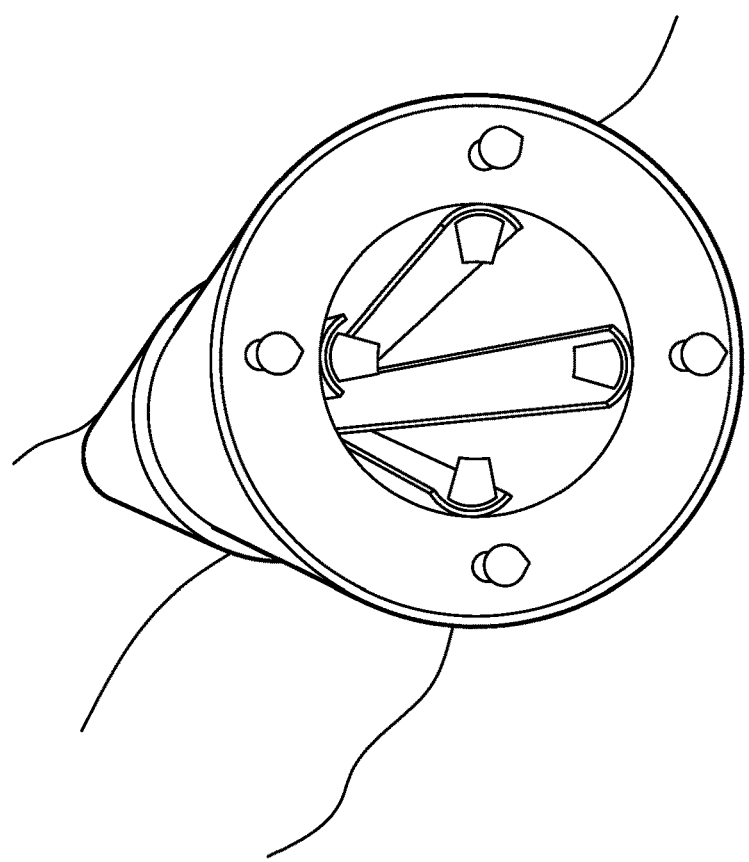
FIGS. 46A-B illustrate different views of an exemplary laser cut flared hypotube used for an exemplary telescoping laparoscopic mesh delivery system.
Figure 46B:
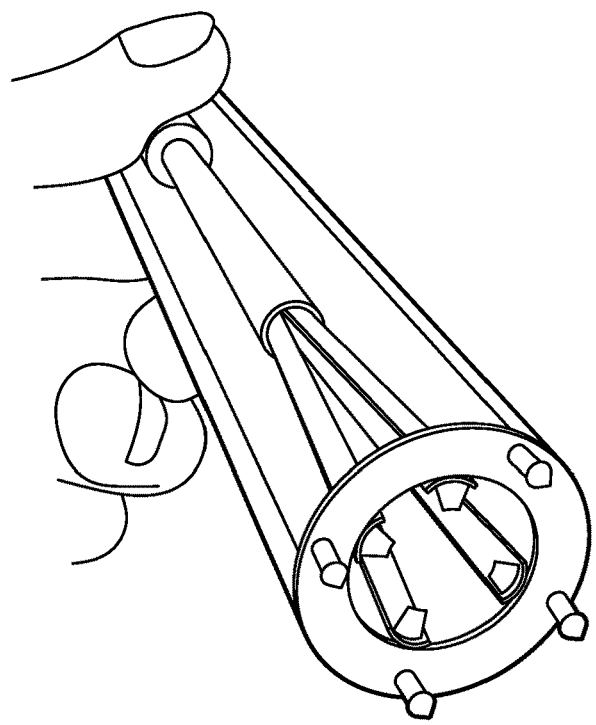

FIGS. 45A-C illustrate different views of an exemplary housing of an telescoping laparoscopic mesh delivery system. Such an overall housing can provide axial alignment of the delivery system with a retainer, which can aid in the removal of delivery device after the retainer is released. FIG. 45A illustrates an end of the exemplary housing with a thread and/or guidewire protruding from the end pictured in FIG. 45A. FIG. 45B illustrates the other end of the housing apparatus and illustrates that the mesh, which can be positioned at the other end through a retainer ring, can be attached to the thread and/or guidewire. The thread and/or guidewire can be used to grab onto the suture threads. FIG. 45C shows a side view of the entire housing of the telescoping laparoscopic mesh delivery system, FIGS. 46A-B illustrate different views of an exemplary laser cut flared hypotube used for an exemplary telescoping laparoscopic mesh delivery system. As illustrated in FIGS. 46A-B, two different hypotubes can be used. At least one of the hypotubes can include digits, such as digits 4680, 4681, 4682, and 4683 that can be used to retain and/or hold onto the tacks attached to the mesh. The second hypotube can slide over the flared out hypotube and can energize the digits to release the tacks that are attached to the fascia.

Figure 47A:
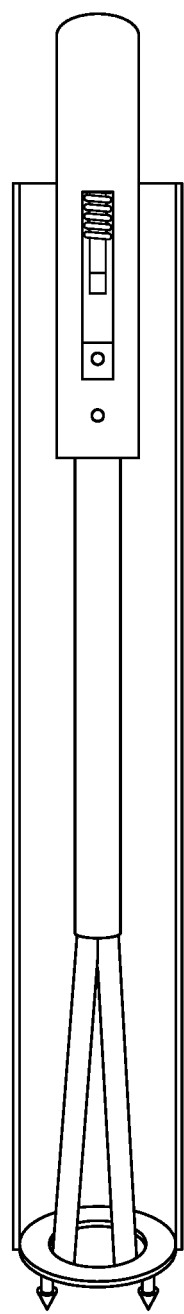
FIGS. 47A-C illustrate different stages of operation of the exemplary telescoping laparoscopic mesh delivery system shown in FIGS. 46A-B.
Figure 47B:
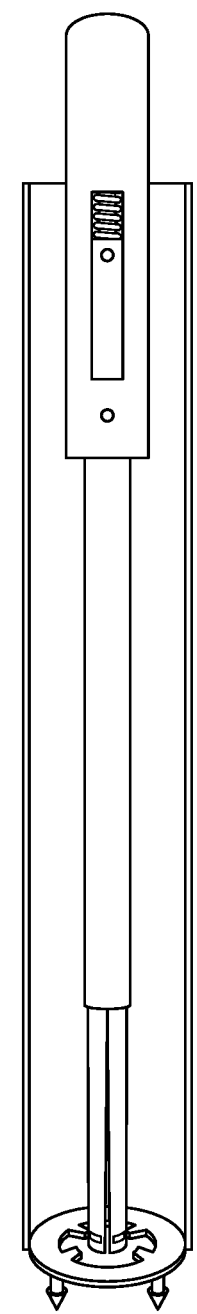
Figure 47C:
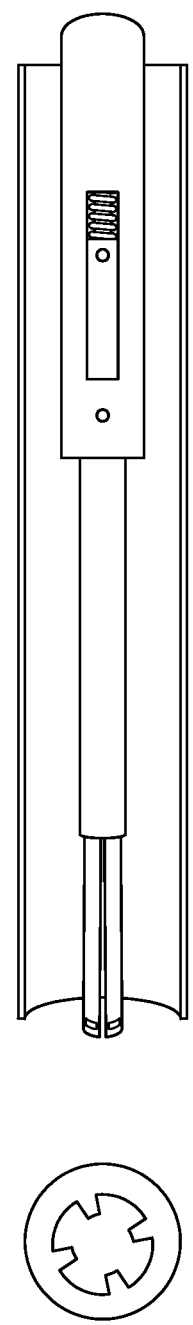

FIGS. 47A-C illustrate different stages of operation of the exemplary telescoping laparoscopic mesh delivery system shown in FIGS. 46A-B. In some embodiments, by pushing on the housing (e.g., an overhang and/or pushbutton on the housing), the tacks can be pushed due to deformation of the housing and consequently, the tacks can be deployed.

Figure 48A:
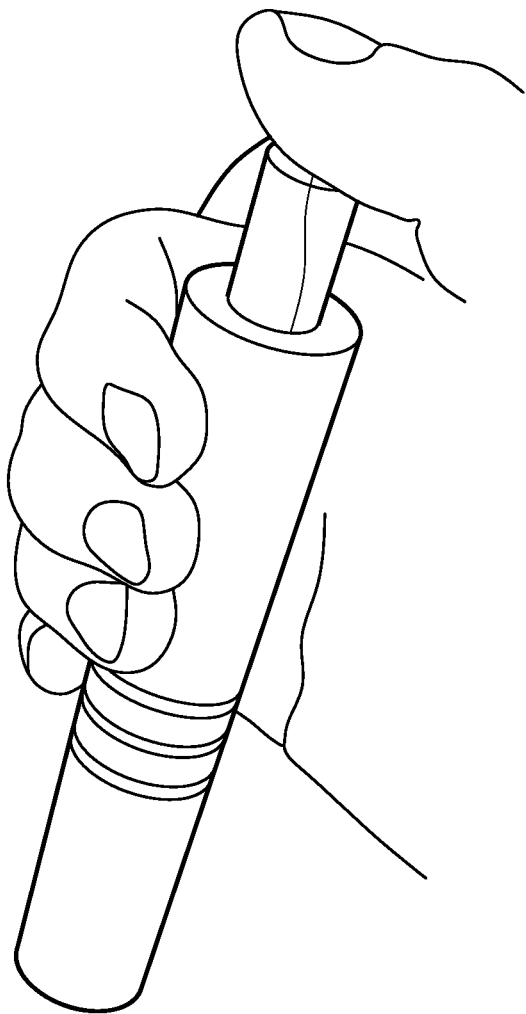
FIGS. 48A-B and 49A-B illustrate different views of an exemplary telescoping laparoscopic mesh delivery system with a pushbutton.
Figure 48B:
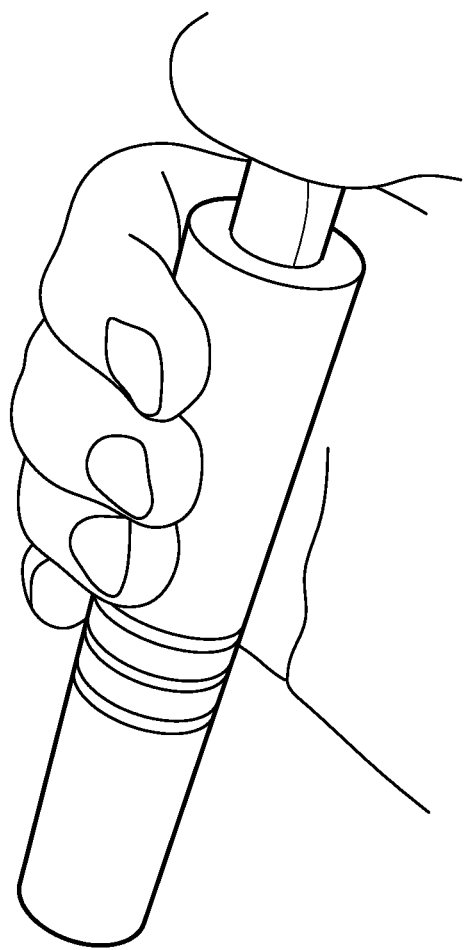
Figure 49A:
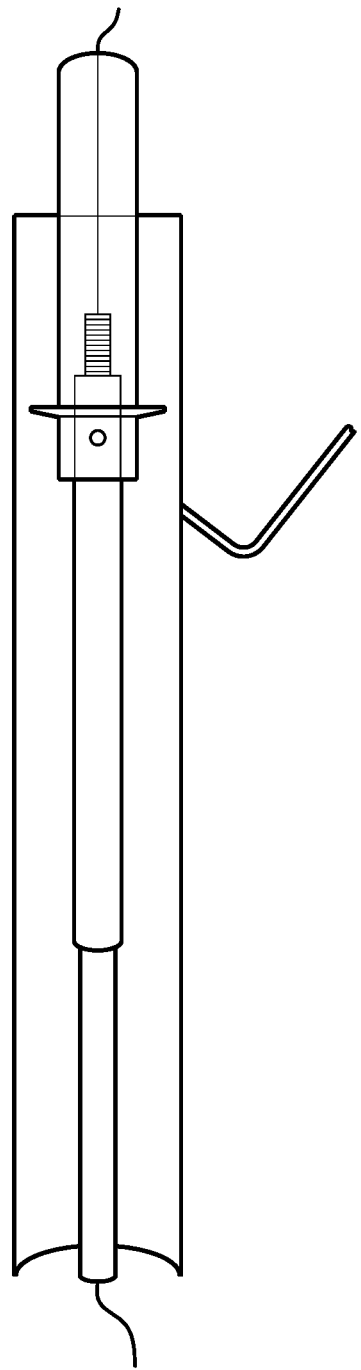
Figure 49B:
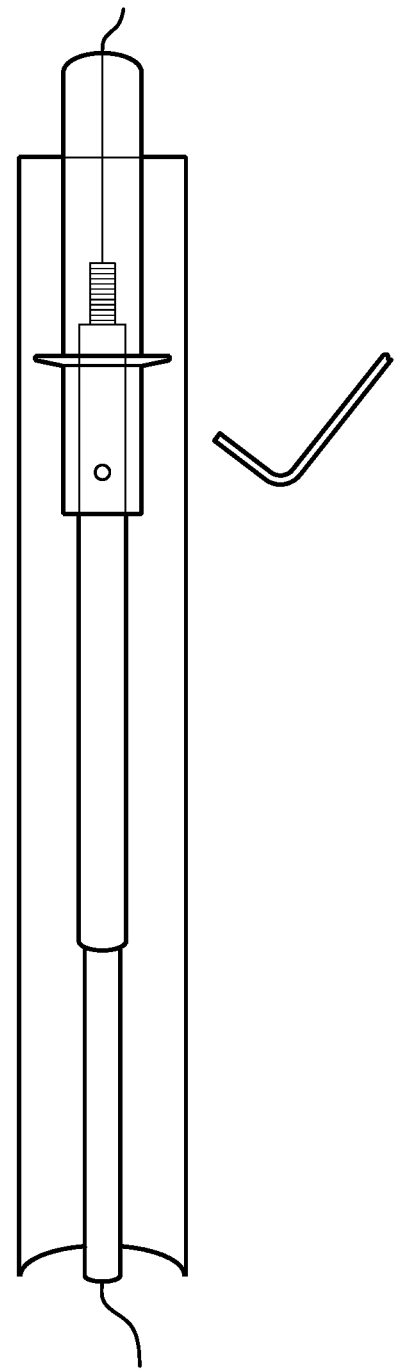

FIGS. 48A-B and 49A-B illustrate different views of an exemplary telescoping laparoscopic mesh delivery system with a pushbutton. FIGS. 48A-B illustrate images of the exterior of the housing with the pushbutton being pushed. FIGS. 49A-B illustrate a cross-section view of the housing with the pushbutton. As illustrated in FIGS. 49A-B, the pushbutton can include a spring and the pushbutton can have a thread and/or guidewire protruding from it. In some embodiments, a button can be used to automate release of the mesh using the exterior energizer and interior energizers described in FIGS. 43A-D and FIGS. 44A-D. For example, pressing such a button can instruct a mechanical arm and/or other apparatus to release the push rod and/or pull rod.

Figure 50A:
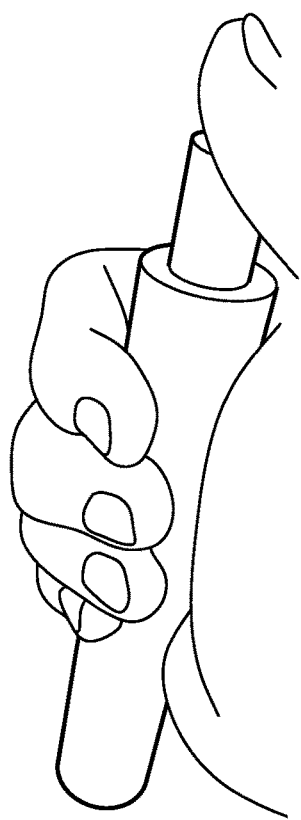
FIGS. 50A-C illustrate different steps of an exemplary tack deployment process using an exemplary telescoping laparoscopic mesh delivery system.
Figure 50B:
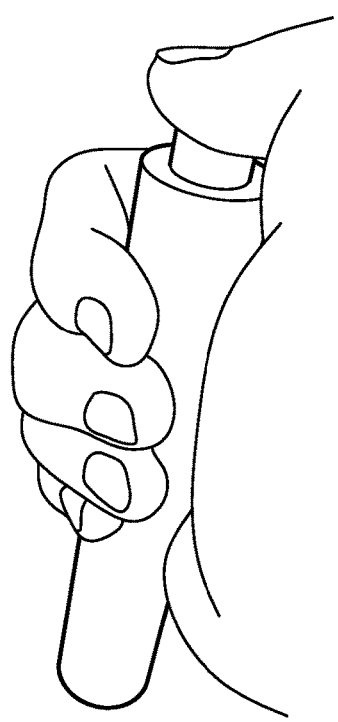
Figure 50C:
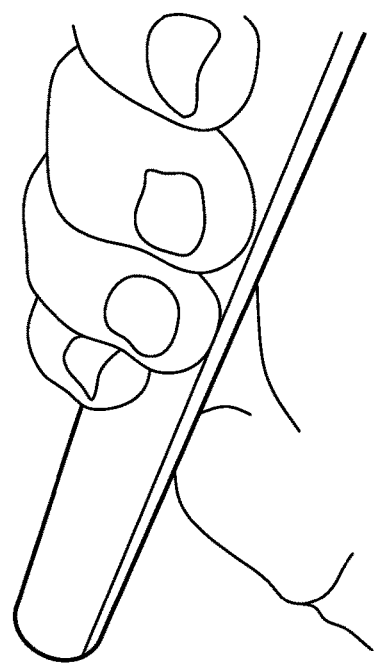
Figure 51A:
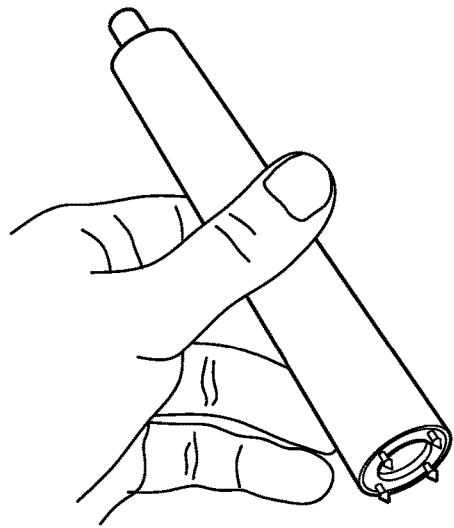
FIGS. 51A-D illustrate different views of an exemplary housing of an exemplary telescoping laparoscopic mesh delivery system.
Figure 51B:
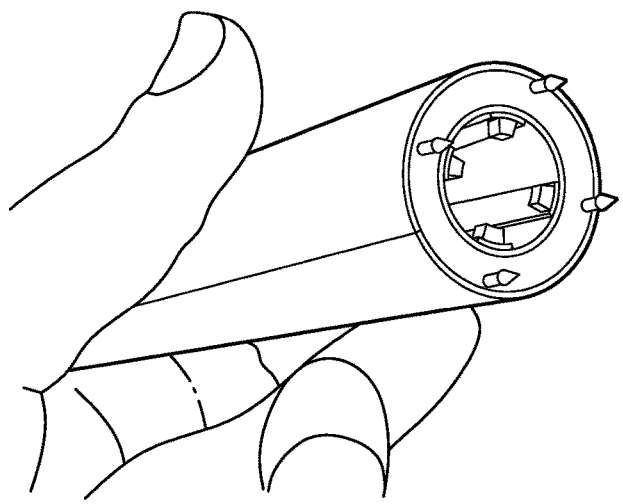
Figure 51C:
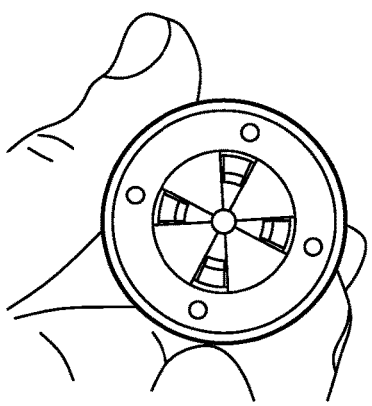
Figure 51D:
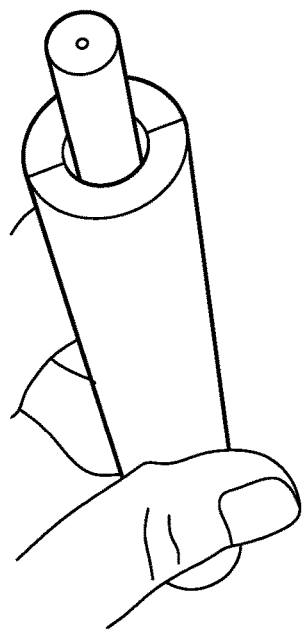

FIGS. 50A-C illustrate different steps of an exemplary tack deployment process using an exemplary telescoping laparoscopic mesh delivery system as the pushbutton is being pressed FIGS. 51A-D illustrate different views of an exemplary housing of an exemplary telescoping laparoscopic mesh delivery system. The housing can be made to be of a non-transparent material.

Figure 52A:
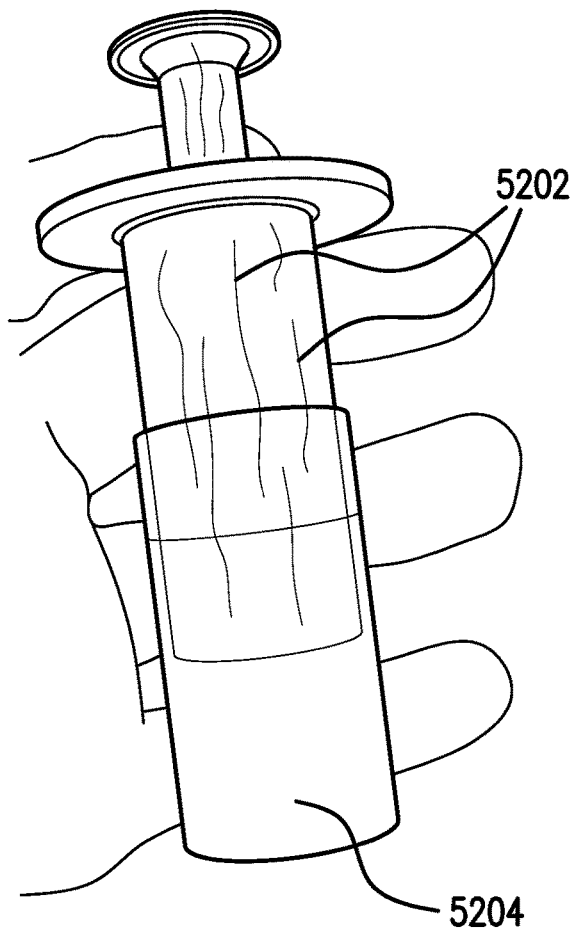
FIGS. 52A-C illustrate different views of an exemplary obturator and cannula to be used in conjunction with an exemplary telescoping laparoscopic mesh delivery system.
Figure 52B:
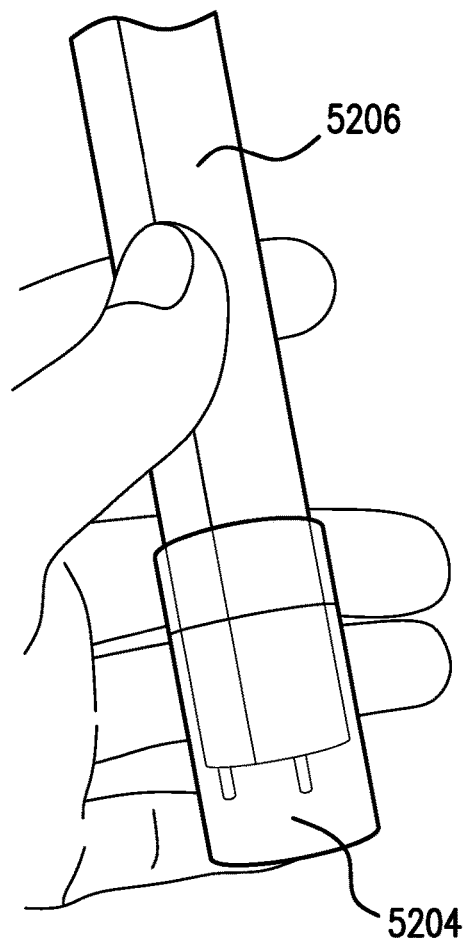
Figure 52C:
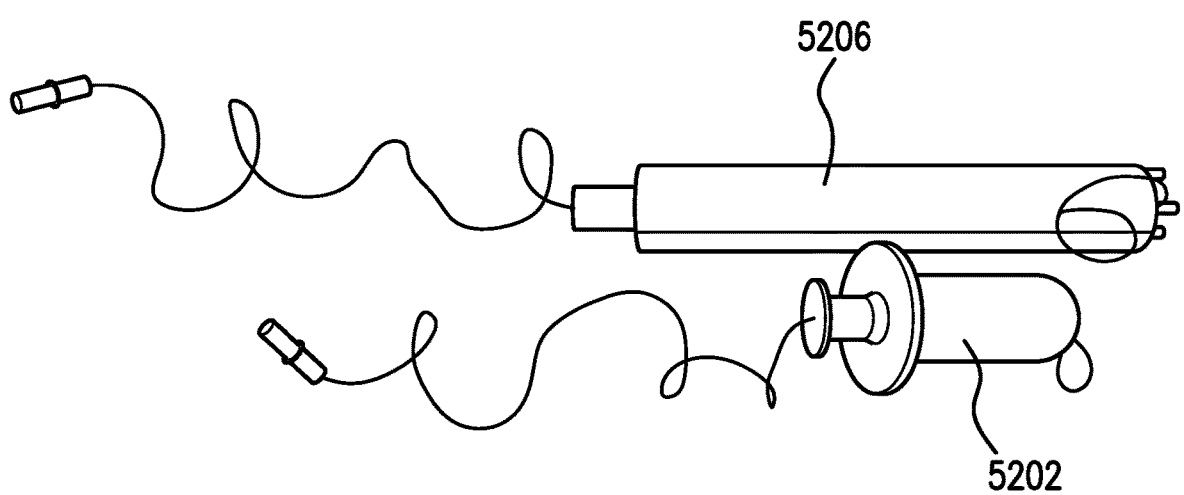

FIGS. 52A-C illustrate different views of an exemplary obturator and cannula to be used in conjunction with an exemplary telescoping laparoscopic mesh delivery system. The obturator 5202 can be a metal or plastic sharpened or non-bladed tip which can make an incision and/or a pathway for the telescoping laparoscopic mesh delivery system to be placed in to provide a clear unobtrusive path to the fascial tissue and/or site of the fascial tissue reinforcement and/or mesh delivery. The cannula, which can be a hollow tube, can be used to preserve the pathway created by the cannula 5202. The cannula can serve as a portal for the subsequent placement of the telescoping laparoscopic mesh delivery system 5206.

The presently disclosed subject matter is not to be limited in scope by the specific embodiments herein. Indeed, various modifications of the disclosed subject matter in addition to those described herein will become apparent to those skilled in the art from the foregoing description and the accompanying figures. Such modifications are intended to fall within the scope of the appended claims.

The invention claimed is:

1. A method for positioning and affixing reinforcing material to abdominal wall fascia to reinforce and augment a fascial incision closure following a laparoscopic or minimally invasive procedure, comprising:
    positioning the reinforcing material at an anterior surface of the abdominal wall fascia over the fascial incision closure using a telescoping arm;
    mechanically fastening the reinforcing material to the anterior surface of the abdominal wall fascia by applying a force to the telescoping arm with the reinforcing material positioned at the anterior surface of the abdominal wall fascia; and
    detaching the reinforcing material from the telescoping arm.

2. The method of claim 1, wherein the telescoping arm is configured to affix the reinforcing material to the anterior surface of the abdominal wall fascia by applying the force, wherein the force applied to the reinforcing material can be controlled by a guide coupled to the telescoping arm.

3. The method of claim 1, wherein the reinforcing material is attached to the telescoping arm in a delivery configuration, and wherein the reinforcing material is maintained in the delivery configuration until the reinforcing material is proximate to the anterior surface of the abdominal wall fascia.

4. The method of claim 1, wherein the reinforcing material is deployed from a delivery configuration after passing through an incision.

5. The method of claim 4, wherein the reinforcing material is deployed from the delivery condition to a deployed condition with a spring.

6. The method of claim 1, wherein mechanically fastening the reinforcing material includes applying one or more of a biologic or biomedical adhesive or glue.

7. The method of claim 1, wherein mechanically fastening the reinforcing material includes using fasteners.

8. The method of claim 7, wherein the fasteners are configured to have a cutting edge on the outer periphery of the fasteners.

9. The method of claim 7, wherein the fasteners include an anchoring mechanism comprising a barbed affixation with a barb adapted for a predetermined amount of fascia penetration.

10. The method of claim 7, wherein the fasteners are integrated with the reinforcing material.

11. The method of claim 1, wherein detaching includes cutting the reinforcing material.

12. The method of claim 1, wherein detaching includes advancing the telescoping arm.

13. The method of claim 1, wherein the telescoping arm includes inner and outer tubes and wherein detaching includes advancing the inner tube.

14. The method of claim 1, wherein the telescoping arm includes at least one knob and wherein detaching includes rotating the at least one knob.

15. The method of claim 1, wherein the reinforcing material is attached to a breakaway component.

16. The method of claim 1, further comprising tensioning the reinforcing material.

17. The method of claim 1, wherein the reinforcing material comprises one or more of a permanent synthetic material, a biologic material, a bio-absorbable material, a mesh, and combinations thereof.

* * * * *